United States Patent
Apt et al.

(10) Patent No.: US 10,085,465 B2
(45) Date of Patent: Oct. 2, 2018

(54) THRAUSTOCHYTRIDS, FATTY ACID COMPOSITIONS, AND METHODS OF MAKING AND USES THEREOF

(71) Applicant: DSM IP Assets B.V., TE Heerlen (NL)

(72) Inventors: Kirk E. Apt, Ellicott City, MD (US); Joseph W. Pfeifer, III, Westminster, MD (US); Jon Milton Hansen, Chandler, AZ (US); Paul Warren Behrens, Ellicott City, MD (US); Ross Zirkle, Mt Airy, MD (US); Tracey Lynn Stahl, Pasadena, MD (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 15/209,568

(22) Filed: Jul. 13, 2016

(65) Prior Publication Data
US 2016/0309748 A1  Oct. 27, 2016

Related U.S. Application Data

(62) Division of application No. 13/220,259, filed on Aug. 29, 2011, now Pat. No. 9,414,612, which is a division of application No. 12/407,687, filed on Mar. 19, 2009, now Pat. No. 8,207,363.

(51) Int. Cl.
| | | |
|---|---|---|
| C11C 3/00 | (2006.01) | |
| A23K 20/158 | (2016.01) | |
| A23D 9/00 | (2006.01) | |
| A61K 31/20 | (2006.01) | |
| C12P 7/64 | (2006.01) | |
| C12R 1/89 | (2006.01) | |
| A23K 50/80 | (2016.01) | |
| A23L 33/115 | (2016.01) | |
| A23L 33/135 | (2016.01) | |
| A23K 50/00 | (2016.01) | |
| A23L 33/12 | (2016.01) | |
| A61K 8/99 | (2017.01) | |
| A61K 31/202 | (2006.01) | |
| A61K 36/02 | (2006.01) | |
| A61Q 19/00 | (2006.01) | |
| A61K 35/00 | (2006.01) | |

(52) U.S. Cl.
CPC .............. *A23K 20/158* (2016.05); *A23D 9/00* (2013.01); *A23K 50/00* (2016.05); *A23K 50/80* (2016.05); *A23L 33/115* (2016.08); *A23L 33/12* (2016.08); *A23L 33/135* (2016.08); *A61K 8/99* (2013.01); *A61K 31/20* (2013.01); *A61K 31/202* (2013.01); *A61K 36/02* (2013.01); *A61Q 19/00* (2013.01); *C12P 7/6427* (2013.01); *C12P 7/6472* (2013.01); *C12R 1/89* (2013.01); *A23V 2002/00* (2013.01); *A61K 2035/11* (2013.01); *A61K 2800/74* (2013.01)

(58) Field of Classification Search
CPC .................................. C11C 3/00; A23L 33/12
See application file for complete search history.

(56) References Cited

U.S. PATENT DOCUMENTS

| | | | |
|---|---|---|---|
| 6,509,178 B1 | 1/2003 | Tanaka et al. | |
| 7,259,006 B2 | 8/2007 | Komazawa et al. | |
| 2007/0226814 A1* | 9/2007 | Kiy ........................ | A23K 10/12 800/8 |

FOREIGN PATENT DOCUMENTS

| | | |
|---|---|---|
| CA | 2687523 A1 | 11/2008 |
| CN | 1648233 A | 8/2005 |
| WO | WO9737032 A2 | 10/1997 |
| WO | WO2008049512 | 5/2008 |

OTHER PUBLICATIONS

Perveen, Biotechnology Letters, Isolation and characterization of a novem thraustochytrid-like microorganism that efficiently produces docosahexaenoic acid, 2006, pp. 197-202, 28.

Westerop, Biomolecular Engineering, Basics and Applications, 2003, p. 37-82, 20.

Jeh et al., Lipid body formation by Thraustochytrium aureum (ATCC 34304) in resonse to cell age, Korean J. Chem. Eng., 2008, 1103-1109, 25(5).

Lim et al., A Diet Enriched with the Omega-3 Fatty Acid Docosahexaenoic Acid Reduces Amyloid Burden in an Aged Alzheimer Mouse Model, The Journal of Neuroscience, Mar. 23, 2005, 3032-3040, 25(12).

* cited by examiner

*Primary Examiner* — Rosanne Kosson
(74) *Attorney, Agent, or Firm* — Xi Chen; Shannon McGarrah

(57) ABSTRACT

The present invention is directed to isolated thraustochytrid microorganisms as well as strains and mutants thereof. The invention is further directed to biomasses, microbial oils, compositions, cultures, methods of producing microbial oils, and methods of using the isolated thraustochytrids, biomasses, and microbial oils.

22 Claims, No Drawings
Specification includes a Sequence Listing.

THRAUSTOCHYTRIDS, FATTY ACID COMPOSITIONS, AND METHODS OF MAKING AND USES THEREOF

This application is a divisional of U.S. application Ser. No. 13/220,259, which is a divisional of U.S. application Ser. No. 12/407,687 filed Mar. 19, 2009, which are hereby incorporated by reference in their entirety.

REFERENCE TO A SEQUENCE LISTING SUBMITTED ELECTRONICALLY

The content of the electronically submitted sequence listing ("sequence listing.txt", 10,531 bytes, created on Feb. 26, 2009) filed with the application is incorporated herein by reference in its entirety.

BACKGROUND OF THE INVENTION

Field of the Invention

The present invention is directed to isolated thraustochytrid microorganisms as well as strains and mutants thereof. The invention is further directed to thraustochytrid biomasses, microbial oils, compositions, cultures, methods of producing the microbial oils, and methods of using the isolated thraustochytrids, biomasses, and microbial oils.

Background Art

Fatty acids are classified based on the length and saturation characteristics of the carbon chain. Short chain fatty acids generally have 12 carbons or less, medium chain fatty acids generally have 14 to 18 carbons, and long chain fatty acids generally have 20 or more carbons. Fatty acids are termed saturated fatty acids when no double bonds are present between the carbon atoms and are termed unsaturated fatty acids when double bonds are present. Unsaturated long chain fatty acids are monounsaturated when only one double bond is present and are polyunsaturated when more than one double bond is present.

Polyunsaturated fatty acids (PUFAs) are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 long chain polyunsaturated fatty acid (LC-PUFA) with a chain length of 22 carbons and 6 double bonds, often designated as "22:6 n-3." Other omega-3 LC-PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 LC-PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., *Proc. Nutr. Soc.* 58: 397-401 (1999). DHA, for example, accounts for approximately 15%-20% of lipids in the human cerebral cortex, 30%-60% of lipids in the retina, is concentrated in the testes and sperm, and is an important component of breast milk. Jean-Pascal Bergé & Gilles Barnathan, *Fatty Acids from Lipids of Marine Organisms: Molecular Biodiversity, Roles as Biomarkers, Biologically Active Compounds, and Economical Aspects*, in Marine Biotechnology I 49 (T. Scheper, ed., 2005). DHA accounts for up to 97% of the omega-3 fatty acids in the brain and up to 93% of the omega-3 fatty acids in the retina. Moreover, DHA is essential for both fetal and infant development as well as maintenance of cognitive functions in adults. Id. Omega-3 fatty acids, including DHA and EPA, also possess anti-inflammatory properties. See, e.g., Id. and Simopoulos, A. P., *J. Am. Coll. Nutr.* 21: 495-595 (2002). Because omega-3 fatty acids are not synthesized de novo in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Thraustochytrids are microorganisms of the order Thraustochytriales. Thraustochytrids include members of the genus *Schizochytrium* and have been recognized as an alternative source of omega-3 fatty acids, including DHA. See U.S. Pat. No. 5,130,242. Oils produced from these marine heterotrophic microorganisms often have simpler polyunsaturated fatty acid profiles than corresponding fish or microalgal oils. Lewis, T. E., *Mar. Biotechnol.* 1: 580-587 (1999). Strains of thraustochytrid species have been reported to produce omega-3 fatty acids as a high percentage of the total fatty acids produced by the organisms. U.S. Pat. No. 5,130,242; Huang, J. et al., *J. Am. Oil. Chem. Soc.* 78: 605-610 (2001); Huang, J. et al., *Mar. Biotechnol.* 5: 450-457 (2003). However, isolated thraustochytrids vary in the identity and amounts of LC-PUFAs produced, such that some previously described strains can have undesirable levels of omega-6 fatty acids and/or can demonstrate low productivity in culture. As such, a continuing need exists for the isolation of thraustochytrids demonstrating high productivity and desirable LC-PUFA profiles.

BRIEF SUMMARY OF THE INVENTION

The present invention is directed to an isolated thraustochytrid microorganism of the thraustochytrid species deposited under ATCC Accession No. PTA-9695 or a strain derived therefrom, wherein the total fatty acids produced by said microorganism or strain derived therefrom comprise about 10% or less by weight eicosapentaenoic acid.

The present invention is also directed to an isolated thraustochytrid microorganism having the characteristics of the thraustochytrid species deposited under ATCC Accession No. PTA-9695, wherein the total fatty acids produced by said microorganism or strain derived therefrom comprise about 10% or less by weight eicosapentaenoic acid.

The present invention is also directed to an isolated thraustochytrid microorganism, or a strain derived therefrom, comprising a triglyceride fraction, wherein the docosahexaenoic acid content of the triglyceride fraction is at least about 40% by weight, wherein the docosapentaenoic acid n-6 content of the triglyceride fraction is from at least about 0.5% by weight to about 6% by weight, and wherein the total fatty acids produced by said microorganism or strain derived therefrom comprise about 10% or less by weight eicosapentaenoic acid.

The present invention is also directed to an isolated thraustochytrid microorganism of the same species as the thraustochytrid deposited under ATCC Accession No. PTA-9695, or a strain derived therefrom, wherein the total fatty acids produced by said microorganism or strain derived therefrom comprise about 10% or less by weight eicosapentaenoic acid.

In some embodiments, the strain derived from the isolated thraustochytrid microorganism of the invention is a mutant strain.

The present invention is also directed to an isolated microorganism deposited under ATCC Accession No. PTA-9695, PTA-9696, PTA-9697, or PTA-9698.

The present invention is also directed to a thraustochytrid biomass comprising any one of the thraustochytrid microorganisms of the invention or mixtures thereof.

The present invention is also directed to an isolated thraustochytrid biomass, wherein at least about 50% by weight of the dry cell weight of the biomass are fatty acids, and wherein at least about 50% by weight of the fatty acids are omega-3 fatty acids. In some embodiments, at least about 50% by weight of the fatty acids is docosahexaenoic acid. The present invention is also directed to an isolated thraustochytrid biomass, wherein at least about 25% by weight of the dry cell weight of the biomass is docosahexaenoic acid.

In some embodiments, the present invention is also directed to an isolated thraustochytrid biomass wherein about 10% or less by weight of the fatty acids is eicosapentaenoic acid, and wherein the weight ratio of docosahexaenoic acid to eicosapentaenoic acid is at least about 5:1.

In some embodiments, the present invention is also directed to an isolated thraustochytrid biomass wherein about 1.5% or less by weight of the fatty acids is arachidonic acid, and wherein the weight ratio of docosahexaenoic acid to arachidonic acid is at least about 20:1.

In some embodiments, the present invention is also directed to an isolated thraustochytrid biomass comprising docosahexaenoic acid and docosapentaenoic acid n-6 in a weight ratio of at least about 10:1.

The present invention is also directed to an isolated thraustochytrid culture comprising any one of the thraustochytrid microorganisms of the invention or mixtures thereof. In some embodiments, the culture comprises at least about 5% dissolved oxygen.

The present invention is also directed to a food product, cosmetic, or pharmaceutical composition for animals or humans comprising any one of the thraustochytrid microorganisms or biomasses of the invention or mixtures thereof.

The present invention is also directed to a microbial oil comprising a triglyceride fraction of at least about 70% by weight, wherein the docosahexaenoic acid content of the triglyceride fraction is at least about 50% by weight, and wherein the docosapentaenoic acid n-6 content of the triglyceride fraction is from about 0.5% by weight to about 6% by weight. In some embodiments, the microbial oil further comprises an arachidonic acid content of the triglyceride fraction of about 1.5% or less by weight.

The present invention is also directed to a microbial oil comprising a triglyceride fraction of at least about 70% by weight, wherein the docosahexaenoic acid content of the triglyceride fraction is at least about 40% by weight, wherein the docosapentaenoic acid n-6 content of the triglyceride fraction is from at least about 0.5% by weight to about 6% by weight, and wherein the ratio of docosahexaenoic acid to docosapentaenoic acid n-6 is greater than about 6:1.

The present invention is also directed to a microbial oil comprising a triglyceride fraction of at least about 70% by weight, wherein the docosahexaenoic acid content of the triglyceride fraction is at least about 60% by weight.

In some embodiments, at least about 20% of the triglycerides in the triglyceride fraction of the microbial oil contain docosahexaenoic acid at two positions in the triglyceride selected from any two of the sn-1, sn-2, and sn-3 positions. In some embodiments, at least about 5% of the triglycerides in the triglyceride fraction of the microbial oil contain docosahexaenoic acid at all three of the sn-1, sn-2, and sn-3 positions in the triglyceride.

In some embodiments, the microbial oil further comprises about 5% or less by weight of heptadecanoic acid.

The present invention is also directed to a food product, cosmetic, or pharmaceutical composition for animals or humans comprising any of the microbial oils of the invention. In some embodiments, the food product is an infant formula. In some embodiments, the infant formula is suitable for premature infants. In some embodiments, the food product is a milk, a beverage, a therapeutic drink, a nutritional drink, or a combination thereof. In some embodiments, the food product is an additive for animal or human food. In some embodiments, the food product is a nutritional supplement. In some embodiments, the food product is an animal feed. In some embodiments, the animal feed is an aquaculture feed. In some embodiments, the animal feed is a domestic animal feed, a zoological animal feed, a work animal feed, a livestock feed, or a combination thereof.

The present invention is also directed to a method for producing a microbial oil comprising omega-3 fatty acids, the method comprising: (a) growing any one of the isolated thraustochytrid microorganisms of the invention or mixtures thereof in a culture to produce a biomass, and (b) extracting an oil comprising omega-3 fatty acids from the biomass. In some embodiments, the culture comprises at least about 5% dissolved oxygen. In some embodiments, the culture pH is maintained at about 6.5 to about 8.5. In some embodiments, the culture temperature is maintained at about 17° C. to about 30° C. In some embodiments, the culture comprises a glucose concentration of about 5 g/L to about 50 g/L.

The present invention is also directed to a method for producing a microbial oil comprising omega-3 fatty acids, the method comprising extracting an oil comprising omega-3 fatty acids from any one of the biomasses of the invention. In some embodiments, the microbial oil is extracted using a hexane extraction process. In some embodiments, the microbial oil is extracted using a solventless extraction process.

In some embodiments, the dry cell weight of the biomass isolated from each liter of any one of the cultures of the invention is at least about 50 g after growing for 7 days at about 17° C. to about 30° C. in a culture medium of about pH 6.5 to about pH 8.0 comprising sources of carbon, nitrogen, and nutrients, and about 950 ppm to about 8500 ppm chloride ions.

In some embodiments, any one of the isolated cultures of the invention has an omega-3 fatty acid productivity of at least about 2 g/L/day after growing for about 7 days at about 17° C. to about 30° C. in a culture medium of about pH 6.5 to about pH 8.0 comprising sources of carbon, nitrogen, and nutrients, and about 950 ppm to about 8500 ppm chloride ions.

The present invention is also directed to a microbial oil produced by a method of the invention.

The present invention is also directed to use of any of the isolated microorganisms, biomasses, or microbial oils of the invention, or mixtures thereof, for the manufacture of a medicament for the treatment of inflammation or a condition related thereto.

The present invention is also directed to use of any of the isolated microorganisms, biomasses, or microbial oils of the invention, or mixtures thereof, for the treatment of inflammation or a condition related thereto.

The present invention is also directed to any of the isolated microorganisms, biomasses, or microbial oils of the invention, or mixtures thereof, for use in the treatment of inflammation or a condition related thereto.

The present invention is also directed to a method for treating inflammation or a condition related thereto in a subject in need thereof, comprising administering to the subject any of the isolated microorganisms, biomasses, or microbial oils of the invention, or mixtures thereof, and a pharmaceutically acceptable carrier.

DETAILED DESCRIPTION OF THE INVENTION

The present invention is directed to isolated thraustochytrid microorganisms, as well as strains and mutants thereof, as well as biomasses, microbial oils, compositions, and cultures thereof. The present invention is also directed to methods of producing microbial oils from the thraustochytrids of the invention, and methods of using the thraustochytrids, biomasses, and microbial oils. The thraustochytrids described herein are highly productive as compared to prior isolates and produce unique fatty acid profiles, characterized in part by high levels of omega-3 fatty acids, in particular high levels of DHA.

Thraustochytrid Microorganisms

The invention is directed to isolated thraustochytrids, including mutants, recombinants, and variants thereof.

In some embodiments, the invention is directed to a thraustochytrid of the species deposited under ATCC Accession No. PTA-9695. The isolated thraustochytrid is also known herein as *Schizochytrium* sp. ATCC PTA-9695. The thraustochytrid associated with ATCC Accession No. PTA-9695 was deposited under the Budapest Treaty on Jan. 7, 2009 at the American Type Culture Collection, Patent Depository, 10801 University Boulevard, Manassas, Va. 20110-2209.

In some embodiments, the invention is directed to an isolated thraustochytrid strain deposited under ATCC Accession No. PTA-9695. In some embodiments, the invention is directed to an isolated thraustochytrid microorganism of the same species as the thraustochytrid deposited under ATCC Accession No. PTA-9695.

In some embodiments, the invention is directed to an isolated thraustochytrid having the characteristics of the species deposited under ATCC Accession No. PTA-9695 or a strain derived therefrom. The characteristics of the thraustochytrid species deposited under ATCC Accession No. PTA-9695 include its growth and phenotypic properties (examples of phenotypic properties include morphological and reproductive properties), its physical and chemical properties (such as dry weights and lipid profiles), and its gene sequences. In some embodiments, the isolated thraustochytrids of the invention have substantially identical phenotypic properties of the thraustochytrid deposited under ATCC Accession No. PTA-9695. In some embodiments, the isolated thraustochytrids of the invention have substantially identical growth properties of the thraustochytrid deposited under ATCC Accession No. PTA-9695.

In some embodiments, the invention is directed to a mutant, variant, or recombinant of an isolated thraustochytrid of the invention, wherein the total fatty acids produced by the mutant, variant, or recombinant comprise about 10% or less by weight eicosapentaenoic acid. Mutant strains can be produced by well-known procedures. Common procedures include irradiation; treatment at high temperatures; and treatment with a mutagen. Variant strains can be other naturally occurring isolates and/or subisolates of the species described herein. Recombinant strains can be produced by any well-known methods in molecular biology for the expression of exogenous genes or the alteration of endogenous gene function or expression. In some embodiments, the mutant, variant, or recombinant strain produces a higher amount of omega-3 fatty acids, including DHA and/or EPA, than the wild-type strain. In some embodiments, the mutant, variant, or recombinant strain produces a lower amount of one or more fatty acids, such as lower amounts of EPA, ARA, DPA n-6, or combinations thereof. In some embodiments, the mutant, variant, or recombinant strain produces a larger dry cell weight per liter of culture than the wild-type strain. Such mutant, variant, or recombinant strains are examples of strains derived from an isolated thraustochytrid of the invention.

In some embodiments, the invention is directed to a mutant strain of the thraustochytrid deposited under ATCC Accession No. PTA-9695. In further embodiments, the mutant strain is a strain deposited under ATCC Accession Nos. PTA-9696, PTA-9697, or PTA-9698. The thraustochytrid strains associated with ATCC Accession Nos. PTA-9696, PTA-9697, and PTA-9698 were deposited under the Budapest Treaty on Jan. 7, 2009 at the American Type Culture Collection, Patent Depository, 10801 University Boulevard, Manassas, Va. 20110-2209. These deposited mutant strains are derivatives of the thraustochytrid deposited under ATCC Accession No. PTA-9695.

In some embodiments, an isolated thraustochytrid of the invention, including mutants, variants, or recombinants thereof, comprises a fatty acid profile in one or more fractions isolated from the thraustochytrid. The one or more fractions isolated from the thraustochytrid includes the total fatty acid fraction, the sterol esters fraction, the triglyceride fraction, the free fatty acid fraction, the sterol fraction, the diglyceride fraction, the polar fraction (including the phospholipid fraction), and combinations thereof.

Thraustochytrid Cultures and Isolated Thraustochytrid Biomasses

The invention is further directed to a culture comprising one or more isolated thraustochytrids of the invention. Various fermentation parameters for inoculating, growing, and recovering microflora are known in the art, such as described in U.S. Pat. No. 5,130,242. Any conventional medium for growth of thraustochytrids can be used. Liquid or solid mediums can contain natural or artificial sea water. Carbon sources include, but are not limited to, glucose, fructose, xylose, saccharose, maltose, soluble starch, molasses, fucose, glucosamine, dextran, fats, oils, glycerol, sodium acetate, and mannitol. Nitrogen sources include, but are not limited to, peptone, yeast extract, polypeptone, malt extract, meat extract, casamino acid, corn steep liquor, organic nitrogen sources, sodium glutamate, urea, inorganic nitrogen sources, ammonium acetate, ammonium sulfate, ammonium chloride, ammonium nitrate, sodium sulfate. A typical media is shown in Table 1:

TABLE 1

Vessel Media

| Ingredient | | concentration | ranges |
|---|---|---|---|
| NaCl | g/L | 12.5 | 0-25, 5-20, or 10-15 |
| KCl | g/L | 1.0 | 0-5, 0.25-3, or 0.5-2 |
| MgSO$_4$•7H$_2$O | g/L | 5.0 | 0-10, 2-8, or 3-6 |
| (NH$_4$)$_2$SO$_4$ | g/L | 0.6 | 0-10, 0.25-5, or 0.5-3 |
| CaCl$_2$ | g/L | 0.29 | 0.1-5, 0.15-3, or 0.2-1 |
| T 154 (yeast extract) | g/L | 6.0 | 0-20, 1-15, or 5-10 |
| KH$_2$PO$_4$ | g/L | 1.2 | 0.1-10, 0.5-5, or 1-3 |
| Post autoclave (Metals) | | | |
| Citric acid | mg/L | 3.5 | 0.1-100, 1-50, or 2-25 |
| FeSO$_4$•7H$_2$O | mg/L | 10.30 | 0.1-100, 1-50, or 5-25 |
| MnCl$_2$•4H$_2$O | mg/L | 3.10 | 0.1-100, 1-50, or 2-25 |
| ZnSO$_4$•7H$_2$O | mg/L | 3.10 | 0.1-100, 1-50, or 2-25 |
| CoCl$_2$•6H$_2$O | mg/L | 0.04 | 0.001-1, 0.005-0.5, or 0.01-0.1 |
| Na$_2$MoO$_4$•2H$_2$O | mg/L | 0.04 | 0.001-1, 0.005-0.5, or 0.01-0.1 |
| CuSO$_4$•5H$_2$O | mg/L | 2.07 | 0.1-100, 0.5-50, or 1-25 |
| NiSO$_4$•6H$_2$O | mg/L | 2.07 | 0.1-100, 0.5-50, or 1-25 |
| Post autoclave (Vitamins) | | | |
| Thiamine** | mg/L | 9.75 | 0.1-100, 1-50, or 5-25 |
| Vitamin B12** | mg/L | 0.16 | 0.1-100, 0.1-10, or 0.1-1 |
| Ca½-pantothenate** | mg/L | 3.33 | 0.1-100, 0.1-50, or 1-10 |
| Post autoclave (Carbon) | | | |
| Glucose | g/L | 30.0 | 5-150, 10-100, or 20-50 |

Nitrogen Feed:

| Ingredient | | Concentration | |
|---|---|---|---|
| NH$_4$OH | mL/L | 21.6 | 0-150, 10-100, or 15-50 |

Typical cultivation conditions would include the following:
pH about 6.5-about 8.5, about 6.5-about 8.0, or about 7.0-about 7.5
temperature: about 17-about 30 degrees Celsius, about 20-about 25 degrees Celsius, or about 22 to about 23 degrees Celsius
dissolved oxygen: about 5-about 100% saturation, about 10-about 80% saturation, or about 20-about 50% saturation
glucose controlled @: about 5-about 50 g/L, about 10-about 40 g/L, or about 20 about 35 g/L.

In some embodiments, the culture medium comprises at least about 5%, at least about 10%, at least about 20%, at least about 30%, at least about 40%, at least about 50%, at least about 60%, at least about 70%, at least about 80%, or at least about 90% dissolved oxygen, as a percentage of saturation level. In some embodiments, the culture medium comprises from about 5% to about 20%, about 5% to about 50%, about 5% to about 100%, about 10% to about 20%, about 10% to about 50%, about 10% to about 100%, about 20% to about 50%, or about 20% to about 100% dissolved oxygen, as a percentage of saturation level.

The invention is further directed to an isolated biomass of a thraustochytrid of the invention. An isolated thraustochytrid biomass of the invention is a harvested cellular biomass obtained by any conventional method for the isolation of a thraustochytrid biomass, such as described in U.S. Pat. No. 5,130,242 and U.S. Appl. Publ. No. 2002/0001833.

In some embodiments, the dry cell weight of the biomass isolated from each liter of culture is at least about 50 g, at least about 60 g, at least about 70 g, at least about 80 g, at least about 100 g, at least about 120 g, at least about 140 g, at least about 160 g, at least about 180 g, or at least about 200 g after growing for about 7 days at about 17° C. to about 30° C. in a culture medium of about pH 6.5 to about 8.5 comprising sources of carbon, nitrogen, and nutrients, and about 950 ppm to about 8500 ppm chloride ions. In some embodiments, the dry cell weight of the biomass isolated from each liter of culture is at least about 50 g, at least about 60 g, at least about 70 g, at least about 80 g, at least about 100 g, at least about 120 g, at least about 140 g, at least about 160 g, at least about 180 g, or at least about 200 g after growing for about 7 days at about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, or about pH 8.5 comprising sources of carbon, nitrogen, and nutrients, and about 950 ppm to about 8500 ppm chloride ions. In some embodiments, the dry cell weight of the biomass isolated from each liter of culture is from about 50 g to about 200 g after growing for about 7 days at about 17° C. to about 30° C. in a culture medium of about pH 6.5 to about pH 8.5 comprising sources of carbon, nitrogen, and nutrients, and about 950 ppm to about 8500 ppm chloride ions. In some embodiments, the dry cell weight of the biomass isolated from each liter of culture is from about 50 g to about 200 g after growing for about 7 days at about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, or about pH 8.5 comprising sources of carbon, nitrogen, and nutrients, and about 950 ppm to about 8500 ppm chloride ions.

In some embodiments, the isolated thraustochytrid culture has an omega-3 fatty acid productivity of at least about 2 g/L/day, at least about 4 g/L/day, or at least about 8 g/L/day after growing for about 7 days at about 17° C. to about 30° C. in a culture medium of about pH 6.5 to about pH 8.5 comprising sources of carbon, nitrogen, and nutrients, and about 950 ppm to about 8500 ppm chloride ions. In some embodiments, the isolated thraustochytrid culture has an omega-3 fatty acid productivity of between about 1 g/L/day to about 20 g/L/day, about 2 g/L/day to about 15 g/L/day, about 2 g/L/day to about 10 g/L/day, about 3 g/L/day to about 10 g/L/day, or about 4 g/L/day to about 9 g/L/day, after growing for about 7 days at about 17° C. to about 30° C. in a culture medium of about pH 6.5 to about pH 8.5 comprising sources of carbon, nitrogen, and nutrients, and about 950 ppm to about 8500 ppm chloride ions.

In some embodiments, the fermentation volume (volume of culture) is at least about 2 liters, at least about 10 liters, at least about 50 liters, at least about 100 liters, at least about 200 liters, at least about 500 liters, at least about 1000 liters, at least about 10,000 liters, at least about 20,000 liters, at least about 50,000 liters, at least about 100,000 liters, at least about 150,000 liters, at least about 200,000 liters, or at least about 250,000 liters. In some embodiments, the fermentation volume is about 2 liters to about 300,000 liters, about 2 liters, about 10 liters, about 50 liters, about 100 liters, about 200 liters, about 500 liters, about 1000 liters, about 10,000 liters, about 20,000 liters, about 50,000 liters, about 100,000 liters, about 150,000 liters, about 200,000 liters, about 250,000 liters, or about 300,000 liters.

In some embodiments, the invention is directed to an isolated thraustochytrid biomass comprising a fatty acid profile of the invention. In some embodiments, at least about 50%, at least about 60%, at least about 70%, or at least about 80% of the dry cell weight of the biomass are fatty acids. In some embodiments, greater than about 50%, greater than about 55%, or greater than about 60% of the dry cell weight of the biomass are fatty acids. In some embodiments, from about 50% to about 60%, about 50% to about 70%, about 50% to about 80%, about 55% to about 70%, about 55% to about 80%, about 60% to about 70%, or about 60% to about 80% by weight of the dry cell weight of the biomass are fatty acids. In some embodiments, the biomass comprises at least about 50%, at least about 60%, at least about 70%, or at least about 80% by weight of the fatty acids as omega-3 fatty acids. In some embodiments, the biomass comprises from about 50% to about 60%, about 50% to about 70%, about 50% to about 80% by weight of the fatty acids as omega-3 fatty acids. In some embodiments, the biomass comprises at least about 50%, at least about 55%, at least about 60%, at least about 65%, at least about 70%, at least about 75%, or at least about 80% by weight of the fatty acids as DHA. In some embodiments, the biomass comprises from about 50% to about 60%, about 50% to about 70%, or about 50% to about 80% by weight of the fatty acids as DHA. In some embodiments, at least about 25%, at least about 30%, at least about 40%, at least about 50%, or at least about 60% by weight of the dry cell weight of the biomass is docosahexaenoic acid. In some embodiments, about 25% to about 65%, about 25% to about 50%, about 30% to about 40%, or about 25% to about 35% by weight of the dry cell weight of the biomass is docosahexaenoic acid. In some embodiments, the biomass comprises about 10% or less, about 9% or less, about 8% or less, about 7% or less, about 6% or less, about 5% or less, about 4% or less, about 3% or less, about 2% or less, or about 1% or less by weight of the fatty acids as EPA. In some embodiments, the biomass comprises from about 1% to about 10%, about 1% to about 5%, about 2% to about 5%, about 3% to about 5%, or about 3% to about 10% by weight of the fatty acids as EPA. In some embodiments, the biomass is substantially free of EPA. In some embodiments, the biomass comprises a weight ratio of DHA to EPA of at least about 5:1, at least about 7:1, at least about 10:1, at least about 11:1, at least about 14:1, at least about 15:1, at least about 17:1, at least about 20:1, at least about 25:1, at least about 50:1, or at least about 100:1, wherein the biomass comprises about 10% or less by weight of the fatty acids as EPA. In some embodiments, the biomass comprises from about 0.1% to 0.2%, about 0.1% to about 0.3%, about 0.1% to about 0.4%, about 0.1% to about 0.5%, or about 0.1% to about 1.5% by weight of the fatty acids as ARA. In some embodiments, the biomass comprises about 1.5% or less, about 1% or less, about 0.5% or less, about 0.4% or less, about 0.3% or less, about 0.2% or less, or about 0.1% or less by weight of the fatty acids as ARA. In some embodiments, the biomass is substantially free of ARA. In some embodiments, the biomass comprises a weight ratio of DHA to ARA of at least about 20:1, at least about 40:1, at least about 60:1, at least about 80:1, at least about 100:1, at least about 150:1, at least about 200:1, at least about 250:1, or at least about 300:1. In some embodiments, the biomass comprises from about 0.5% to about 1%, about 0.5% to about 2%, about 0.5% to about 5%, about 0.5% to about 6%, about 1% to about 5%, about 1% to about 6%, about 2% to about 5%, or about 2% to about 6% by weight of the fatty acids as DPA n-6. In some embodiments, the biomass comprises about 6% or less, about 5% or less, about 2% or less, about 1% or less, or about 0.5% or less by weight of the fatty acids as DPA n-6. In some embodiments, the biomass is substantially free of DPA n-6. In some embodiments, the biomass comprises a weight ratio of DHA to DPA n-6 of greater than about 6:1, at least about 8:1, at least about 10:1, at least about 15:1, at least about 20:1, at least about 25:1, at least about 50:1, or at least about 100:1. In some embodiments, the biomass comprises fatty acids with about 5% or less, about 4% or less, about 3% or less, or about 2% or less by weight each of linoleic acid (18:2 n-6), linolenic acid (18:3 n-3), eicosenoic acid (20:1 n-9), and erucic acid (22:1 n-9).

The characteristics of an isolated biomass of the invention are associated with endogenous or native properties of the isolated biomass rather than exogenously introduced materials.

Microbial Oils

The present invention is further directed to methods of producing microbial oils. In some embodiments, the method comprises growing a thraustochytrid of the invention in a culture to produce a biomass and extracting an oil comprising omega-3 fatty acids from the biomass. The oil can be extracted from a freshly harvested biomass or can be extracted from a previously harvested biomass that has been stored under conditions that prevent spoilage. Known methods can be used to culture a thraustochytrid of the invention, to isolate a biomass from the culture, to extract a microbial oil from the biomass, and to analyze the fatty acid profile of oils extracted from the biomass. See, e.g., U.S. Pat. No. 5,130,242.

The invention is further directed to a microbial oil comprising a fatty acid profile of the invention. A microbial oil of the invention can be any oil derived from a microorganism, including, for example: a crude oil extracted from the biomass of the microorganism without further processing; a refined oil that is obtained by treating a crude microbial oil with further processing steps such as refining, bleaching, and/or deodorizing; a diluted microbial oil obtained by diluting a crude or refined microbial oil; or an enriched oil that is obtained, for example, by treating a crude or refined microbial oil with further methods of purification to increase the concentration of a fatty acid (such as DHA) in the oil.

In some embodiments, the microbial oil comprises a sterol esters fraction of about 0%, at least about 0.1%, at least about 0.2%, at least about 0.5%, at least about 1%, at least about 1.5%, at least about 2%, or at least about 5% by weight. In some embodiments, the microbial oil comprises a sterol esters fraction of from about 0% to about 1.5%, about 0% to about 2%, about 0% to about 5%, about 1% to about 1.5%, about 0.2% to about 1.5%, about 0.2% to about 2%, or about 0.2% to about 5% by weight. In some embodiments, the microbial oil comprises a sterol esters fraction of less than about 5%, less than about 4%, less than about 3%, or less than about 2% by weight. In some embodiments, the microbial oil comprises a triglyceride fraction of at least about 65%, at least about 70%, at least about 75%, at least about 80%, at least about 85%, or at least about 90% by weight. In some embodiments, the microbial oil comprises a triglyceride fraction of from about 65% to about 95%, about 75% to about 95%, or about 80% to about 95% by weight, or about 97% by weight, or about 98% by weight. In some embodiments, the microbial oil comprises a free fatty acid fraction of at least about 0.5%, at least about 1%, at least about 1.5%, at least about 2%, at least about 2.5%, or at least about 5% by weight. In some embodiments, the microbial oil comprises a free fatty acid fraction of from about 0.5% to about 5%, about 0.5% to about 2.5%, about 0.5% to about 2%, about 0.5% to about 1.5%, about 0.5% to about 1%, about 1% to about 2.5%, about 1% to about 5%, about 1.5% to about 2.5%, about 2% to about 2.5%, or about 2% to about 5% by weight. In some embodiments, the microbial oil comprises a free fatty acid fraction of less than about 5%, less than about 4%, less than about 3%, less than about 2%, or less than about 1% by weight. In some embodiments, the microbial oil comprises a sterol fraction of at least about 0.5%, at least about 1%, at least about 1.5%, at least about 2%, or at least about 5% by weight. In some embodiments, the microbial oil comprises a sterol fraction of from about 0.5% to about 1.5%, about 1% to about 1.5%, about 0.5% to about 2%, about 0.5% to about 5%, about 1% to about 2%, or about 1% to about 5% by weight. In some embodiments, the microbial oil comprises a sterol fraction of less than about 5%, less than about 4%, less than about 3%, less than about 2%, or less than about 1% by weight. In some embodiments, the microbial oil comprises a diglyceride fraction of at least about 1.5%, at least about 2%, at least about 2.5%, at least about 3%, at least about 3.5%, or at least about 5% by weight. In some embodiments, the microbial oil comprises a diglyceride fraction of from about 1.5% to about 3%, about 2% to about 3%, about 1.5% to about 3.5%, about 1.5% to about 5%, about 2.5% to about 3%, about 2.5% to about 3.5%, or about 2.5% to about 5% by weight. In some embodiments, the microbial oil comprises unsaponifiables of less than about 2%, less than about 1.5%, less than about 1%, or less than about 0.5% by weight of the oil. The lipid classes present in the microbial oil, such as the triglyceride fraction, can be separated by flash chromatography and analyzed by thin layer chromatography (TLC), or separated and analyzed by other methods know in the art.

In some embodiments, the microbial oil and/or one or more fractions thereof selected from the triglyceride fraction, the free fatty acid fraction, the sterol fraction, the diglyceride fraction, and combinations thereof, comprises at least about 40%, at least about 45%, at least about 50%, at least about 55%, at least about 60%, at least about 65%, at least about 70%, at least about 75%, or at least about 80% by weight DHA. In some embodiments, the microbial oil and/or one or more fractions thereof selected from the triglyceride fraction, the free fatty acid fraction, the sterol fraction, the diglyceride fraction, and combinations thereof, comprises from about 40% to about 45%, about 40% to about 50%, about 40% to about 60%, about 50% to about 60%, about 55% to about 60%, about 40% to about 65%, about 50% to about 65%, about 55% to about 65%, about 40% to about 70%, about 40% to about 80%, about 50% to about 80%, about 55% to about 80%, about 60% to about 80%, or about 70% to about 80% by weight DHA. In some embodiments, the microbial oil comprises a sterol esters fraction comprising about 45% or less, about 40% or less, about 35% or less, about 30% or less, about 25% or less, about 20% or less, about 15% or less, or about 13% or less by weight DHA. In some embodiments, the microbial oil and/or one or more fractions thereof selected from the triglyceride fraction, the free fatty acid fraction, the sterol fraction, the diglyceride fraction, and combinations thereof, comprises about 10% or less, about 9% or less, about 8% or less, about 7% or less, about 6% or less, about 5% or less, about 4% or less, about 3% or less, about 2% or less, or about 1% or less by weight EPA. In some embodiments, the microbial oil and/or one or more fractions thereof selected from the triglyceride fraction, the free fatty acid fraction, the sterol fraction, the diglyceride fraction, and combinations thereof, comprises from about 2% to about 3%, about 2% to about 3.5%, about 2.5% to about 3.5%, about 2% to about 6%, about 2.5% to about 6%, about 3.0% to about 6%, about 3.5% to about 6%, about 5% to about 6%, or about 2% to about 10% by weight EPA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, is substantially free of EPA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises a weight ratio of DHA to EPA of at least about 5:1, at least about 7:1, at least about 9:1, at least about 10:1, at least about 15:1, at least about 20:1, at least about 25:1, at least about 30:1, or at least about 50:1, wherein the microbial oil and/or one or more fractions thereof comprises 10% or less by weight of EPA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises a weight ratio of DHA to EPA of at least about 5:1, but less than about 20:1. In some embodiments, the weight ratio of DHA to EPA is from about 5:1 to about 18:1, from about 7:1 to about 16:1, or from about 10:1 to about 15:1. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof comprises from about 0.1% to about 0.25%, about 0.2% to about 0.25%, about 0.1% to about 0.5%, or about 0.1% to about 1.5% by weight ARA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 1.5% or less, about 1% or less, about 0.5% or less, about 0.2% or less, or about 0.1% or less by weight ARA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, is substantially free of ARA. In some embodiments, the microbial oil and/or one or more fractions thereof selected from the sterol esters fraction, the triglyceride fraction, the free fatty acid fraction, the diglyceride fraction, the polar fraction (including the phospholipid fraction), and combinations thereof, comprises a weight ratio of DHA to ARA of at least about 20:1, at least about 30:1, at least about 35:1, at least about 40:1, at least about 60:1, at least about 80:1, at least about 100:1, at least about 150:1, at least about 200:1, at least about 250:1, or at least about 300:1. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises from about 0.5% to about 1%, about 0.5% to about 2%, about 0.5% to about 2.5%, about 0.5% to about 3%, about 0.5% to about 3.5%, about 0.5% to about 5%, about 0.5% to about 6%, about 1% to about 2%, about 2% to about 3%, about 2% to about 3.5%, about 1% to about 2.5%, about 1% to about 3%, about 1% to about 3.5%, about 1% to about 5%, or about 1% to about 6% by weight DPA n-6. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 6% or less, about 5% or less, about 3% or less, about 2.5% or less, about 2% or less, about 1% or less, or about 0.5% or less by weight DPA n-6. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, is substantially free of DPA n-6. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises a weight ratio of DHA to DPA n-6 of greater than about 6:1, of at least about 8:1, at least about 10:1, at least about 15:1, at least about 20:1, at least about 25:1, at least about 50:1, or at least about 100:1. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 5% or less, about 4% or less, about 3% or less, about 2% or less, about 1.5% or less, about 1% or less, or about 0.5% or less by weight each of linoleic acid (18:2 n-6), linolenic acid (18:3 n-3), eicosenoic acid (20:1 n-9), and erucic acid (22:1 n-9). In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 5% or less, about 4% or less, about 3% or less, about 2% or less, about 1.5% or less, or about 1% or less by weight of heptadecanoic acid (17:0). In some embodiments, the microbial oil and/or one or more fractions thereof comprise about 0.01% to about 5% by weight, about 0.05% to about 3% by weight, or about 0.1% to about 1% by weight of heptadecanoic acid.

The triglyceride molecule contains 3 central carbon atoms ($C_{sn-1}H_2R1$-$C_{sn-2}H_2R2$-$C_{sn-3}H_2R3$), allowing for formation of different positional isomers. In some embodiments, the microbial oil comprises a triglyceride fraction in which at least about 20%, at least about 30%, at least about 35%, or at least about 40% of the triglycerides in the triglyceride fraction contain DHA at two positions in the triglyceride (di-substituted DHA) selected from any two of the sn-1, sn-2, and sn-3 positions, based on the relative area percent of peaks on an HPLC chromatograph. In some embodiments, the microbial oil comprises a triglyceride fraction in which from about 20% to about 40%, about 20% to about 35%, about 30% to about 40%, or about 30% to about 35% of the triglycerides in the triglyceride fraction contain DHA at two positions in the triglyceride selected from any two of the sn-1, sn-2, or sn-3 positions, based on the relative area percent of peaks on an HPLC chromatograph. In some embodiments, the microbial oil comprises a triglyceride fraction in which at least about 5%, at least about 10%, at least about 15%, or at least about 20% of the triglycerides in the triglyceride fraction contain DHA at all of the sn-1, sn-2, and sn-3 positions (tri-substituted DHA), based on the relative area percent of peaks on an HPLC chromatograph. In some embodiments, the microbial oil comprises a triglyceride fraction in which from about 5% to about 20%, about 5% to about 15%, about 10% to about 20%, or about 10% to about 15% of the triglycerides in the triglyceride fraction contain DHA at all of the sn-1, sn-2, and sn-3 positions, based on the relative area percent of peaks on an HPLC chromatograph. In contrast, the TAG species reported in U.S. Pat. No. 6,582,941 does not contain DHA at all three positions. In some embodiments, the microbial oil comprises a triglyceride fraction in which at least about 50%, at least about 55%, at least about 60%, at least about 65%, at least about 70%, or at least about 75% of the triglycerides in the triglyceride fraction contain DHA at one position in the triglyceride selected from any one of the sn-1, sn-2, or sn-3 positions, based on the relative area percent of peaks on an HPLC chromatograph. In some embodiments, the microbial oil comprises a triglyceride fraction in which from about 50% to about 75%, about 50% to about 70%, about 50% to about 65%, about 60% to about 75%, about 60% to about 70%, or about 60% to about 65% of the triglycerides in the triglyceride fraction contain DHA at one position in the triglyceride selected from any one of the sn-1, sn-2, and sn-3 positions, based on the relative area percent of peaks on an HPLC chromatograph.

Compositions

The invention is further directed to compositions comprising a thraustochytrid of the invention, an isolated biomass of the invention, a microbial oil of the invention, or combinations thereof.

A thraustochytrid, biomass, or microbial oil of the invention can be further chemically or physically modified or processed based on the requirements of the composition by any known technique.

Thraustochytrid cells or biomasses can be dried prior to use in a composition by methods including, but not limited to, freeze drying, air drying, spray drying, tunnel drying, vacuum drying (lyophilization), or a similar process. Alternatively, a harvested and washed biomass can be used directly in a composition without drying. See, e.g., U.S. Pat. Nos. 5,130,242 and 6,812,009.

Microbial oils of the invention can be used as starting material to more efficiently produce a product enriched in a fatty acid such as DHA. For example, the microbial oils of the invention can be subjected to various purification techniques known in the art, such as distillation or urea adduction, to produce a higher potency product with higher concentrations of DHA or another fatty acid. The microbial oils of the invention can also be used in chemical reactions to produce compounds derived from fatty acids in the oils, such as esters and salts of DHA or another fatty acid.

A composition of the invention can include one or more excipients. As used herein, "excipient" refers to a component, or mixture of components, that is used in a composition of the present invention to give desirable characteristics to the composition, including foods as well as pharmaceutical, cosmetic, and industrial compositions. An excipient of the present invention can be described as a "pharmaceutically acceptable" excipient when added to a pharmaceutical composition, meaning that the excipient is a compound, material, composition, salt, and/or dosage form which is, within the scope of sound medical judgment, suitable for contact with the tissues of human beings and animals without excessive toxicity, irritation, allergic response, or other problematic complications over the desired duration of contact commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, 21$^{st}$ ed. (2005). Inclusion of an excipient in a particular classification herein (e.g., "solvent") is intended to illustrate rather than limit the role of the excipient. A particular excipient can fall within multiple classifications.

Compositions of the invention include, but are not limited to, food products, pharmaceutical compositions, cosmetics, and industrial compositions.

In some embodiments, the composition is a food product. A food product is any food for animal or human consumption, and includes both solid and liquid compositions. A food product can be an additive to animal or human foods. Foods include, but are not limited to, common foods; liquid products, including milks, beverages, therapeutic drinks, and nutritional drinks; functional foods; supplements; nutraceuticals; infant formulas, including formulas for pre-mature infants; foods for pregnant or nursing women; foods for adults; geriatric foods; and animal foods.

In some embodiments, a thraustochytrid, biomass, or microbial oil of the invention can be used directly as or included as an additive within one or more of: an oil, shortening, spread, other fatty ingredient, beverage, sauce, dairy-based or soy-based food (such as milk, yogurt, cheese and ice-cream), a baked good, a nutritional product, e.g., as a nutritional supplement (in capsule or tablet form), a vitamin supplement, a diet supplement, a powdered drink, a finished or semi-finished powdered food product, and combinations thereof.

A partial list of food compositions that can include a microbial oil of the invention includes, but is not limited to, soya based products (milks, ice creams, yogurts, drinks, creams, spreads, whiteners); soups and soup mixes; doughs, batters, and baked food items including, for example, fine bakery wares, breakfast cereals, cakes, cheesecakes, pies, cupcakes, cookies, bars, breads, rolls, biscuits, muffins, pastries, scones, croutons, crackers, sweet goods, snack cakes, pies, granola/snack bars, and toaster pastries; candy; hard confectionery; chocolate and other confectionery; chewing gum; liquid food products, for example milks, energy drinks, infant formula, carbonated drinks, teas, liquid meals, fruit juices, fruit-based drinks, vegetable-based drinks; multivitamin syrups, meal replacers, medicinal foods, and syrups; powdered beverage mixes; pasta; processed fish products; processed meat products; processed poultry products; gravies and sauces; condiments (ketchup, mayonnaise, etc.); vegetable oil-based spreads; dairy products; yogurt; butters; frozen dairy products; ice creams; frozen desserts; frozen yogurts; semi-solid food products such as baby food; puddings and gelatin desserts; processed and unprocessed cheese; pancake mixes; food bars including energy bars; waffle mixes; salad dressings; replacement egg mixes; nut and nut-based spreads; salted snacks such as potato chips and other chips or crisps, corn chips, tortilla chips, extruded snacks, popcorn, pretzels, potato crisps, and nuts; specialty snacks such as dips, dried fruit snacks, meat snacks, pork rinds, health food bars and rice/corn cakes.

In some embodiments, a microbial oil of the invention can be used to supplement infant formula. Infant formula can be supplemented with a microbial oil of the invention alone or in combination with a physically refined oil derived from an arachidonic acid (ARA)-producing microorganism. An ARA-producing microorganism, for example, is *Mortierella alpina* or *Mortierella* sect. *schmuckeri*. Alternatively, infant formulas can be supplemented with a microbial oil of the invention in combination with an oil rich in ARA, including ARASCO®) (Martek Biosciences, Columbia, Md.).

In some embodiments, the composition is an animal feed. An "animal" means any non-human organism belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. An animal feed includes, but is not limited to, an aquaculture feed, a domestic animal feed including pet feed, a zoological animal feed, a work animal feed, a livestock feed, or a combination thereof.

In some embodiments, the composition is a feed or feed supplement for any animal whose meat or products are consumed by humans, such as any animal from which meat, eggs, or milk is derived for human consumption. When fed to such animals, nutrients such as LC-PUFAs can be incorporated into the flesh, milk, eggs or other products of such animals to increase their content of these nutrients.

In some embodiments, the composition is a spray-dried material that can be crumbled to form particles of an appropriate size for consumption by zooplankton, artemia, rotifers, and filter feeders. In some embodiments, the zooplankton, artemia, or rotifers fed by the composition are in turn fed to fish larvae, fish, shellfish, bivalves, or crustaceans.

In some embodiments, the composition is a pharmaceutical composition. Suitable pharmaceutical compositions include, but are not limited to, an anti-inflammatory composition, a drug for treatment of coronary heart disease, a drug for treatment of arteriosclerosis, a chemotherapeutic agent, an active excipient, an osteoporosis drug, an anti-depressant, an anti-convulsant, an anti-*Helicobacter pylori* drug, a drug for treatment of neurodegenerative disease, a drug for treatment of degenerative liver disease, an antibiotic, a cholesterol lowering composition, and a triglyceride lowering composition. In some embodiments, the composition is a medical food. A medical food includes a food that is in a composition to be consumed or administered externally under the supervision of a physician and that is intended for the specific dietary management of a condition, for which distinctive nutritional requirements, based on recognized scientific principles, are established by medical evaluation.

In some embodiments, the microbial oil can be formulated in a dosage form. Dosage forms can include, but are not limited to, tablets, capsules, cachets, pellets, pills, powders and granules, and parenteral dosage forms, which include, but are not limited to, solutions, suspensions, emulsions, and dry powders comprising an effective amount of the microbial oil. It is also known in the art that such formulations can also contain pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Administration forms can include, but are not limited to, tablets, dragees, capsules, caplets, and pills, which contain the microbial oil and one or more suitable pharmaceutically acceptable carriers.

For oral administration, the microbial oil can be combined with pharmaceutically acceptable carriers well known in the art. Such carriers enable the microbial oils of the invention to be formulated as tablets, pills, dragees, capsules, liquids, gels, syrups, slurries, suspensions and the like, for oral ingestion by a subject to be treated. In some embodiments, the dosage form is a tablet, pill or caplet. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate. Pharmaceutical preparations that can be used orally include, but are not limited to, push-fit capsules made of gelatin, as well as soft, sealed capsules made of gelatin and a plasticizer, such as glycerol or sorbitol.

In some embodiments, the composition is a cosmetic. Cosmetics include, but are not limited to, emulsions, creams, lotions, masks, soaps, shampoos, washes, facial creams, conditioners, make-ups, bath agents, and dispersion liquids. Cosmetic agents can be medicinal or non-medicinal.

In some embodiments, the composition is an industrial composition. In some embodiments, the composition is a starting material for one or more manufactures. A manufacture includes, but is not limited to, a polymer; a photographic photosensitive material; a detergent; an industrial oil; or an industrial detergent. For example, U.S. Pat. No. 7,259,006 describes use of DHA-containing fat and oil for production of behenic acid and production of photographic sensitive materials using behenic acid.

Methods of Using the Compositions

In some embodiments, the compositions can be used in the treatment of a condition in humans or animals.

The terms "treat" and "treatment" refer to both therapeutic treatment and prophylactic or preventative measures, wherein the object is to prevent or slow down (lessen) an undesired physiological condition, disease, or disorder, or to obtain beneficial or desired clinical results. For purposes of this invention, beneficial or desired clinical results include, but are not limited to, alleviation of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a clinically significant response without excessive side effects. Treatment also includes prolonging survival as compared to expected survival if not receiving treatment.

In some embodiments, the composition is used to treat a condition, disease, or disorder such as acne, acute inflammation, age related maculopathy, allergy, Alzheimer's, arthritis, asthma, atherosclerosis, autoimmune disease, blood lipid disorder, breast cysts, cachexia, cancer, cardiac restenosis, cardiovascular diseases, chronic inflammation, coronary heart disease, cystic fibrosis, degenerative disorder of the liver, diabetes, eczema, gastrointestinal disorder, heart disease, high triglyceride levels, hypertension, hyperactivity, immunological diseases, inhibiting tumor growth, inflammatory conditions, intestinal disorders, kidney dysfunction, leukemia, major depression, multiple sclerosis, neurodegenerative disorder, osteoarthritis, osteoporosis, peroxisomal disorder, preeclampsia, preterm birth, psoriasis, pulmonary disorder rheumatoid arthritis, risk of heart disease, or thrombosis.

In some embodiments, the composition is used to increase the length of gestation in the third trimester.

In some embodiments, the composition is used to control blood pressure.

In some embodiments, the composition is used to improve or maintain cognitive function.

In some embodiments, the composition is used to improve or maintain memory.

The composition or dosage form can be administered into the body of a subject by any route compatible with the composition or dosage form. A substance is considered to be "administered" if the substance is introduced into the body of the subject by the subject, or if another person, a machine, or a device introduces the substance into the body of the subject. "Administering," therefore, includes, e.g., self-administration, administration by others, and indirect administration. The term "continuous" or "consecutive," as used herein in reference to "administration," means that the frequency of administration is at least once daily. Note, however, that the frequency of administration can be greater than once daily and still be "continuous" or "consecutive," e.g., twice or even three times daily, as long as the dosage levels as specified herein are not exceeded. The means and methods for administration are known in the art and an artisan can refer to various pharmacologic references for guidance. For example, "Modern Pharmaceutics," Banker & Rhodes, Informa Healthcare, USA, 4th ed. (2002); and "Goodman & Gilman's The Pharmaceutical Basis of Therapeutics," McGraw-Hill Companies, Inc., New York, 10th ed. (2001) can be consulted.

By "subject," "individual," or "patient" is meant any subject, whether human or non-human, for whom diagnosis, prognosis, or therapy is desired. Mammalian subjects include, but are not limited to, humans; domestic animals; farm animals; zoo animals; sport animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. The term subject also encompasses model animals, e.g., disease model animals. In some embodiments, the term subject includes valuable animals, either economically or otherwise, e.g., economically important breeding stock, racing animals, show animals, heirloom animals, rare or endangered animals, or companion animals. In certain embodiments, the subject is a human subject. In certain embodiments, the subject is a non-human subject.

The composition can be administered as a "therapeutically effective amount," a "prophylactically effective amount," a "therapeutic dose," or a "prophylactic dose." A "therapeutically effective amount" or "therapeutic dose" refers to an amount effective, at dosages and for periods of time necessary, to achieve a desired therapeutic result. A therapeutic result can be, e.g., lessening of symptoms, prolonged survival, improved mobility, and the like. A therapeutic result need not be a "cure." A "prophylactically effective amount" or "prophylactic dose" refers to an amount effective, at dosages and for periods of time necessary, to achieve the desired prophylactic result. Typically, since a prophylactic dose is used in subjects prior to or at an earlier stage of disease, a prophylactically effective amount will be less than a therapeutically effective amount for treatment of an advanced stage of disease.

Various dosage amounts of the pharmaceutical composition can be administered to a subject, based on the amount of DHA or other fatty acid component of the thraustochytrid, biomass, or microbial oil to be administered to the subject. The terms "daily dosage," "daily dosage level," and "daily dosage amount" refer herein to the total amount of DHA or other fatty acid component administered per day (per 24 hour period). Thus, for example, administration of DHA to a subject at a daily dosage of 2 mg means that the subject receives a total of 2 mg of DHA on a daily basis, whether the DHA is administered as a single dosage form comprising 2 mg DHA, or alternatively, four dosage forms comprising 0.5 mg DHA each (for a total of 2 mg DHA). In some embodiments, the daily amount of DHA is administered in a single dosage form, or in two dosage forms. The dosage forms of the present invention can be taken in a single application or multiple applications. For example, if four tablets are taken daily, each tablet comprising 0.5 mg DHA, then all four tablets can be taken once daily, or 2 tablets can be taken twice daily, or 1 tablet can be taken every 6 hours. In some embodiments, the daily dosage is from about 100 mg to about 15 g of DHA. In some embodiments, the daily dosage is from about 100 mg to about 250 mg, about 100 mg to about 500 mg, about 100 mg to about 1 g, about 1 g to about 2.5 g, about 1 g to about 5 g, about 1 g to about 10 g, about 1 g to about 15 g, about 5 g to about 10 g, about 5 g to about 15 g, about 10 g to about 15 g, about 100 mg to about 10 g, about 100 mg to about 5 g, or about 100 mg to about 2.5 g.

Administration of the compositions or dosage forms of the present invention can be achieved using various regimens. For example, in some embodiments, administration occurs daily on consecutive days, or alternatively, occurs every other day (bi-daily). Administration can occur on one or more days.

Administration of the compositions and dosage forms can be combined with other regimens used for treatment of the condition. For example, the method of the present invention can be combined with diet regimens (e.g., low carbohydrate diets, high protein diets, high fiber diets, etc.), exercise regimens, weight loss regimens, smoking cessation regimens, or combinations thereof. The method of the present invention can also be used in combination with other pharmaceutical products in the treatment of the condition. The compositions or dosage forms of the present invention can be administered before or after other regimens or pharmaceutical products.

Kits Comprising the Compositions

The invention is further directed to kits or packages containing one or more units of a composition of the invention. Kits or packages can include units of a food product, pharmaceutical composition, cosmetic, or industrial composition comprising the thraustochytrid, biomass, or microbial oil of the invention, or combinations thereof. Kits or packages can also include an additive comprising the thraustochytrid, biomass, or microbial oil of the invention, or combinations thereof for preparation of a food, cosmetic, pharmaceutical composition, or industrial composition.

In some embodiments, the kit or package contains one or more units of a pharmaceutical composition to be administered according to the methods of the present invention. The kit or package can contain one dosage unit, or more than one dosage unit (i.e., multiple dosage units). If multiple dosage units are present in the kit or package, the multiple dosage units can be optionally arranged for sequential administration.

The kits of the present invention can optionally contain instructions associated with the units or dosage forms of the kits. Such instructions can be in a form prescribed by a governmental agency regulating the manufacture, use or sale of pharmaceutical products, which notice reflects approval by the agency of the manufacture, use or sale for human administration to treat a condition or disorder. The instructions can be in any form which conveys information on the use of the units or dosage forms in the kit according to the methods of the invention. For example, the instructions can be in the form of printed matter, or in the form of a pre-recorded media device.

In the course of examination of a patient, a medical professional can determine that administration of one of the methods of the present invention is appropriate for the patient, or the physician can determine that the patient's condition can be improved by the administration of one of the methods of the present invention. Prior to prescribing any regimen, the physician can counsel the patient, for example, on the various risks and benefits associated with the regimen. The patient can be provided full disclosure of all known and suspected risks associated with the regimen. Such counseling can be provided verbally, as well as in written form. In some embodiments, the physician can provide the patient with literature materials on the regimen, such as product information, educational materials, and the like.

The present invention is also directed to methods of educating consumers about the methods of treatment, the method comprising distributing the dosage forms with consumer information at a point of sale. In some embodiments, the distribution will occur at a point of sale having a pharmacist or healthcare provider.

The term "consumer information" can include, but is not limited to, an English language text, non-English language text, visual image, chart, telephone recording, website, and access to a live customer service representative. In some embodiments, consumer information will provide directions for use of the dosage forms according to the methods of the present invention, appropriate age use, indication, contraindications, appropriate dosing, warnings, telephone number of website address. In some embodiments, the method further comprises providing professional information to relevant persons in a position to answer consumer questions regarding use of the disclosed regimens according to the methods of the present invention. The term "professional information" includes, but is not limited to, information concerning the regimen when administered according to the methods of the present invention that is designed to enable a medical professional to answer costumer questions.

A "medical professional," includes, for example, a physician, physician assistant, nurse practitioner, pharmacist and customer service representative.

Having generally described this invention, a further understanding can be obtained by reference to the examples provided herein. These examples are for purposes of illustration only and are not intended to be limiting.

Example 1

The isolated thraustochytrid deposited under ATCC Accession No. PTA-9695 was characterized for taxonomic classification.

Samples were collected from intertidal habitats during low tide. Water, sediment, living plant material and decaying plant/animal debris were placed into sterile 50 ml tubes. Portions of each sample along with the water were spread onto solid agar plates of isolation media. Isolation media consisted of: 500 ml of artificial seawater, 500 ml of distilled water, 1 g of glucose, 1 g of glycerol, 13 g of agar, 1 g of glutamate, 0.5 g of yeast extract, 0.5 g casein hydrolysate, 1 ml of a vitamin solution (100 mg/L thiamine, 0.5 mg/L biotin, 0.5 mg $B_{12}$), 1 ml of a trace mineral solution (PII metals, containing per liter: 6.0 g $FeCl_36H_2O$, 6.84 g $H_3BO_3$, 0.86 g $MnCl_24H_2O$, 0.06 g $ZnCl_2$, 0.026 $CoCl_26H_2O$, 0.052 g $NiSO_4H_2O$, 0.002 g $CuSO_45H_2O$ and 0.005 g $Na_2MoO_42H_2O$), and 500 mg each of penicillin G and streptomycin sulfate. The agar plates were incubated in the dark at 20-25° C. After 2-4 days the agar plates were examined under magnification, and colonies of cells were picked with a sterile toothpick and restreaked onto a fresh plate of media. Cells were repeatedly streaked onto fresh media until contaminated organisms were removed.

Colonies from agar plates were transferred to petri dishes with half-strength seawater and (1 ml) of a suspension of autoclaved newly hatched brine shrimp larvae. The brine shrimp larvae became heavily overgrown with clusters of sporangia after 2-3 days. Released zoospores were biflagellate at discharge, swimming actively away from the mature sporangium, wall remnants of which are clearly visible (in phase contrast) after spore release. Sporangia measured 12.5 μm to 25 μm in diameter, and zoospores were 2.5 μm to 2.8 μm×4.5 μm to 4.8 μm in size. There were 8 to 24 spores per individual sporangium. Settled zoospores enlarged and rapidly underwent binary divisions leading to tetrads, octads, and finally to clusters of sporangia. Tetrad formation commenced at a very early stage prior to maturity of the sporangia. These characteristics are in agreement with the genus *Schizochytrium*.

The isolated thraustochytrid deposited under ATCC Accession No. PTA-9695 was further characterized based on the similarity of its 18s rRNA gene to that of known species. Total genomic DNA from the thraustochytrid deposited under ATCC Accession No. PTA-9695 was prepared by standard procedures (Sambrook J. and Russell D. 2001. Molecular cloning A laboratory manual, 3rd edition. Cold Spring Harbor Laboratory Press, Cold Spring Harbor, N.Y.) and used for PCR amplification of the 18s RNA gene. The PCR amplification of the 18s rRNA gene was carried out with primers previously described (Honda et. al., *J. Eukaryot. Microbiol.* 46(6) 1999). The PCR conditions with chromosomal DNA template were as follows: 0.2 μM dNTPs, 0.1 uM each primer, 8% DMSO, 200 ng chromosomal DNA, 2.5 U PfuUltra® II fusion HS DNA polymerase (Stratagene), and 1× PfuUltra® buffer (Stratagene) in a 50 μL total volume. The PCR Protocol included the following steps: (1) 95° C. for 2 minutes; (2) 95° C. for 45 seconds; (3) 55° C. for 30 seconds; (4) 72° C. for 2 minutes; (5) repeat steps 2-4 for 40 cycles; (6) 72° C. for 5 minutes; and (7) hold at 6° C.

PCR amplification yielded a distinct DNA product with the expected size using chromosomal template described above. The PCR product was cloned into the vector pJET1.2/blunt (Fermentas) according to the manufacturer's instructions, and the insert sequence was determined using supplied standard primers.

Table 2 shows a comparison of the 18s rRNA sequence from the thraustochytrid deposited under ATCC Accession No. PTA-9695 to DNA sequences in the National Center for Biotechnology Information (NCBI) electronic database. Briefly, "% Identity" was determined by the scoring matrix "swgapdnamt" within the "AlignX" program of the VectorNTI program (Invitrogen), a standard for DNA alignment. The "% Coverage" was taken from the results of a Basic Local Alignment Search Tool (BLAST) calculation from the NCBI electronic database and is the percent of the query length that is included in the aligned segments.

TABLE 2

Comparison of 18s rRNA Sequences

| Thraustochytrids | % Identity Calculation #1 | % Coverage Calculation #2 |
| --- | --- | --- |
| *Thraustochytrium aggregatum* (p) | 98 | 90 |
| *Thraustochutriidae* sp. HU1 | 84 | 86 |
| *Thraustochutriidae* sp. 8-7 | 84 | 91 |
| *Thraustochytrium multirudimentale* | 81 | 88 |
| *Thraustochutriidae* sp. PW19 | 81 | 85 |
| *Schizochytrium* sp. ATCC 20888 | 81 | 95 |

(p): indicates partial sequence

As shown in Table 2, it was found that, in terms of % identity, the 18s rRNA gene sequence (SEQ ID NO: 1) from the thraustochytrid deposited under ATCC Accession No. PTA-9695 is closely related, though not identical, to the 18s rRNA gene sequence of *T. aggregatum* provided in Honda, D. et al., *J. Euk. Micro.* 46(6): 637-647 (1999). The 18s rRNA sequence published for *Thraustochytrium aggregatum* is a partial sequence, with an approximately 71 DNA nucleotide gap in the middle of the sequence. In terms of percent coverage, the 18s rRNA gene sequence of the isolate of the invention is more closely related to *Schizochytrium* sp. ATCC 20888 than to *T. aggregatum*.

Highly conserved proteins such as actin and beta-tubulin have been widely used, along with 18s rRNA gene, as markers for assessing phylogenetic relationships between organisms (Baldauf, S. M. *Am. Nat.* 154, 5178 (1999)). Total genomic DNA from the thraustochytrid deposited under ATCC Accession No. PTA-9695 was also used as a template for PCR amplification of both the actin and beta-tubulin genes. The PCR amplification was carried out with primers designed to conserved regions from the actin and beta-tubulin DNA sequences from *T. aggregatum*.

The PCR conditions with chromosomal DNA template were as follows: 0.2 μM dNTPs, 0.1 uM each primer, 8% DMSO, 200 ng chromosomal DNA, 2.5 U Herculase® II fusion DNA polymerase (Stratagene), and 1× Herculase® buffer (Stratagene) in a 50 μL total volume. The PCR Protocol included the following steps: (1) 95° C. for 2 minutes; (2) 95° C. for 30 seconds; (3) 55° C. for 30 seconds; (4) 72° C. for 2 minutes; (5) repeat steps 2-4 for 40 cycles; (6) 72° C. for 5 minutes; and (7) hold at 6° C.

PCR amplification yielded distinct DNA products with the expected sizes using chromosomal template described above. The respective PCR products were cloned into the vector pJET1.2/blunt (Fermentas) according to the manufacturer's instructions, and the insert sequence of each were determined using supplied standard primers.

Table 3 shows identities for the actin amino acid sequence (SEQ ID NO: 3) from the thraustochytrid deposited under ATCC Accession No. PTA-9695 as compared to actin sequences available in the public database. Identities were determined through use of the scoring matrix "blosum62mt2" within the "AlignX" program of the VectorNTI program, a standard for protein alignment.

TABLE 3

Comparison of Actin Protein Sequence % Identities

| Thraustochytrids | % Identity |
| --- | --- |
| *Thraustochytriidae* sp. RT49 | 98 |
| *Schizochytrium* sp. ATCC 20888 | 96 |
| *Thraustochytrium striatum* | 96 |
| *Thraustochytrium aggregatum* | 96 |
| *Japonochytrium marinum* | 95 |
| *Thraustochytrium aureum* | 95 |

Table 4 shows identities for the beta-tubulin amino acid sequence (SEQ ID NO: 5) from the thraustochytrid deposited under ATCC Accession No. PTA-9695 as compared to beta-tubulin sequences available in the public database. Identities were determined through use of the scoring matrix "blosum62mt2" within the "AlignX" program of the VectorNTI program, a standard for protein alignment.

TABLE 4

Comparison of Beta-Tubulin Protein Sequence % Identities

| Thraustochytrids | % Identity |
| --- | --- |
| *Aplanochytrium kerguelense* | 100 |
| *Aplanochytrium stocchinoi* | 100 |
| *Japonochytrium marinum* | 100 |
| *Labyrinthula* sp. N8 | 100 |
| *Thraustochytriidae* sp. RT49 | 100 |
| *Thraustochytrium aggregatum* | 100 |
| *Thraustochytriidae* sp. HU1 | 100 |
| *Thraustochytrium aureum* | 100 |
| *Thraustochytrium kinnei* | 100 |
| *Thraustochytriidae* sp. #32 | 100 |
| *Thraustochytriidae* sp. PW19 | 100 |
| *Schizochytrium aggregatum* | 100 |
| *Schizochytrium* sp. ATCC 20888 | 100 |

Based on the above characterizations, the isolated thraustochytrid deposited under ATCC Accession No. PTA-9695 is believed to represent a new *Schizochytrium* species and is therefore also designated as *Schizochytrium* sp. ATCC PTA-9695.

Example 2

The isolated thraustochytrid deposited under ATCC Accession No. PTA-9695 produced high levels of cell growth under varying culture conditions, as described below. Typical media and cultivation conditions are shown in Table 1. Also, high levels of fatty acids and DHA were observed (i.e., greater than 50% by weight of the dry cell weight were fatty acids and greater than 50% by weight of the fatty acid methyl esters was DHA).

In carbon and nitrogen-fed cultures with 8200 ppm Cl$^-$ at 22.5° C. with 20% dissolved oxygen at pH 7.0, the isolate produced a dry cell weight of 140 g/L after 7 days of culture, with a fatty acid content of 70% by weight. Closed loop ammonia feed was used and the pH was maintained at 7.0. The omega-3 productivity was 8.92 g/(L*day) under these conditions, with 4.7 g/L EPA (5% by weight of fatty acids) and 56.3 g/L DHA (57% by weight of fatty acids) in 7 days.

In carbon and nitrogen-fed cultures with 3640 ppm Cl$^-$ at 22.5° C. with 20% dissolved oxygen at pH 7.0, the isolate produced a dry cell weight of 82 g/L after 7 days of culture, with a fatty acid content of 58% by weight. The omega-3 productivity was 4.5 g/(L*day) under these conditions, with 2.1 g/L EPA (4.3% by weight of fatty acids) and 28.5 g/L DHA (58.7% by weight of fatty acids) in 7 days.

In carbon and nitrogen-fed cultures with 980 ppm Cl$^-$ at 22.5° C. with 20% dissolved oxygen at pH 7.0, the isolate produced a dry cell weight of 60 g/L after 7 days of culture, with a fatty acid content of 53% by weight. The omega-3 productivity was 2.8 g/(L*day) under these conditions, with 1.1 g/L EPA (3.4% by weight of fatty acids) and 18.4 g/L DHA (56.8% by weight of fatty acids) in 7 days.

Example 3

Oils were extracted from a biomass sample (Sample A) of the isolated thraustochytrid deposited under ATCC Accession No. PTA-9695. The biomass sample was produced in a carbon and nitrogen-fed culture with 980 ppm Cl$^-$ at 22.5° C. with 20% dissolved oxygen at pH 7.0. Oils were extracted from biomass Sample A by the hexane extraction process to yield microbial oil Sample A1. Briefly, dried biomass was ground with hexane using stainless steel tubes and stainless steel ball bearings for approximately 2 hours. The slurry was vacuum filtered and the filtrate was collected. The hexane was removed using a rotary evaporator. Oils were also extracted from biomass Sample A using the FRIOLEX® process (GEA Westfalia Separator UK Ltd., Milton Keynes, England) to yield microbial oil Sample A2. Individual lipid classes were isolated from microbial oil Samples A1 and A2 using low pressure flash chromatography, and the weight percent of each class was determined. The fatty acid profile of each class was determined using gas chromatography with flame ionization detection (GC-FID) as fatty acid methyl esters (FAME).

Flash Chromatography—

Flash chromatography was used to separate the lipid classes present in the crude oils, and to determine the weight percent of each class present in the oils. The chromatography system utilized Silica Gel 60 (EMD Chemical, Gibbstown, N.J.) with mobile phase composed of Petroleum Ether and Ethyl Acetate at 3 mL/min. A step gradient was used to selectively elute each lipid class from the column. The mobile phase gradient started from 100% petroleum ether and finished with 50% ethyl acetate (followed by a 100% methanol wash). Fractions were collected in 10 mL test tubes using a Gilson FC 204 large-bed fraction collector (Gilson, Inc., Middleton, Wis.). Each tube was analyzed by thin layer chromatography (TLC) and the tubes containing individual lipid classes (as judged by single spots on TLC plate with expected retention factor (Rf)) were pooled, concentrated to dryness, and weighed. The total fraction content was then determined gravimetrically.

TLC Analysis—

Thin layer chromatography was conducted on silica gel plates. The plates were eluted using a solvent system consisting of petroleum ether:ethyl ether:acetic acid (80:20:1)

and were visualized using iodine vapor. The Rf values of each spot were then compared with reported literature values for each lipid class.

Fatty Acid Analysis—

The samples of biomass and isolated lipid classes were analyzed for fatty acid composition as FAMEs. Samples were weighed directly into screw cap test tubes, and 1 mL of C19:0 internal standard (NuCheck, Elysian, Minn.) in toluene and 2 mL of 1.5 N HCl in methanol was added to each tube. The tubes were vortexed briefly and placed in a heating block for 2 hours at 100° C. The tubes were removed from the heating block, allowed to cool, and 1 mL of saturated NaCl in water was added. The tubes were vortexed again, centrifuged, and a portion of the top (organic) layer was placed in a GC vial and analyzed by GC-FID. FAME's were quantified using a 3-point internal standard calibration curve generated using Nu-Chek-Prep GLC reference standard (Nu-Chek Prep, Inc., Elysian, Minn.) and tentatively identified based on retention time. Fatty acids present were expressed as mg/g and % of total FAME.

Sample A1 was prepared by dissolving the crude oil in hexane and applying to the head of the column. After fractionation of the sample using flash chromatography, the sterol ester fraction accounted for 1.2% by weight, the triacylglycerol (TAG) fraction accounted for 82.7% by weight, the free fatty acid (FFA) fraction accounted for 0.9% by weight, and the diacylglycerol (DAG) fraction accounted for 2.9% by weight of the crude oil. The total fatty acid profiles of the Sample A1 crude oil and isolated fractions are shown below in Table 5 and Table 6 calculated as mg/g and % FAME, respectively.

TABLE 5

Sample A1 Fatty Acid Profiles Calculated as Milligrams per Gram FAME

| Fatty Acid | Bio-mass FAME (mg/g) | Crude Oil FAME (mg/g) | Sterol Esters FAME (mg/g) | TAG FAME (mg/g) | FFA FAME (mg/g) | DAG FAME (mg/g) |
|---|---|---|---|---|---|---|
| Wt. % | NA | 38% | 1.2% | 82.7% | 0.9 | 2.9% |
| C12:0* | 0.6 | 0.0 | 1.9 | 3.2 | 1.7 | 0.0 |
| C14:0* | 5.7 | 13.6 | 12.8 | 20.2 | 13.0 | 17.6 |
| C14:1* | 0.0 | 0.0 | 0.0 | 0.0 | 0.0 | 0.0 |
| C15:0 | 1.3 | 3.4 | 3.1 | 3.1 | 2.1 | 2.6 |
| C16:0* | 105.5 | 239.5 | 222.2 | 274.3 | 183.3 | 225.1 |
| C16:1* | 0.0 | 0.0 | 0.8 | 0.0 | 0.8 | 0.0 |
| C18:0* | 6.4 | 16.4 | 43.1 | 16.8 | 9.8 | 14.0 |
| C18:1 N9* | 0.0 | 3.8 | 1.9 | 3.3 | 1.0 | 3.5 |
| C18:1 N7 | 0.0 | 0.0 | 0.0 | 0.0 | 0.0 | 0.0 |
| C18:2 N6* | 0.0 | 0.0 | 0.0 | 0.0 | 0.0 | 0.0 |
| C20:0* | 1.8 | 5.5 | 13.0 | 4.7 | 2.0 | 2.9 |
| C18:3 N3* | 0.0 | 0.0 | 0.0 | 0.0 | 0.0 | 0.0 |
| C20:1 N9* | 0.0 | 0.0 | 0.0 | 0.0 | 0.0 | 0.0 |
| C18:4 N3 | 0.0 | 0.0 | 0.0 | 0.0 | 0.6 | 0.0 |
| C20:2 N6* | 0.0 | 0.0 | 0.0 | 0.0 | 0.0 | 0.0 |
| C20:3 N6 | 0.0 | 0.0 | 0.0 | 0.0 | 0.0 | 0.0 |
| C22:0* | 0.0 | 0.8 | 7.3 | 0.8 | 0.0 | 1.2 |
| C20:4 N7 | 0.0 | 0.0 | 0.8 | 0.0 | 0.0 | 0.0 |
| C20:3 N3 | 0.0 | 0.0 | 0.0 | 0.0 | 0.0 | 0.0 |
| C20:4N6* | 1.0 | 3.4 | 0.0 | 2.6 | 2.0 | 1.9 |
| C22:1 N9* | 0.0 | 0.0 | 0.0 | 0.0 | 0.0 | 0.0 |
| C20:4 N5 | 0.0 | 0.0 | 0.0 | 0.0 | 0.0 | 0.0 |
| C20:4 N3 | 1.5 | 4.1 | 1.5 | 3.5 | 2.1 | 2.1 |
| C20:5 N3* | 18.2 | 39.5 | 3.5 | 38.4 | 30.6 | 42.8 |
| C24:0* | 0.0 | 0.0 | 6.3 | 0.0 | 0.0 | 0.0 |
| C22:4 N9 | 0.0 | 0.0 | 0.0 | 0.0 | 0.0 | 0.0 |
| C24:1 N9* | 0.0 | 0.0 | 0.0 | 0.0 | 0.0 | 0.0 |

TABLE 5-continued

Sample A1 Fatty Acid Profiles Calculated as Milligrams per Gram FAME

| Fatty Acid | Bio-mass FAME (mg/g) | Crude Oil FAME (mg/g) | Sterol Esters FAME (mg/g) | TAG FAME (mg/g) | FFA FAME (mg/g) | DAG FAME (mg/g) |
|---|---|---|---|---|---|---|
| Wt. % | NA | 38% | 1.2% | 82.7% | 0.9 | 2.9% |
| C22:5 N6* | 11.9 | 29.5 | 8.9 | 26.9 | 14.8 | 18.7 |
| C22:5 N3* | 1.1 | 4.7 | 0.9 | 3.6 | 3.4 | 2.7 |
| C22:6 N3* | 253.5 | 569.7 | 107.3 | 556.5 | 352.8 | 451.4 |
| Sum of all FAME'S | 408.6 | 934.0 | 435.4 | 958.0 | 620.1 | 786.4 |

TABLE 6

Sample A1 Fatty Acid Profiles as a Percent of Total FAME

| Fatty Acid | Bio-mass % FAME | Crude Oil % FAME | Sterol Esters % FAME | TAG % FAME | FFA % FAME | DAG % FAME |
|---|---|---|---|---|---|---|
| C12:0* | 0.1 | 0.0 | 0.4 | 0.3 | 0.3 | 0.0 |
| C14:0* | 1.4 | 1.5 | 2.9 | 2.1 | 2.1 | 2.2 |
| C14:1* | 0.0 | 0.0 | 0.0 | 0.0 | 0.0 | 0.0 |
| C15:0 | 0.3 | 0.4 | 0.7 | 0.3 | 0.3 | 0.3 |
| C16:0* | 25.8 | 25.6 | 51.0 | 28.6 | 29.6 | 28.6 |
| C16:1* | 0.0 | 0.0 | 0.2 | 0.0 | 0.1 | 0.0 |
| C18:0* | 1.6 | 1.8 | 9.9 | 1.8 | 1.6 | 1.8 |
| C18:1 N9* | 0.0 | 0.4 | 0.4 | 0.3 | 0.2 | 0.4 |
| C18:1 N7 | 0.0 | 0.0 | 0.0 | 0.0 | 0.0 | 0.0 |
| C18:2 N6* | 0.0 | 0.0 | 0.0 | 0.0 | 0.0 | 0.0 |
| C20:0* | 0.4 | 0.6 | 3.0 | 0.5 | 0.3 | 0.4 |
| C18:3 N3* | 0.0 | 0.0 | 0.0 | 0.0 | 0.0 | 0.0 |
| C20:1 N9* | 0.0 | 0.0 | 0.0 | 0.0 | 0.0 | 0.0 |
| C18:4 N3 | 0.0 | 0.0 | 0.0 | 0.0 | 0.1 | 0.0 |
| C20:2 N6* | 0.0 | 0.0 | 0.0 | 0.0 | 0.0 | 0.0 |
| C20:3 N6 | 0.0 | 0.0 | 0.0 | 0.0 | 0.0 | 0.0 |
| C22:0* | 0.0 | 0.1 | 1.7 | 0.1 | 0.0 | 0.1 |
| C20:4 N7 | 0.0 | 0.0 | 0.2 | 0.0 | 0.0 | 0.0 |
| C20:3 N3 | 0.0 | 0.0 | 0.0 | 0.0 | 0.0 | 0.0 |
| C20:4N6* | 0.3 | 0.4 | 0.0 | 0.3 | 0.3 | 0.2 |
| C22:1 N9* | 0.0 | 0.0 | 0.0 | 0.0 | 0.0 | 0.0 |
| C20:4 N5 | 0.0 | 0.0 | 0.0 | 0.0 | 0.0 | 0.0 |
| C20:4 N3 | 0.4 | 0.4 | 0.4 | 0.4 | 0.3 | 0.3 |
| C20:5 N3* | 4.5 | 4.2 | 0.8 | 4.0 | 4.9 | 5.4 |
| C24:0* | 0.0 | 0.0 | 1.4 | 0.0 | 0.0 | 0.0 |
| C22:4 N9 | 0.0 | 0.0 | 0.0 | 0.0 | 0.0 | 0.0 |
| C24:1 N9* | 0.0 | 0.0 | 0.0 | 0.0 | 0.0 | 0.0 |
| C22:5 N6* | 2.9 | 3.2 | 2.1 | 2.8 | 2.4 | 2.4 |
| C22:5 N3* | 0.3 | 0.5 | 0.2 | 0.4 | 0.5 | 0.3 |
| C22:6 N3* | 62.0 | 61.0 | 24.6 | 58.1 | 56.9 | 57.4 |
| Sum of FAME % | 100.0 | 100.0 | 100.0 | 100.0 | 100.0 | 100.0 |

Sample A2 was prepared by dissolving the crude oil in hexane and applying to the head of the column. After fractionation of the sample using flash chromatography, the sterol ester fraction accounted for 0.8% by weight, the triacylglycerol (TAG) fraction accounted for 83A % by weight, the free fatty acid (FFA) fraction accounted for 1.8% by weight, and the diacylglycerol (DAG) fraction accounted for 5.6% by weight of the crude oil. The total fatty acid profiles of the Sample A2 crude oil and isolated fractions are shown below in Table 7 and Table 8 calculated as mg/g and % FAME, respectively.

TABLE 7

Sample A2 Fatty Acid Profiles Calculated as Milligrams per Gram FAME

| | Bio-mass | Crude Oil | Sterol Esters | TAG | FFA | DAG |
|---|---|---|---|---|---|---|
| | | | | Wt. % | | |
| | NA | NA | 0.8% | 83.4% | 1.8% | 5.6% |
| Fatty Acid | FAME (mg/g) | FAME (mg/g) | FAME (mg/g) | FAME (mg/g) | FAME (mg/g) | FAME (mg/g) |
| C12:0* | 0.6 | 0.0 | 0.0 | 1.5 | 0.0 | 1.0 |
| C14:0* | 5.7 | 13.2 | 8.9 | 14.1 | 9.5 | 5.4 |
| C14:1* | 0.0 | 0.0 | 0.0 | 0.0 | 0.0 | 0.0 |
| C15:0 | 1.3 | 3.3 | 2.8 | 3.4 | 2.1 | 2.2 |
| C16:0* | 105.5 | 233.7 | 183.8 | 246.1 | 159.7 | 137.3 |
| C16:1* | 0.0 | 0.0 | 0.0 | 0.8 | 0.0 | 0.0 |
| C18:0* | 6.4 | 16.6 | 23.6 | 16.9 | 11.3 | 5.6 |
| C18:1 N9* | 0.0 | 7.6 | 5.0 | 4.3 | 2.4 | 2.6 |
| C18:1 N7 | 0.0 | 0.0 | 0.0 | 0.0 | 0.0 | 0.0 |
| C18:2 N6* | 0.0 | 2.2 | 0.7 | 1.6 | 0.8 | 5.1 |
| C20:0* | 1.8 | 5.2 | 12.1 | 5.5 | 2.6 | 1.1 |
| C18:3 N3* | 0.0 | 0.0 | 0.0 | 0.0 | 0.0 | 0.0 |
| C20:1 N9* | 0.0 | 0.0 | 0.0 | 0.0 | 0.0 | 0.0 |
| C18:4 N3 | 0.0 | 0.0 | 0.0 | 0.8 | 1.0 | 0.0 |
| C20:2 N6* | 0.0 | 0.0 | 0.0 | 0.0 | 0.0 | 0.0 |
| C20:3 N6 | 0.0 | 0.0 | 0.0 | 0.3 | 0.0 | 0.0 |
| C22:0* | 0.0 | 0.7 | 6.0 | 1.3 | 0.8 | 0.0 |
| C20:4 N7 | 0.0 | 0.0 | 0.0 | 0.0 | 0.0 | 0.0 |
| C20:3 N3 | 0.0 | 0.0 | 0.0 | 0.0 | 0.0 | 0.0 |
| C20:4 N6* | 1.0 | 3.0 | 0.0 | 3.1 | 2.3 | 1.2 |
| C22:1 N9* | 0.0 | 0.0 | 0.0 | 0.0 | 0.0 | 0.0 |
| C20:4 N5 | 0.0 | 0.0 | 0.0 | 0.0 | 0.0 | 0.0 |
| C20:4 N3 | 1.5 | 4.1 | 1.4 | 4.3 | 2.7 | 1.0 |
| C20:5 N3* | 18.2 | 38.6 | 2.7 | 38.6 | 39.5 | 45.5 |
| C24:0* | 0.0 | 0.0 | 4.7 | 0.6 | 0.0 | 0.3 |
| C22:4 N9 | 0.0 | 0.0 | 0.0 | 0.0 | 0.0 | 0.0 |
| C24:1 N9* | 0.0 | 0.0 | 0.0 | 0.0 | 0.0 | 0.0 |
| C22:5 N6* | 11.9 | 28.2 | 8.6 | 29.6 | 18.0 | 14.7 |
| C22:5 N3* | 1.1 | 3.4 | 0.0 | 3.5 | 2.5 | 2.2 |
| C22:6 N3* | 253.5 | 566.7 | 102.2 | 575.0 | 475.3 | 447.2 |
| Sum of all FAME's | 408.6 | 926.5 | 362.3 | 951.3 | 730.4 | 672.5 |

TABLE 8

Sample A2 Fatty Acid Profiles as a Percent of Total FAME

| Fatty Acid | Bio-mass % FAME | Crude Oil % FAME | Sterol Esters % FAME | TAG % FAME | FFA % FAME | DAG % FAME |
|---|---|---|---|---|---|---|
| C12:0* | 0.1 | 0.0 | 0.0 | 0.2 | 0.0 | 0.2 |
| C14:0* | 1.4 | 1.4 | 2.4 | 1.5 | 1.3 | 0.8 |
| C14:1* | 0.0 | 0.0 | 0.0 | 0.0 | 0.0 | 0.0 |
| C15:0 | 0.3 | 0.4 | 0.8 | 0.4 | 0.3 | 0.3 |
| C16:0* | 25.8 | 25.2 | 50.7 | 25.9 | 21.9 | 20.4 |
| C16:1* | 0.0 | 0.0 | 0.0 | 0.1 | 0.0 | 0.0 |
| C18:0* | 1.6 | 1.8 | 6.5 | 1.8 | 1.5 | 0.8 |
| C18:1 N9* | 0.0 | 0.8 | 1.4 | 0.5 | 0.3 | 0.4 |
| C18:1 N7 | 0.0 | 0.0 | 0.0 | 0.0 | 0.0 | 0.0 |
| C18:2 N6* | 0.0 | 0.2 | 0.2 | 0.2 | 0.1 | 0.8 |
| C20:0* | 0.4 | 0.6 | 3.3 | 0.6 | 0.4 | 0.2 |
| C18:3 N3* | 0.0 | 0.0 | 0.0 | 0.0 | 0.0 | 0.0 |
| C20:1 N9* | 0.0 | 0.0 | 0.0 | 0.0 | 0.0 | 0.0 |
| C18:4 N3 | 0.0 | 0.0 | 0.0 | 0.1 | 0.1 | 0.0 |
| C20:2 N6* | 0.0 | 0.0 | 0.0 | 0.0 | 0.0 | 0.0 |
| C20:3 N6 | 0.0 | 0.0 | 0.0 | 0.0 | 0.0 | 0.0 |
| C22:0* | 0.0 | 0.1 | 1.7 | 0.1 | 0.1 | 0.0 |
| C20:4 N7 | 0.0 | 0.0 | 0.0 | 0.0 | 0.0 | 0.0 |
| C20:3 N3 | 0.0 | 0.0 | 0.0 | 0.0 | 0.0 | 0.0 |
| C20:4 N6* | 0.3 | 0.3 | 0.0 | 0.3 | 0.3 | 0.2 |
| C22:1 N9* | 0.0 | 0.0 | 0.0 | 0.0 | 0.0 | 0.0 |
| C20:4 N5 | 0.0 | 0.0 | 0.0 | 0.0 | 0.0 | 0.0 |
| C20:4 N3 | 0.4 | 0.4 | 0.4 | 0.4 | 0.4 | 0.2 |
| C20:5 N3* | 4.5 | 4.2 | 0.7 | 4.1 | 5.4 | 6.8 |
| C24:0* | 0.0 | 0.0 | 1.3 | 0.1 | 0.0 | 0.0 |
| C22:4 N9 | 0.0 | 0.0 | 0.0 | 0.0 | 0.0 | 0.0 |
| C24:1 N9* | 0.0 | 0.0 | 0.0 | 0.0 | 0.0 | 0.0 |
| C22:5 N6* | 2.9 | 3.0 | 2.4 | 3.1 | 2.5 | 2.2 |
| C22:5 N3* | 0.3 | 0.4 | 0.0 | 0.4 | 0.3 | 0.3 |
| C22:6 N3* | 62.0 | 61.2 | 28.2 | 60.4 | 65.1 | 66.5 |
| Sum of FAME % | 100.0 | 100.0 | 100.0 | 100.0 | 100.0 | 100.0 |

Example 4

Triacylglycerides (TAGs) were isolated from a sample of microbial oil previously extracted from the isolated thraustochytrid deposited under ATCC Accession No. PTA-9695 using hexane extraction (sample A1) or the FRIOLEX® process (GEA Westfalia Separator UK Ltd., Milton Keynes, England) (sample A2), as described in Example 3. The relative area percent of each TAG isomer was determined using non-aqueous reversed-phase high performance liquid chromatography (NARP-HPLC) with atmospheric pressure chemical ionization-mass spectrometry (APCI-MS) detection, and a tentative identification of each positional isomer was made using the mass spectra fragmentation patterns.

Individual lipid classes, including TAGs, were isolated using flash chromatography. The TAG fraction was analyzed by HPLC/APCI-MS to determine which fatty acid moieties are present in each TAG species, and the relative amounts of each TAG species. Tentative identification of each TAG peak was based on retention time and the APCI spectra of each peak. When using NARP-HPLC, the retention of each TAG increases with the equivalent carbon number (ECN), which is defined as the total number of carbons in all of the acyl chains minus two times the number of double bonds. Also, when using optimal chromatographic conditions, critical pairs of TAG species with the same ECN but with different distributions of saturated and unsaturated fatty acids, as well as fatty acids with varying chain lengths can also be resolved. The APCI mass spectra of each TAG peak provides the masses of the protonated molecular ion $[M+H]^+$, ammonium adduct ions $[M+NH_4]^+$, and DAG fragment ions. Each TAG yields a distinctive mass spectrum, and the mass of the DAG fragment ions help to determine the identity of each TAG species. The fragment ion corresponding to a loss of an acyl group from the sn-2 position will be the least intense signal in an APCI spectra because it is energetically less favorable than a loss at the sn-1 or sn-3 position. Modern Methods for Lipid Analysis by Liquid Chromatography Mass Spectrometry and Related Techniques 276-297 (William Craig Byrdwell ed., 2005).

Flash Chromatography—

Flash chromatography was used to separate the lipid classes present in the crude oil and to determine the weight percent of each class present in the oil. The chromatography system utilized Silica Gel 60 with a mobile phase composed of Petroleum Ether and Ethyl Acetate at 3 mL/min. A step gradient was used to selectively elute each lipid class from the column. The mobile phase gradient started from 100% petroleum ether and finished with 50% ethyl acetate (followed by a 100% methanol wash). Fractions were collected in 20 mL test tubes using a Gilson FC 204 large-bed fraction collector (Gilson, Inc., Middleton, Wis.). Each tube was analyzed by TLC and the tubes containing individual lipid classes (as judged by single spots on TLC plate with expected Rf) were pooled, concentrated to dryness, and weighed. The total fraction content was then determined gravimetrically.

TLC Analysis—

Thin layer chromatography was conducted on silica gel plates. The plates were eluted using a solvent system consisting of petroleum ether:ethyl ether:acetic acid (80:20:1) and were visualized using iodine vapor. The Rf values of each spot were then compared with reported literature values for each lipid class.

HPLC/APCI-MS Analysis—

The LC/MS system used consisted of a Hewlett Packard model 1100 HPLC equipped with atmospheric pressure chemical ionization (APCI) and a Hewlett Packard model 1100 mass selective detector (MSD) (Agilent Technologies, Inc., Santa Clara, Calif.). The HPLC method utilized two PHENOMENEX® C18 column (250 mm×4.6 mm, 5 µm; Phenomenex, Inc. (Torrance, Calif.)) connected in series, a flow rate of 1 mL/min., an injection volume of 2 µL, and a column temperature of 50° C. The mobile phase consisted of 0.1% ammonium acetate in isopropanol (Solvent A) and acetonitrile (Solvent B). A linear gradient was used starting at 20% Solvent A, increasing to 75% Solvent A in 40 minutes, holding at 75% Solvent A for 5 minutes, returning to 20% Solvent A in 1 minute, and holding at 20% Solvent A for an additional 9 minutes. The MSD mass range was set to m/z 400-1150, with a fragmentor voltage of 150, a drying gas flow of 6 L/min, a nebulizer pressure of 45 psig, a drying gas temperature of 350° C., a vaporizer temperature of 325° C., a capillary voltage of 3500 V, and a corona current of 10 µA.

Tridocosahexaenoin (Tri-DHA)—

A Tri-DHA STD (NuCheck, Elysian, Minn.) was used to evaluate the chromatographic system and the accuracy of the detector response. The retention time of the Tri-DHA peak was 22.5 minutes, and the total ion chromatogram (TIC) gave good signal to noise ratio. The APCI mass spectra of the Tri-DHA peak shows the protonated molecular ion [M+H]$^+$ at m/z 1023.7, the ammonium adduct ions [M+NH$_4$]$^+$ at m/z 1040.8, and a single characteristic DAG fragment ion at m/z 695.5.

A sample of the isolated TAG fraction was prepared in hexane and analyzed by NARP HPLC/APCI-MS to determine the identities of the individual TAG isomers.

The mass spectrum of each peak was evaluated and a tentative identification of each fatty acid moiety was made, as summarized in Tables 9 and 10 below.

TABLE 9

Tentative Identification of TAG Species by LC/APCI-MS in Sample A1

| Retention Time | Peak # | Tentative Identification (sn-1/sn-2/sn-3) | Area Percent | [M + H]$^+$ | [M + NH4]$^+$ | Major (DAG) Fragments |
|---|---|---|---|---|---|---|
| 21.4 | 1 | EPA/EPA/DHA | 0.3 | 971.7 | 988.8 | 643.5, 669.3 |
| 21.9 | 2 | DHA/DHA/EPA | 4.4 | 997.8 | 1014.7 | 669.5, 695.5 |
| 22.4 | 3 | DHA/DHA/DHA | 11.6 | 1023.7 | 1040.7 | 695.5 |
| 23.3 | 4 | DHA/ARA/DHA | 0.5 | 999.6 | 1016.7 | 671.4 |
| 23.6 | 5 | DHA/DPA/DHA | 0.2 | 1025.9 | 1042.8 | 697.5 |
| 24.1 | 6 | DHA/DHA/ARA | 0.7 | 999.7 | 1016.8 | 671.5, 695.5 |
| 24.6 | 7 | DHA/DHA/DPA | 2.4 | 1025.7 | 1042.5 | 695.5, 697.4 |
| 25.3 | 8 | EPA/14:0/DHA | 0.3 | 897.6 | 914.6 | 569.4, 595.3 |
| 25.9 | 9 | DHA/DHA/14:0 | 2.6 | 923.7 | 940.7 | 595.4, 695.5 |
| 27.2 | 10 | DHA/DHA/15:0 | 0.4 | 937.8 | 954.7 | 609.5, 695.5 |
| 27.5 | 11 | EPA/EPA/16:0 | 0.2 | 899.5 | 916.7 | 597.5, 643.5 |
| 28.0 | 12 | DHA/16:0/EPA | 4.7 | 925.8 | 942.7 | 597.4, 623.5, 669.3 |
| 28.5 | 13 | DHA/DHA/16:0 | 30.8 | 951.7 | 968.7 | 623.7, 695.5 |
| 29.5 | 14 | DHA/ARA/16:0 | 0.7 | 927.6 | 944.7 | 599.5, 671.5 |
| 29.7 | 15 | DHA/DPA/16:0 | 0.9 | 953.7 | 970.8 | 625.5, 697.5 |
| 30.4 | 16 | DHA/16:0/ARA | 0.9 | 927.7 | 944.6 | 599.5, 623.5 |
| 30.8 | 17 | DHA/16:0/DPA | 4.5 | 953.8 | 970.7 | 623.4, 625.3 |
| 31.1 | 18 | DHA/18:0/DHA | 1.8 | 979.7 | 996.7 | 651.5 |
| 32.3 | 19 | DHA/14:0/16:0 | 2.3 | 851.7 | 868.7 | 523.5 |
| 33.6 | 20 | DHA/15:0/16:0 | 0.8 | 865.7 | 882.7 | 537.4 |
|  |  | DHA/20:0/DHA |  | 1007.8 | 1024.9 | 679.5 |
| 34.9 | 21 | DHA/16:0/16:0 | 19.3 | 879.7 | 896.7 | 551.5, 623.5 |
| 36.1* | 22 | DHA/22:0/DHA | 0.5 | 1035.8 | 1052.8 | 707.7 |
|  |  | DHA/18:0/15:0 |  | 893.8 | 910.8 | 565.5 |
|  |  | DPA/16:0/16:0 |  | 881.8 | 898.8 | 551.5, 625.4 |
| 37.4 | 23 | DHA/16:0/18:0 | 3.7 | 907.7 | 924.7 | 579.5, 623.5 |
| 38.9 | 24 | 16:0/16:0/14:0 | 0.3 | NA | 796.7 | 523.4, 551.5 |
| 40.1 | 25 | DHA Containing TAG | 0.4 | 1117.9 | 1134.9 | 789.7 |
| 40.8 | 26 | DHA Containing TAG | 0.4 | 1091.9 | 1108.9 | 763.7 |
| 41.3 | 27 | 16:0/16:0/16:0 | 1.0 | NA | 824.6 | 551.5 |
| 42.0 | 28 | DHA/16:0/22:0 | 0.2 | 963.8 | 980.8 | 623.3, 635.4 |
| 43.5* | 29 | DHA/20:0/22:1 | 0.3 | 1017.8 | 1034.8 | 689.7 |
|  |  | 16:0/20:0/14:0 |  | 835.6 | 852.8 | 579.5, 607.5 |
| 45.6* | 30 | DHA/22:0/22:1 | 0.7 | 1045.8 | 1062.8 | 717.7 |
| 46.3* | 31 | DHA/20:0/22:0 | 0.5 | 1019.8 | 1036.9 | 691.7 |

TABLE 10

Tentative Identification of TAG Species by LC/APCI-MS in Sample A2

| Retention Time | Peak # | Tentative Identification (sn-1/sn-2/sn-3) | Area Percent | $[M + H]^+$ | $[M + NH_4]^+$ | (DAG) Fragments |
|---|---|---|---|---|---|---|
| 21.4 | 1 | EPA/EPA/DHA | 0.3 | 971.7 | 988.8 | 643.5, 669.3 |
| 21.9 | 2 | DHA/DHA/EPA | 4.5 | 997.8 | 1014.7 | 669.5, 695.5 |
| 22.3 | 3 | DHA/DHA/DHA | 14.0 | 1023.7 | 1040.7 | 695.5 |
| 23.3 | 4 | DHA/ARA/DHA | 0.6 | 999.6 | 1016.7 | 671.4 |
| 23.6 | 5 | DHA/DPA/DHA | 0.3 | 1025.9 | 1042.8 | 697.5 |
| 24.1 | 6 | DHA/DHA/ARA | 0.9 | 999.7 | 1016.8 | 671.5, 695.5 |
| 24.6 | 7 | DHA/DHA/DPA | 3.0 | 1025.7 | 1042.5 | 695.5, 697.4 |
| 25.4 | 8 | EPA/14:0/DHA | 0.2 | 897.6 | 914.6 | 569.4, 595.3 |
| 25.9 | 9 | DHA/DHA/14:0 | 2.1 | 923.7 | 940.7 | 595.4, 695.5 |
| 27.2 | 10 | DHA/DHA/15:0 | 0.5 | 937.8 | 954.7 | 609.5, 695.5 |
| 27.6 | 11 | EPA/EPA/16:0 | 0.2 | 899.5 | 916.7 | 597.5, 643.5 |
| 28.1 | 12 | DHA/16:0/EPA | 4.2 | 925.8 | 942.7 | 597.4, 623.5, 669.3 |
| 28.5 | 13 | DHA/DHA/16:0 | 31.4 | 951.7 | 968.7 | 623.7, 695.5 |
| 29.6 | 14 | DHA/ARA/16:0 | 0.7 | 927.6 | 944.7 | 599.5, 671.5 |
| 29.8 | 15 | DHA/DPA/16:0 | 0.6 | 953.7 | 970.8 | 625.5, 697.5 |
| 30.4 | 16 | DHA/16:0/ARA | 0.9 | 927.7 | 944.6 | 599.5, 623.5 |
| 30.8 | 17 | DHA/16:0/DPA | 4.5 | 953.8 | 970.7 | 623.4, 625.3 |
| 31.1 | 18 | DHA/18:0/DHA | 2.2 | 979.7 | 996.7 | 651.5 |
| 32.4 | 19 | DHA/14:0/16:0 | 1.5 | 851.7 | 868.7 | 523.5 |
| 33.6 | 20 | DHA/15:0/16:0 | 0.9 | 865.7 | 882.7 | 537.4 |
|  |  | DHA/20:0/DHA |  | 1007.8 | 1024.9 | 679.5 |
| 34.9 | 21 | DHA/16:0/16:0 | 16.1 | 879.7 | 896.7 | 551.5, 623.5 |
| 36.1* | 22 | DHA/22:0/DHA | 0.4 | 1035.8 | 1052.8 | 707.7 |
|  |  | DHA/18:0/15:0 |  | 893.8 | 910.8 | 565.5 |
|  |  | DPA/16:0/16:0 |  | 881.8 | 898.8 | 551.5, 625.4 |
| 37.3 | 23 | DHA/16:0/18:0 | 3.4 | 907.7 | 924.7 | 579.5, 623.5 |
| 39.7 | 24 | 16:0/16:0/14:0 | 0.9 | NA | 796.7 | 523.4, 551.5 |
| 40.0 | 25 | DHA Containing TAG | 0.8 | 1117.9 | 1134.9 | 789.7 |
| 40.8 | 26 | DHA Containing TAG | 0.6 | 1091.9 | 1108.9 | 763.7 |
| 41.3 | 27 | 16:0/16:0/16:0 | 0.7 | NA | 824.6 | 551.5 |
| 42.1 | 28 | DHA/16:0/22:0 | 0.3 | 963.8 | 980.8 | 623.3, 635.4 |
| 43.5* | 29 | DHA/20:0/22:1 | 0.2 | 1017.8 | 1034.8 | 689.7 |
|  |  | 16:0/20:0/14:0 |  | 835.6 | 852.8 | 579.5, 607.5 |
| 45.6* | 30 | DHA/22:0/22:1 | 0.8 | 1045.8 | 1062.8 | 717.7 |
| 46.3* | 31 | DHA/20:0/22:0 | 0.7 | 1019.8 | 1036.9 | 691.7 |

Example 5

After oil was extracted from the fermentation broth using the Friolex process, as described in Example 3, the crude oil was further processed via refining, bleaching, and deodorizing steps to obtain a final oil. The final oil was diluted with high oleic sunflower oil to obtain finished commercial oil with a DHA content of approximately 400 mg/g. Individual lipid classes were isolated and the fatty acid profiles of each class was determined using gas chromatography with flame ionization detection (GC-FID) as fatty acid methyl esters (FAME).

Flash Chromatography—

Flash chromatography was used to separate the lipid classes present in the final oil, and to determine the weight percent of each class present in the oil. The chromatography system utilized Silica Gel 60 (EMD Chemical, Gibbstown, N.J.) with mobile phase composed of Petroleum Ether and Ethyl Acetate at 3 mL/min. A step gradient was used to selectively elute each lipid class from the column. The mobile phase gradient started from 100% petroleum ether and finished with 50% ethyl acetate (followed by a 100% methanol wash). Fractions were collected in 10 mL test tubes using a Gilson FC 204 large-bed fraction collector (Gilson, Inc., Middleton, Wis.). Each tube was analyzed by thin layer chromatography (TLC) and the tubes containing individual lipid classes (as judged by single spots on TLC plate with expected retention factor (Rf)) were pooled, concentrated to dryness, and weighed. The total fraction content was then determined gravimetric ally.

TLC Analysis—

Thin layer chromatography was conducted on silica gel plates. The plates were eluted using a solvent system consisting of petroleum ether:ethyl ether:acetic acid (80:20:1) and were visualized using iodine vapor. The Rf values of each spot were then compared with reported literature values for each lipid class.

Fatty Acid Analysis—

The final oil sample and isolated lipid classes were analyzed for fatty acid composition as FAMEs. Samples were weighed directly into screw cap test tubes, and 1 mL of C19:0 internal standard (NuCheck, Elysian, Minn.) in toluene and 2 mL of 1.5 N HCl in methanol was added to each tube. The tubes were vortexed briefly and placed in a heating block for 2 hours at 100° C. The tubes were removed from the heating block, allowed to cool, and 1 mL of saturated NaCl in water was added. The tubes were vortexed again, centrifuged, and a portion of the top (organic) layer was placed in a GC vial and analyzed by GC-FID. FAME's were quantified using a 3-point internal standard calibration curve generated using Nu-Chek-Prep GLC reference standard (Nu-Chek Prep, Inc., Elysian, Minn.) and tentatively identified based on retention time. Fatty acids present were expressed as mg/g and % of total FAME.

The sample was prepared by dissolving 250 mg of final oil in 600 μL of hexane and applying to the head of the column. After fractionation of the sample using flash chromatography, the sterol ester fraction accounted for 1.2% by weight, the triacylglyceride (TAG) fraction accounted for 92.1% by weight, the free fatty acid (FFA) fraction accounted for 2.1% by weight, the sterol fraction accounted for 1.1%, the diacylglyceride (DAG) fraction accounted for 2.8% by weight of the final oil.

The TLC analysis of the pooled fractions showed that the FFA and sterol fractions were mixed with TAG and DAG respectively. The total fatty acid profiles of the FRIOLEX® final oil and isolated fractions are shown below in Table 11 and Table 12 calculated as mg/g and % FAME, respectively.

TABLE 11

Fatty Acid Profile Calculated as Milligrams per Gram of FAME

| Fatty Acid | Final Oil | Sterol Esters | TAG | FFA | Sterol | DAG |
|---|---|---|---|---|---|---|
| | | | Wt. % | | | |
| | NA | 1.2 | 92.1 | 2.1 | 1.1 | 2.8 |
| | FAME (mg/g) | FAME (mg/g) | FAME (mg/g) | FAME (mg/g) | FAME (mg/g) | FAME (mg/g) |
| C12:0* | 0.0 | 0.0 | 1.0 | 0.0 | 1.2 | 0.6 |
| C14:0* | 11.5 | 5.1 | 11.3 | 6.0 | 9.6 | 5.7 |
| C14:1* | 0.0 | 0.0 | 0.0 | 0.0 | 0.0 | 0.0 |
| C15:0 | 2.3 | 0.0 | 2.3 | 1.2 | 2.0 | 1.9 |
| C16:0* | 183.3 | 80.0 | 180.8 | 99.9 | 149.3 | 132.2 |
| C16:1* | 0.0 | 0.0 | 0.9 | 0.0 | 0.8 | 0.6 |
| C18:0* | 19.6 | 17.5 | 19.6 | 7.5 | 16.2 | 6.7 |
| C18:1 N9* | 243.3 | 242.8 | 249.6 | 62.9 | 190.5 | 84.0 |
| C18:1 N7 | 1.9 | 1.7 | 2.0 | 0.8 | 1.9 | 0.9 |
| C18:2 N6* | 13.8 | 5.6 | 13.8 | 6.2 | 14.3 | 9.1 |
| C20:0* | 4.3 | 6.6 | 4.5 | 1.5 | 3.6 | 1.4 |
| C18:3 N3* | 0.0 | 0.0 | 0.3 | 0.0 | 0.0 | 0.0 |
| C20:1 N9* | 0.0 | 0.0 | 0.8 | 0.0 | 0.8 | 0.0 |
| C18:4 N3 | 0.0 | 0.0 | 0.7 | 1.3 | 0.9 | 0.4 |
| C20:2 N6* | 0.0 | 0.0 | 0.6 | 0.0 | 0.0 | 0.0 |
| C20:3 N6 | 0.0 | 0.0 | 0.3 | 0.0 | 0.0 | 0.0 |
| C22:0* | 3.3 | 61.0 | 3.2 | 1.1 | 3.0 | 1.2 |
| C20:4 N7 | 0.0 | 0.0 | 0.0 | 0.0 | 0.0 | 0.0 |
| C20:3 N3 | 0.0 | 0.0 | 0.0 | 0.0 | 0.0 | 0.0 |
| C20:4N6* | 1.7 | 0.0 | 2.3 | 1.4 | 1.9 | 1.3 |
| C22:1 N9* | 0.0 | 0.0 | 0.0 | 0.0 | 0.0 | 0.0 |
| C20:4 N5 | 0.0 | 0.0 | 0.0 | 0.0 | 0.0 | 0.0 |
| C20:4 N3 | 2.4 | 4.5 | 3.0 | 2.2 | 2.6 | 1.3 |
| C20:5 N3* | 28.1 | 3.0 | 27.7 | 38.6 | 25.6 | 43.2 |
| C24:0* | 1.4 | 64.3 | 1.4 | 0.0 | 2.0 | 1.0 |
| C22:4 N9 | 0.0 | 0.0 | 0.0 | 0.0 | 0.0 | 0.0 |
| C24:1 N9* | 0.0 | 0.0 | 0.0 | 0.0 | 0.0 | 0.0 |
| C22:5 N6* | 20.0 | 7.6 | 21.0 | 10.1 | 17.2 | 14.4 |
| C22:5 N3* | 2.8 | 0.0 | 3.1 | 3.7 | 3.4 | 2.9 |
| C22:6 N3* | 407.1 | 72.5 | 417.4 | 443.6 | 350.5 | 428.5 |
| Sum of all FAME's | 936.1 | 572.1 | 967.6 | 688.0 | 797.3 | 737.3 |

TABLE 12

Fatty Acid Profiles as a Percent of Total FAME

| Fatty Acid | Final Oil % FAME | Sterol Esters % FAME | TAG % FAME | FFA % FAME | Sterol % FAME | DAG % FAME |
|---|---|---|---|---|---|---|
| C12:0* | 0.0 | 0.0 | 0.1 | 0.0 | 0.2 | 0.1 |
| C14:0* | 1.2 | 0.9 | 1.2 | 0.9 | 1.2 | 0.8 |
| C14:1* | 0.0 | 0.0 | 0.0 | 0.0 | 0.0 | 0.0 |
| C15:0 | 0.2 | 0.0 | 0.2 | 0.2 | 0.2 | 0.3 |
| C16:0* | 19.6 | 14.0 | 18.7 | 14.5 | 18.7 | 17.9 |
| C16:1* | 0.0 | 0.0 | 0.1 | 0.0 | 0.1 | 0.1 |
| C18:0* | 2.1 | 3.1 | 2.0 | 1.1 | 2.0 | 0.9 |
| C18:1 N9* | 26.0 | 42.4 | 25.8 | 9.1 | 23.9 | 11.4 |
| C18:1 N7 | 0.2 | 0.3 | 0.2 | 0.1 | 0.2 | 0.1 |
| C18:2 N6* | 1.5 | 1.0 | 1.4 | 0.9 | 1.8 | 1.2 |
| C20:0* | 0.5 | 1.1 | 0.5 | 0.2 | 0.5 | 0.2 |
| C18:3 N3* | 0.0 | 0.0 | 0.0 | 0.0 | 0.0 | 0.0 |
| C20:1 N9* | 0.0 | 0.0 | 0.1 | 0.0 | 0.1 | 0.0 |
| C18:4 N3 | 0.0 | 0.0 | 0.1 | 0.2 | 0.1 | 0.1 |
| C20:2 N6* | 0.0 | 0.0 | 0.1 | 0.0 | 0.0 | 0.0 |
| C20:3 N6 | 0.0 | 0.0 | 0.0 | 0.0 | 0.0 | 0.0 |
| C22:0* | 0.4 | 10.7 | 0.3 | 0.2 | 0.4 | 0.2 |
| C20:4 N7 | 0.0 | 0.0 | 0.0 | 0.0 | 0.0 | 0.0 |
| C20:3 N3 | 0.0 | 0.0 | 0.0 | 0.0 | 0.0 | 0.0 |
| C20:4N6* | 0.2 | 0.0 | 0.2 | 0.2 | 0.2 | 0.2 |
| C22:1 N9* | 0.0 | 0.0 | 0.0 | 0.0 | 0.0 | 0.0 |
| C20:4 N5 | 0.0 | 0.0 | 0.0 | 0.0 | 0.0 | 0.0 |
| C20:4 N3 | 0.3 | 0.8 | 0.3 | 0.3 | 0.3 | 0.2 |
| C20:5 N3* | 3.0 | 0.5 | 2.9 | 5.6 | 3.2 | 5.9 |
| C24:0* | 0.2 | 11.2 | 0.1 | 0.0 | 0.2 | 0.1 |
| C22:4 N9 | 0.0 | 0.0 | 0.0 | 0.0 | 0.0 | 0.0 |
| C24:1 N9* | 0.0 | 0.0 | 0.0 | 0.0 | 0.0 | 0.0 |
| C22:5 N6* | 2.1 | 1.3 | 2.2 | 1.5 | 2.2 | 1.9 |
| C22:5 N3* | 0.3 | 0.0 | 0.3 | 0.5 | 0.4 | 0.4 |
| C22:6 N3* | 43.6 | 12.7 | 43.1 | 64.5 | 44.0 | 58.1 |
| Sum of FAME % | 100 | 100 | 100 | 100 | 100 | 100 |

Example 6

An analysis of the triacylglycerides (TAGs) of the final oil described in Example 5 was performed using techniques described in Example 4. The tentative identification of each fatty acid moiety was made, as summarized in Tables 13 and 14 below.

TABLE 13

Tentative Identification of Major TAG Species

| Peak retention Time, min. | Tentative Identification (sn-1/sn-2/sn-3) | Area Percent |
|---|---|---|
| 22.0 | DHA/DHA/EPA | 3.4 |
| 22.5 | DHA DHA/DHA | 10.4 |
| 24.7 | DHA/DHA/DPA | 2.1 |
| 28.2 | DHA/16:0/EPA | 3.4 |
| 28.7 | DHA/16:0/DHA | 23.0 |
| 31.0 | DHA/16:0/DPA | 3.3 |
| 35.2 | DHA/16:0/16:0 | 11.6 |
| 37.6 | DHA/16:0/18:0 | 4.3 |
| 40.4 | 18:1/18:1/18:1 | 14.0 |

TABLE 14

Tentative Identification of TAG Species by LC/APCI-MS

| Retention Time | Peak # | Tentative Identification (sn-1/sn-2/sn-3) | Area Percent | [M + H]+ | [M + NH4]+ | (DAG) Fragments |
|---|---|---|---|---|---|---|
| 21.5 | 1 | EPA/EPA/DHA | 0.4 | 971.7 | 988.7 | 643.5, 669.5 |
| 22.0 | 2 | DHA/DHA/EPA | 3.4 | 997.8 | 1014.7 | 669.4, 695.5 |
| 22.5 | 3 | DHA/DHA/DHA | 10.4 | 1023.8 | 1040.7 | 695.5 |
| 23.4 | 4 | DHA/DHA/ARA | 0.5 | 999.8 | 1016.7 | 671.4, 695.3 |
| 23.7 | 5 | DHA/DPA/DHA | 0.3 | 1025.7 | 1042.7 | 697.5 |
| 24.2 | 6 | DHA/DHA/ARA | 0.8 | 999.7 | 1016.8 | 671.5, 695.5 |
| 24.7 | 7 | DHA/DHA/DPA | 2.1 | 1025.7 | 1042.5 | 695.5, 697.4 |
| 25.6 | 8 | EPA/14:0/DHA | 0.2 | 897.7 | 914.8 | 569.4, 595.3 |
| 26.1 | 9 | DHA/14:0/DHA | 1.4 | 923.7 | 940.7 | 595.5, 695.5 |
| 27.4 | 10 | DHA/15:0/DHA | 0.3 | 937.8 | 954.8 | 609.3 |
| 27.7 | 11 | EPA/16:0/EPA | 0.2 | 899.5 | 916.7 | 597.5 |
| 28.2 | 12 | DHA/16:0/EPA | 3.4 | 925.7 | 942.7 | 597.5, 623.4, 669.3 |
| 28.7 | 13 | DHA/16:0/DHA | 23.0 | 951.7 | 968.7 | 623.5, 695.5 |
| 29.8 | 14 | DHA/16:0/ARA | 0.5 | 927.7 | 944.8 | 599.5, 623.5 |
| 30.0 | 15 | DHA/16:0/DPA | 0.7 | 953.8 | 970.8 | 623.4, 625.5 |
| 30.6 | 16 | DHA/16:0/ARA | 0.8 | 927.7 | 944.8 | 599.5, 623.5 |
| 31.0 | 17 | DHA/16:0/DPA | 3.3 | 953.7 | 970.7 | 623.4, 625.5 |
| 31.3 | 18 | DHA/18:0/DHA | 1.6 | 979.8 | 996.8 | 651.5 |
| 32.6 | 19 | DHA/14:0/16:0 | 1.6 | 851.8 | 868.8 | 523.5 |
| 33.9 | 20 | DHA/15:0/16:0 | 0.8 | 865.7 | 882.7 | 537.4 |
|  |  | DHA/20:0/DHA |  | 1007.8 | 1024.8 | 679.5 |
| 35.2 | 21 | DHA/16:0/16:0 | 11.6 | 879.7 | 896.8 | 551.5, 623.5 |
| 36.4 | 22 | DHA/22:0/DHA | 0.5 | 1035.8 | 1052.8 | 707.7 |
|  |  | DHA/18:0/15:0 |  | 893.8 | 910.8 | 565.5 |
|  |  | DPA/16:0/16:0 |  | 881.8 | 898.8 | 551.5, 625.4 |
| 37.6 | 23 | DHA/16:0/18:0 | 4.3 | 907.8 | 924.8 | 579.5, 623.5 |
| 40.0 | 24 | DHA/16:0/20:0 | 0.8 | 935.8 | 952.8 | 607.6, 623.5 |
| 40.4 | 25 | 18:1/18:1/18:1 | 14.0 | 885.8 | 902.8 | 603.5 |
| 40.7 | 26 | 18:1/16:0/18:1 | 2.2 | 859.8 | 876.8 | 577.5 |
| 41.1 | 27 | DHA Containing TAG | 1.6 | 1092.0 | 1108.8 | 763.7 |
| 42.4 | 28 | 24:0 Containing TAG | 0.5 | 963.8 | 980.9 | 594.5 |
| 43.0 | 29 | 18:1/18:1/18:0 | 1.9 | 887.7 | 904.8 | 603.6, 605.6 |
| 45.9 | 30 | DHA/22:0/22:1 | 0.9 | 1045.9 | 1062.9 | 717.6 |
| 46.6 | 31 | DHA/20:0/22:0 | 0.7 | 1019.8 | 1036.8 | 691.5 |

Example 7

A two-day old inoculum flask of the isolated thraustochytrid deposited under ATCC Accession No. PTA-9695 was prepared in a carbon and nitrogen-fed culture with 980 ppm Cl− (thraustochytrid media).

Mutagenesis was carried out according to following procedure:

A sterile T=2 day old flask, approximately 50 ml, was poured into a sterile 40 ml glass homogenizer. The culture received 50 plunges in the homogenizer. The culture was pipeted out and filtered through a sterile 50 micron mesh filter, which was placed in a 50 ml sterile tube (the mesh was used as a means of retaining the larger clumps of colonies while letting the smaller clusters and single cells pass through the 50 micron mesh.). The entire concentrated macerate was collected in a sterile 50 ml tube. The macerated culture was vortexed and dilutions at levels up to 1:100 fold were made in tubes containing thraustochytrid media. The diluted macerate samples were vortexed prior to adding 200 μl of inoculum to a thraustochytrid media agar petri dish, 100×15 mm, containing 4-5 glass beads (3 mm glass beads). Each plate was gently agitated in an effort to have the beads spread the inoculum evenly around the plate. Beads were dumped off of plates and plates were left to sit with covers on for approximately 5 minutes to dry. Lights in both the sterile hood and adjoining areas were turned off as the procedure was performed in dim light. There was minimal light available to be able to run the procedure but only indirect and dim.

Five replicate plates were placed on the floor of the XL crosslinker (Spectronics Corporation, New York) with the lids off while the samples were irradiated. The crosslinker delivered power in terms of microjoules and a level was sought that achieved a 90%-95% Kill. Five replicate control plates were inoculated with un-mutagenized cells using the same protocol. These cell counts were used to calculate the % Kill. Once the irradiation was finished the plates were taken out, the lids were replaced, and the plates were wrapped in parafilm followed by a wrap in aluminum foil. It was imperative that the plates grew for the first week in the dark so that they were not able to repair the damaged genes.

Plates were placed in a 22.5° C. room for about 10 days prior to counting the colonies. When final counts were made, individual colonies were picked with a sterile inoculating loop and re-streaked on new thraustochytrid media plates. Each colony was plated on an individual plate. As plates grew dense a sample was taken, using a inoculating loop, and inoculated into a sterile 250 ml shake flask containing 50 ml of thraustochytrid media. This flask was placed on a shaker at 200 rpm in a 22.5° C. room. On T=7 days the shake flask culture was harvested into a 50 ml sterile tube. The pH was taken and the sample was spun down to collect the biomass pellet. Each sample was rinsed and re-suspended in a 50:50 mixture of isopropyl alcohol and distilled water prior to being re-spun. The collected pellet was freeze dried, weighed, and a FAME analysis was performed. The data in Tables 15-21 represents mutants produced with the above process.

TABLE 15

Mutants of Thraustochytrid Strain ATCC Accession No. PTA-9695

| Fatty Acids | control ATCC PTA-9695 | Mutant 1 | Mutant 2 | Mutant 3 | Mutant 4 | Mutant 5 | Mutant 8 | Mutant 9 | Mutant 10 |
|---|---|---|---|---|---|---|---|---|---|
| %08:0 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 |
| %12:0 | 0.10 | 0.10 | 0.08 | 0.08 | 0.13 | 0.07 | 0.11 | 0.08 | 0.08 |
| %12:1 | 0.00 | 0.00 | 0.00 | 0.00 | 0.00 | 0.00 | 0.00 | 0.00 | 0.00 |
| %13:0 | 0.11 | 0.11 | 0.17 | 0.13 | 0.12 | 0.18 | 0.11 | 0.15 | 0.14 |
| %13:1 | 0.00 | 0.00 | 0.00 | 0.00 | 0.00 | 0.00 | 0.00 | 0.00 | 0.00 |
| %14:0 | 1.79 | 1.85 | 1.49 | 1.37 | 2.36 | 1.29 | 1.85 | 1.72 | 1.57 |
| %14:1 | 0.00 | 0.00 | 0.00 | 0.00 | 0.00 | 0.00 | 0.00 | 0.00 | 0.00 |
| %15:1 | 0.00 | 0.00 | 0.00 | 0.00 | 0.00 | 0.00 | 0.00 | 0.00 | 0.00 |
| %16:0 | 30.98 | 28.75 | 29.96 | 29.97 | 30.33 | 29.86 | 30.97 | 30.11 | 29.20 |
| %16:1 | 0.27 | 0.20 | 0.31 | 0.14 | 0.25 | 0.27 | 0.16 | 0.27 | 0.24 |
| %16:2 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 |
| %17:0 | 0.12 | 0.15 | 0.13 | 0.17 | 0.27 | 0.12 | 0.16 | 0.13 | 0.13 |
| %18:0 | 1.29 | 1.22 | 1.38 | 1.47 | 1.22 | 1.57 | 1.25 | 1.34 | 1.34 |
| %18:1 n-9 | 0.00 | 0.00 | 0.00 | 0.00 | 0.00 | 0.00 | 0.00 | 0.00 | 0.00 |
| %18:1 n-7 | 0.00 | 0.00 | 0.00 | 0.00 | 0.00 | 0.00 | 0.00 | 0.00 | 0.00 |
| %18:2 | 0.00 | 0.00 | 0.00 | 0.00 | 0.00 | 0.00 | 0.00 | 0.00 | 0.00 |
| %18:3 n-6 | 0.00 | 0.03 | 0.00 | 0.00 | 0.07 | 0.00 | 0.03 | 0.00 | 0.00 |
| %18:3 n-3 | 0.00 | 0.00 | 0.00 | 0.00 | 0.00 | 0.00 | 0.00 | 0.00 | 0.00 |
| %18:4 n-3 | 0.00 | 0.00 | 0.00 | 0.00 | 0.00 | 0.00 | 0.00 | 0.00 | 0.00 |
| %20:0 | 0.39 | 0.36 | 0.42 | 0.45 | 0.34 | 0.46 | 0.37 | 0.40 | 0.40 |
| %20:1 n-9 | 0.00 | 0.00 | 0.00 | 0.00 | 0.00 | 0.00 | 0.00 | 0.00 | 0.00 |
| %20:2 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 |
| %20:3 n-6 | 0.00 | 0.00 | 0.00 | 0.00 | 0.00 | 0.00 | 0.00 | 0.00 | 0.00 |
| %20:3 n-3 | 0.37 | 0.38 | 0.32 | 0.42 | 0.44 | 0.32 | 0.41 | 0.33 | 0.36 |
| %20:4 ARA | 0.55 | 0.55 | 0.94 | 0.57 | 0.80 | 0.89 | 0.60 | 0.73 | 0.75 |
| %20:5 n-3 EPA | 2.62 | 2.94 | 3.01 | 2.40 | 3.64 | 2.83 | 2.54 | 2.81 | 2.81 |
| %22:0 | 0.08 | 0.08 | 0.09 | 0.09 | 0.07 | 0.10 | 0.07 | 0.09 | 0.09 |
| %22:1 | 0.00 | 0.00 | 0.00 | 0.00 | 0.00 | 0.00 | 0.00 | 0.00 | 0.00 |
| %22:2 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 |
| %22:4 n-6 | 0.00 | 0.00 | 0.00 | 0.00 | 0.00 | 0.00 | 0.00 | 0.00 | 0.00 |
| %22:5 n-6 | 3.19 | 3.19 | 2.94 | 3.43 | 3.35 | 2.87 | 3.34 | 3.01 | 3.15 |
| %22:5 n-3 | 0.18 | 0.18 | 0.21 | 0.23 | 0.20 | 0.18 | 0.20 | 0.17 | 0.18 |
| %22:6 n-3 DHA | 56.88 | 58.63 | 57.56 | 57.85 | 54.87 | 57.98 | 56.62 | 57.53 | 58.52 |
| %24:0 | 0.00 | 0.00 | 0.00 | 0.00 | 0.00 | 0.00 | 0.00 | 0.00 | 0.00 |
| %24:1 | 0.00 | 0.08 | 0.00 | 0.00 | 0.00 | 0.00 | 0.00 | 0.09 | 0.00 |
| % Fat | 46.83 | 46.10 | 31.23 | 47.39 | 49.78 | 30.62 | 54.71 | 37.72 | 37.87 |
| % Unknown | 0.85 | 0.46 | 0.35 | 0.51 | 0.51 | 0.36 | 0.50 | 0.38 | 0.39 |

TABLE 16

Mutants of Thraustochytrid Strain ATCC Accession No. PTA-9695

| Fatty Acids | control ATCC PTA-9695 | Mutant 11 | Mutant 13 | Mutant 14 | Mutant 15 | Mutant 16 | Mutant 20 | Mutant 21 | Mutant 22 |
|---|---|---|---|---|---|---|---|---|---|
| %08:0 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 |
| %12:0 | 0.10 | 0.10 | 0.08 | 0.09 | 0.11 | 0.11 | 0.09 | 0.09 | 0.10 |
| %12:1 | 0.00 | 0.00 | 0.00 | 0.00 | 0.00 | 0.00 | 0.00 | 0.00 | 0.00 |
| %13:0 | 0.11 | 0.15 | 0.16 | 0.14 | 0.13 | 0.12 | 0.17 | 0.16 | 0.13 |
| %13:1 | 0.00 | 0.00 | 0.00 | 0.00 | 0.00 | 0.00 | 0.00 | 0.00 | 0.00 |
| %14:0 | 1.79 | 1.89 | 1.43 | 1.75 | 1.83 | 1.98 | 1.76 | 1.77 | 1.81 |
| %14:1 | 0.00 | 0.00 | 0.00 | 0.00 | 0.00 | 0.00 | 0.00 | 0.00 | 0.00 |
| %15:1 | 0.00 | 0.00 | 0.00 | 0.00 | 0.00 | 0.00 | 0.00 | 0.00 | 0.00 |
| %16:0 | 30.98 | 31.08 | 30.27 | 29.92 | 31.79 | 30.18 | 28.84 | 30.05 | 30.81 |
| %16:1 | 0.27 | 0.32 | 0.26 | 0.28 | 0.21 | 0.24 | 0.23 | 0.23 | 0.33 |
| %16:2 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 |
| %17:0 | 0.12 | 0.24 | 0.15 | 0.13 | 0.15 | 0.12 | 0.14 | 0.16 | 0.14 |

TABLE 16-continued

Mutants of Thraustochytrid Strain ATCC Accession No. PTA-9695

| Fatty Acids | control ATCC PTA-9695 | Mutant 11 | Mutant 13 | Mutant 14 | Mutant 15 | Mutant 16 | Mutant 20 | Mutant 21 | Mutant 22 |
|---|---|---|---|---|---|---|---|---|---|
| %18:0 | 1.29 | 1.36 | 1.44 | 1.31 | 1.36 | 1.21 | 1.28 | 1.34 | 1.33 |
| %18:1 n-9 | 0.00 | 0.00 | 0.00 | 0.00 | 0.00 | 0.00 | 0.00 | 0.00 | 0.00 |
| %18:1 n-7 | 0.00 | 0.00 | 0.00 | 0.00 | 0.00 | 0.00 | 0.00 | 0.00 | 0.00 |
| %18:2 | 0.00 | 0.00 | 0.00 | 0.00 | 0.00 | 0.00 | 0.00 | 0.00 | 0.00 |
| %18:3 n-6 | 0.00 | 0.05 | 0.00 | 0.00 | 0.00 | 0.03 | 0.00 | 0.00 | 0.00 |
| %18:3 n-3 | 0.00 | 0.00 | 0.00 | 0.00 | 0.00 | 0.00 | 0.00 | 0.00 | 0.00 |
| %18:4 n-3 | 0.00 | 0.00 | 0.00 | 0.00 | 0.00 | 0.00 | 0.00 | 0.00 | 0.00 |
| %20:0 | 0.39 | 0.38 | 0.42 | 0.39 | 0.40 | 0.37 | 0.37 | 0.38 | 0.38 |
| %20:1 n-9 | 0.00 | 0.00 | 0.06 | 0.00 | 0.00 | 0.00 | 0.00 | 0.00 | 0.00 |
| %20:2 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 |
| %20:3 n-6 | 0.00 | 0.00 | 0.00 | 0.00 | 0.00 | 0.00 | 0.00 | 0.00 | 0.00 |
| %20:3 n-3 | 0.37 | 0.43 | 0.36 | 0.33 | 0.36 | 0.37 | 0.33 | 0.35 | 0.34 |
| %20:4 ARA | 0.55 | 0.79 | 0.72 | 0.80 | 0.64 | 0.62 | 0.83 | 0.73 | 0.69 |
| %20:5 n-3 EPA | 2.62 | 3.17 | 2.72 | 2.97 | 2.52 | 2.66 | 3.03 | 2.90 | 2.87 |
| %22:0 | 0.08 | 0.08 | 0.09 | 0.08 | 0.08 | 0.08 | 0.08 | 0.08 | 0.08 |
| %22:1 | 0.00 | 0.00 | 0.00 | 0.00 | 0.00 | 0.00 | 0.00 | 0.00 | 0.00 |
| %22:2 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 |
| %22:4 n-6 | 0.00 | 0.00 | 0.00 | 0.00 | 0.00 | 0.00 | 0.00 | 0.00 | 0.00 |
| %22:5 n-6 | 3.19 | 3.25 | 3.06 | 2.97 | 3.07 | 3.16 | 2.98 | 3.01 | 3.02 |
| %22:5 n-3 | 0.18 | 0.20 | 0.19 | 0.17 | 0.19 | 0.16 | 0.17 | 0.18 | 0.18 |
| %22:6 n-3 DHA | 56.88 | 55.17 | 57.52 | 57.63 | 56.02 | 57.38 | 58.58 | 57.45 | 56.65 |
| %24:0 | 0.00 | 0.00 | 0.00 | 0.00 | 0.00 | 0.00 | 0.00 | 0.00 | 0.00 |
| %24:1 | 0.00 | 0.00 | 0.00 | 0.00 | 0.00 | 0.07 | 0.00 | 0.00 | 0.08 |
| % Fat | 46.83 | 46.19 | 37.00 | 38.41 | 48.46 | 47.32 | 37.71 | 40.23 | 43.55 |
| % Unknown | 0.85 | 0.47 | 0.39 | 0.36 | 0.47 | 0.44 | 0.37 | 0.39 | 0.38 |

TABLE 17

Mutants of Thraustochytrid Strain ATCC Accession No. PTA-9695

| Fatty Acids | control ATCC PTA-9695 | Mutant 24 | Mutant 26 | Mutant 27 | Mutant 29 | Mutant 30 | Mutant 33 | Mutant 34 | Mutant 35 |
|---|---|---|---|---|---|---|---|---|---|
| %08:0 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 |
| %12:0 | 0.10 | 0.11 | 0.09 | 0.09 | 0.08 | 0.08 | 0.10 | 0.11 | 0.09 |
| %12:1 | 0.00 | 0.00 | 0.00 | 0.00 | 0.00 | 0.00 | 0.00 | 0.00 | 0.00 |
| %13:0 | 0.11 | 0.12 | 0.13 | 0.14 | 0.16 | 0.14 | 0.12 | 0.12 | 0.10 |
| %13:1 | 0.00 | 0.00 | 0.00 | 0.00 | 0.00 | 0.00 | 0.00 | 0.00 | 0.00 |
| %14:0 | 1.79 | 1.98 | 1.71 | 1.69 | 1.63 | 1.66 | 1.93 | 2.01 | 1.59 |
| %14:1 | 0.00 | 0.00 | 0.00 | 0.00 | 0.00 | 0.00 | 0.00 | 0.00 | 0.00 |
| %15:1 | 0.00 | 0.00 | 0.00 | 0.00 | 0.00 | 0.00 | 0.70 | 0.54 | 0.39 |
| %16:0 | 30.98 | 30.61 | 30.32 | 30.21 | 29.70 | 29.50 | 30.26 | 32.28 | 30.78 |
| %16:1 | 0.27 | 0.19 | 0.22 | 0.22 | 0.26 | 0.26 | 0.29 | 0.26 | 0.16 |
| %16:2 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 |
| %17:0 | 0.12 | 0.15 | 0.18 | 0.16 | 0.13 | 0.13 | 0.26 | 0.16 | 0.12 |
| %18:0 | 1.29 | 1.24 | 1.31 | 1.31 | 1.32 | 1.30 | 1.32 | 1.37 | 1.34 |
| %18:1 n-9 | 0.00 | 0.00 | 0.00 | 0.00 | 0.00 | 0.00 | 0.10 | 0.11 | 0.09 |
| %18:1 n-7 | 0.00 | 0.00 | 0.00 | 0.00 | 0.00 | 0.00 | 0.00 | 0.00 | 0.00 |
| %18:2 | 0.00 | 0.00 | 0.00 | 0.00 | 0.00 | 0.00 | 0.00 | 0.00 | 0.00 |
| %18:3 n-6 | 0.00 | 0.00 | 0.00 | 0.00 | 0.00 | 0.00 | 0.00 | 0.00 | 0.00 |
| %18:3 n-3 | 0.00 | 0.00 | 0.00 | 0.00 | 0.00 | 0.00 | 0.00 | 0.00 | 0.00 |
| %18:4 n-3 | 0.00 | 0.00 | 0.00 | 0.00 | 0.00 | 0.00 | 0.00 | 0.00 | 0.00 |
| %20:0 | 0.39 | 0.37 | 0.39 | 0.40 | 0.40 | 0.39 | 0.37 | 0.40 | 0.40 |
| %20:1 n-9 | 0.00 | 0.00 | 0.00 | 0.00 | 0.00 | 0.00 | 0.00 | 0.13 | 0.14 |
| %20:2 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 |
| %20:3 n-6 | 0.00 | 0.00 | 0.00 | 0.00 | 0.00 | 0.00 | 0.00 | 0.00 | 0.00 |
| %20:3 n-3 | 0.37 | 0.38 | 0.37 | 0.35 | 0.35 | 0.35 | 0.00 | 0.00 | 0.00 |
| %20:4 ARA | 0.55 | 0.61 | 0.59 | 0.69 | 0.68 | 0.32 | 0.34 | 0.24 | 0.28 |
| %20:5 n-3 EPA | 2.62 | 2.62 | 2.70 | 2.85 | 2.90 | 2.91 | 3.28 | 2.51 | 2.59 |
| %22:0 | 0.08 | 0.08 | 0.08 | 0.08 | 0.09 | 0.08 | 0.08 | 0.08 | 0.08 |
| %22:1 | 0.00 | 0.00 | 0.00 | 0.00 | 0.00 | 0.00 | 0.00 | 0.00 | 0.00 |

TABLE 17-continued

Mutants of Thraustochytrid Strain ATCC Accession No. PTA-9695

| Fatty Acids | control ATCC PTA-9695 | Mutant 24 | Mutant 26 | Mutant 27 | Mutant 29 | Mutant 30 | Mutant 33 | Mutant 34 | Mutant 35 |
|---|---|---|---|---|---|---|---|---|---|
| %22:2 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 |
| %22:4 n-6 | 0.00 | 0.00 | 0.00 | 0.00 | 0.00 | 0.00 | 0.00 | 0.00 | 0.00 |
| %22:5 n-6 | 3.19 | 3.10 | 3.11 | 3.05 | 3.10 | 3.11 | 3.43 | 3.26 | 3.56 |
| %22:5 n-3 | 0.18 | 0.16 | 0.18 | 0.19 | 0.18 | 0.18 | 0.18 | 0.15 | 0.24 |
| %22:6 n-3 DHA | 56.88 | 57.03 | 57.46 | 57.46 | 57.96 | 58.52 | 55.92 | 54.96 | 56.73 |
| %24:0 | 0.00 | 0.00 | 0.00 | 0.00 | 0.00 | 0.00 | 0.00 | 0.00 | 0.00 |
| %24:1 | 0.00 | 0.08 | 0.00 | 0.00 | 0.00 | 0.00 | 0.07 | 0.07 | 0.07 |
| % Fat | 46.83 | 47.80 | 43.50 | 38.86 | 38.60 | 38.16 | 46.95 | 46.43 | 51.55 |
| % Unknown | 0.85 | 0.45 | 0.42 | 0.39 | 0.37 | 0.82 | 1.25 | 1.23 | 1.25 |

TABLE 18

Mutants of Thraustochytrid Strain ATCC Accession No. PTA-9695

| Fatty Acids | control ATCC PTA-9695 | Mutant 36 | Mutant 37 | Mutant 38 | Mutant 39 | Mutant 40 | Mutant 42 | Mutant 43 | Mutant 44 |
|---|---|---|---|---|---|---|---|---|---|
| %08:0 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 |
| %12:0 | 0.10 | 0.00 | 0.11 | 0.00 | 0.11 | 0.09 | 0.08 | 0.12 | 0.09 |
| %12:1 | 0.00 | 0.00 | 0.00 | 0.00 | 0.00 | 0.00 | 0.00 | 0.00 | 0.00 |
| %13:0 | 0.11 | 0.44 | 0.09 | 0.24 | 0.12 | 0.11 | 0.12 | 0.08 | 0.15 |
| %13:1 | 0.00 | 0.00 | 0.00 | 0.00 | 0.00 | 0.00 | 0.00 | 0.00 | 0.00 |
| %14:0 | 1.79 | 1.25 | 1.99 | 1.48 | 1.96 | 1.76 | 1.43 | 2.17 | 1.75 |
| %14:1 | 0.00 | 0.00 | 0.00 | 0.00 | 0.00 | 0.00 | 0.00 | 0.00 | 0.00 |
| %15:1 | 0.00 | 2.12 | 0.48 | 0.71 | 0.54 | 0.55 | 0.36 | 0.62 | 0.50 |
| %16:0 | 30.98 | 26.95 | 28.04 | 32.28 | 30.84 | 30.25 | 25.77 | 43.37 | 30.18 |
| %16:1 | 0.27 | 0.00 | 0.26 | 0.23 | 0.22 | 0.21 | 0.10 | 1.05 | 0.22 |
| %16:2 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 |
| %17:0 | 0.12 | 0.95 | 0.13 | 0.28 | 0.16 | 0.16 | 0.10 | 0.26 | 0.13 |
| %18:0 | 1.29 | 1.58 | 1.11 | 1.79 | 1.30 | 1.29 | 1.25 | 2.21 | 1.34 |
| %18:1 n-9 | 0.00 | 0.37 | 0.08 | 0.25 | 0.09 | 0.09 | 0.12 | 0.09 | 0.10 |
| %18:1 n-7 | 0.00 | 0.00 | 0.00 | 0.00 | 0.00 | 0.00 | 0.00 | 0.05 | 0.00 |
| %18:2 | 0.00 | 0.00 | 0.00 | 0.00 | 0.00 | 0.00 | 0.00 | 0.00 | 0.00 |
| %18:3 n-6 | 0.00 | 0.00 | 0.06 | 0.00 | 0.00 | 0.00 | 0.00 | 0.00 | 0.00 |
| %18:3 n-3 | 0.00 | 0.00 | 0.00 | 0.00 | 0.00 | 0.00 | 0.00 | 0.00 | 0.00 |
| %18:4 n-3 | 0.00 | 0.00 | 0.00 | 0.00 | 0.00 | 0.00 | 0.00 | 0.00 | 0.00 |
| %20:0 | 0.39 | 0.34 | 0.31 | 0.43 | 0.38 | 0.39 | 0.36 | 0.61 | 0.40 |
| %20:1 n-9 | 0.00 | 0.00 | 0.00 | 0.43 | 0.00 | 0.14 | 0.15 | 0.15 | 0.49 |
| %20:2 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 |
| %20:3 n-6 | 0.00 | 0.00 | 0.00 | 0.00 | 0.00 | 0.00 | 0.00 | 0.00 | 0.00 |
| %20:3 n-3 | 0.37 | 0.00 | 0.00 | 0.00 | 0.00 | 0.00 | 0.00 | 0.00 | 0.00 |
| %20:4 ARA | 0.55 | 0.41 | 0.31 | 0.24 | 0.27 | 0.24 | 0.30 | 0.35 | 0.23 |
| %20:5 n-3 EPA | 2.62 | 5.36 | 2.77 | 4.00 | 2.72 | 2.80 | 3.21 | 3.47 | 2.80 |
| %22:0 | 0.08 | 0.00 | 0.07 | 0.14 | 0.07 | 0.08 | 0.07 | 0.14 | 0.08 |
| %22:1 | 0.00 | 0.00 | 0.00 | 0.00 | 0.00 | 0.00 | 0.00 | 0.00 | 0.00 |
| %22:2 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 |
| %22:4 n-6 | 0.00 | 0.00 | 0.06 | 0.00 | 0.00 | 0.00 | 0.00 | 0.00 | 0.00 |
| %22:5 n-6 | 3.19 | 2.40 | 3.94 | 2.57 | 3.48 | 3.29 | 3.89 | 2.37 | 3.33 |
| %22:5 n-3 | 0.18 | 0.00 | 0.19 | 0.00 | 0.17 | 0.17 | 0.30 | 0.33 | 0.17 |
| %22:6 n-3 DHA | 56.88 | 57.52 | 58.57 | 54.20 | 56.24 | 57.09 | 60.99 | 41.61 | 56.76 |
| %24:0 | 0.00 | 0.00 | 0.00 | 0.00 | 0.00 | 0.00 | 0.00 | 0.00 | 0.00 |
| %24:1 | 0.00 | 0.00 | 0.08 | 0.00 | 0.08 | 0.09 | 0.08 | 0.06 | 0.09 |
| % Fat | 46.83 | 12.73 | 54.86 | 18.08 | 45.74 | 42.59 | 42.48 | 56.44 | 41.20 |
| % Unknown | 0.85 | 0.29 | 1.36 | 0.73 | 1.28 | 1.20 | 1.31 | 0.90 | 1.20 |

TABLE 19

Mutants of Thraustochytrid Strain ATCC Accession No. PTA-9695

| Fatty Acids | control ATCC PTA-9695 | Mutant 45 | Mutant 46 | Mutant 47 | Mutant 48 | Mutant 49 | Mutant 50 | Mutant 51 | Mutant 52 |
|---|---|---|---|---|---|---|---|---|---|
| %08:0 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 |
| %12:0 | 0.10 | 0.10 | 0.13 | 0.11 | 0.07 | 0.09 | 0.09 | 0.09 | 0.11 |
| %12:1 | 0.00 | 0.00 | 0.00 | 0.00 | 0.00 | 0.00 | 0.00 | 0.00 | 0.00 |
| %13:0 | 0.11 | 0.11 | 0.10 | 0.09 | 0.13 | 0.09 | 0.13 | 0.10 | 0.09 |
| %13:1 | 0.00 | 0.00 | 0.00 | 0.00 | 0.00 | 0.00 | 0.00 | 0.00 | 0.00 |
| %14:0 | 1.79 | 1.79 | 2.07 | 1.86 | 1.52 | 1.62 | 1.78 | 1.78 | 1.85 |
| %14:1 | 0.00 | 0.00 | 0.00 | 0.00 | 0.00 | 0.00 | 0.00 | 0.00 | 0.00 |
| %15:1 | 0.00 | 0.41 | 0.76 | 0.57 | 0.46 | 0.48 | 0.55 | 0.53 | 0.53 |
| %16:0 | 30.98 | 28.79 | 24.90 | 30.07 | 29.07 | 31.21 | 30.46 | 30.79 | 32.53 |
| %16:1 | 0.27 | 0.19 | 0.24 | 0.18 | 0.17 | 0.17 | 0.18 | 0.21 | 0.22 |
| %16:2 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 |
| %17:0 | 0.12 | 0.11 | 0.24 | 0.16 | 0.12 | 0.14 | 0.17 | 0.18 | 0.15 |
| %18:0 | 1.29 | 1.24 | 1.07 | 1.28 | 1.41 | 1.43 | 1.36 | 1.48 | 1.35 |
| %18:1 n-9 | 0.00 | 0.08 | 0.07 | 0.09 | 0.09 | 0.08 | 0.10 | 0.09 | 0.06 |
| %18:1 n-7 | 0.00 | 0.00 | 0.00 | 0.00 | 0.00 | 0.00 | 0.00 | 0.00 | 0.00 |
| %18:2 | 0.00 | 0.00 | 0.00 | 0.00 | 0.00 | 0.00 | 0.00 | 0.00 | 0.00 |
| %18:3 n-6 | 0.00 | 0.00 | 0.12 | 0.05 | 0.00 | 0.00 | 0.00 | 0.00 | 0.00 |
| %18:3 n-3 | 0.00 | 0.00 | 0.00 | 0.00 | 0.00 | 0.00 | 0.00 | 0.00 | 0.00 |
| %18:4 n-3 | 0.00 | 0.00 | 0.00 | 0.00 | 0.00 | 0.00 | 0.00 | 0.00 | 0.00 |
| %20:0 | 0.39 | 0.36 | 0.29 | 0.37 | 0.42 | 0.42 | 0.39 | 0.40 | 0.41 |
| %20:1 n-9 | 0.00 | 0.15 | 0.13 | 0.11 | 0.24 | 0.13 | 0.19 | 0.16 | 0.19 |
| %20:2 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 |
| %20:3 n-6 | 0.00 | 0.00 | 0.05 | 0.00 | 0.00 | 0.00 | 0.00 | 0.00 | 0.00 |
| %20:3 n-3 | 0.37 | 0.00 | 0.12 | 0.00 | 0.00 | 0.00 | 0.00 | 0.00 | 0.00 |
| %20:4 ARA | 0.55 | 0.29 | 0.65 | 0.26 | 0.18 | 0.21 | 0.22 | 0.24 | 0.24 |
| %20:5 n-3 EPA | 2.62 | 3.05 | 4.28 | 2.66 | 2.93 | 2.46 | 2.71 | 2.94 | 2.44 |
| %22:0 | 0.08 | 0.07 | 0.06 | 0.07 | 0.09 | 0.09 | 0.08 | 0.08 | 0.08 |
| %22:1 | 0.00 | 0.00 | 0.00 | 0.00 | 0.00 | 0.00 | 0.00 | 0.00 | 0.00 |
| %22:2 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 |
| %22:4 n-6 | 0.00 | 0.06 | 0.07 | 0.05 | 0.00 | 0.00 | 0.00 | 0.00 | 0.00 |
| %22:5 n-6 | 3.19 | 3.59 | 4.28 | 3.46 | 3.07 | 3.32 | 3.17 | 3.18 | 3.24 |
| %22:5 n-3 | 0.18 | 0.25 | 0.27 | 0.18 | 0.17 | 0.17 | 0.16 | 0.17 | 0.17 |
| %22:6 n-3 DHA | 56.88 | 57.74 | 58.32 | 56.70 | 58.65 | 56.45 | 56.83 | 56.19 | 55.06 |
| %24:0 | 0.00 | 0.00 | 0.00 | 0.00 | 0.00 | 0.00 | 0.00 | 0.00 | 0.00 |
| %24:1 | 0.00 | 0.07 | 0.15 | 0.10 | 0.10 | 0.11 | 0.10 | 0.10 | 0.07 |
| % Fat | 46.83 | 48.91 | 58.95 | 54.80 | 35.41 | 48.60 | 44.93 | 43.01 | 51.93 |
| % Unknown | 0.85 | 1.55 | 1.63 | 1.57 | 1.09 | 1.35 | 1.31 | 1.28 | 1.19 |

TABLE 20

Mutants of Thraustochytrid Strain ATCC Accession No. PTA-9695

| Fatty Acids | control ATCC PTA-9695 | Mutant 53 | Mutant 54 | Mutant 55 | Mutant 56 | Mutant 57 | Mutant 58 | Mutant 60 | Mutant 61 | Mutant 65 |
|---|---|---|---|---|---|---|---|---|---|---|
| %08:0 | 0.00 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 | 0.00 |
| %12:0 | 0.10 | 0.09 | 0.08 | 0.12 | 0.08 | 0.08 | 0.08 | 0.08 | 0.10 | 0.08 |
| %12:1 | 0.00 | 0.00 | 0.00 | 0.00 | 0.00 | 0.00 | 0.00 | 0.00 | 0.00 | 0.00 |
| %13:0 | 0.11 | 0.11 | 0.12 | 0.08 | 0.09 | 0.13 | 0.16 | 0.14 | 0.09 | 0.14 |
| %13:1 | 0.00 | 0.00 | 0.00 | 0.00 | 0.00 | 0.00 | 0.00 | 0.00 | 0.00 | 0.00 |
| %14:0 | 1.79 | 1.74 | 1.63 | 2.13 | 1.67 | 1.59 | 1.59 | 1.59 | 1.85 | 1.58 |
| %14:1 | 0.00 | 0.00 | 0.00 | 0.00 | 0.00 | 0.00 | 0.00 | 0.00 | 0.00 | 0.00 |
| %15:1 | 0.00 | 0.53 | 0.52 | 0.48 | 0.51 | 0.52 | 0.45 | 0.50 | 0.51 | 0.48 |
| %16:0 | 30.98 | 30.13 | 29.54 | 33.01 | 31.08 | 29.37 | 30.65 | 29.39 | 31.15 | 30.03 |
| %16:1 | 0.27 | 0.21 | 0.23 | 0.26 | 0.26 | 0.14 | 0.25 | 0.22 | 0.26 | 0.25 |
| %16:2 | 0.00 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 | 0.00 |
| %17:0 | 0.12 | 0.15 | 0.14 | 0.14 | 0.14 | 0.16 | 0.12 | 0.13 | 0.14 | 0.13 |

TABLE 20-continued

Mutants of Thraustochytrid Strain ATCC Accession No. PTA-9695

| Fatty Acids | control ATCC PTA-9695 | Mutant 53 | Mutant 54 | Mutant 55 | Mutant 56 | Mutant 57 | Mutant 58 | Mutant 60 | Mutant 61 | Mutant 65 |
|---|---|---|---|---|---|---|---|---|---|---|
| %18:0 | 1.29 | 1.30 | 1.30 | 1.37 | 1.38 | 1.37 | 1.46 | 1.30 | 1.30 | 1.35 |
| %18:1 n-9 | 0.00 | 0.08 | 0.08 | 0.00 | 0.06 | 0.11 | 0.09 | 0.10 | 0.07 | 0.07 |
| %18:1 n-7 | 0.00 | 0.00 | 0.00 | 0.00 | 0.00 | 0.00 | 0.00 | 0.00 | 0.00 | 0.00 |
| %18:2 | 0.00 | 0.00 | 0.00 | 0.00 | 0.00 | 0.00 | 0.00 | 0.00 | 0.00 | 0.00 |
| %18:3 n-6 | 0.00 | 0.00 | 0.00 | 0.00 | 0.00 | 0.00 | 0.00 | 0.00 | 0.00 | 0.00 |
| %18:3 n-3 | 0.00 | 0.00 | 0.00 | 0.00 | 0.00 | 0.00 | 0.00 | 0.00 | 0.00 | 0.00 |
| %18:4 n-3 | 0.00 | 0.00 | 0.00 | 0.00 | 0.00 | 0.00 | 0.00 | 0.00 | 0.00 | 0.00 |
| %20:0 | 0.39 | 0.38 | 0.39 | 0.40 | 0.42 | 0.38 | 0.43 | 0.39 | 0.39 | 0.41 |
| %20:1 n-9 | 0.00 | 0.19 | 0.16 | 0.13 | 0.19 | 0.20 | 0.17 | 0.14 | 0.13 | 0.21 |
| %20:2 | 0.00 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 | 0.00 |
| %20:3 n-6 | 0.00 | 0.00 | 0.00 | 0.00 | 0.00 | 0.00 | 0.00 | 0.00 | 0.00 | 0.00 |
| %20:3 n-3 | 0.37 | 0.00 | 0.00 | 0.00 | 0.00 | 0.00 | 0.00 | 0.00 | 0.00 | 0.00 |
| %20:4 ARA | 0.55 | 0.25 | 0.21 | 0.26 | 0.22 | 0.25 | 0.51 | 0.20 | 0.24 | 0.19 |
| %20:5 n-3 EPA | 2.62 | 2.75 | 2.78 | 2.81 | 2.67 | 2.78 | 5.76 | 2.72 | 2.59 | 2.82 |
| %22:0 | 0.08 | 0.08 | 0.08 | 0.08 | 0.09 | 0.08 | 0.09 | 0.08 | 0.08 | 0.09 |
| %22:1 | 0.00 | 0.00 | 0.00 | 0.00 | 0.00 | 0.00 | 0.00 | 0.00 | 0.00 | 0.00 |
| %22:2 | 0.00 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 | 0.00 |
| %22:4 n-6 | 0.00 | 0.00 | 0.00 | 0.00 | 0.00 | 0.00 | 0.00 | 0.00 | 0.06 | 0.00 |
| %22:5 n-6 | 3.19 | 3.47 | 3.20 | 3.25 | 3.19 | 3.43 | 2.62 | 3.30 | 3.42 | 3.18 |
| %22:5 n-3 | 0.18 | 0.18 | 0.18 | 0.17 | 0.17 | 0.20 | 0.59 | 0.17 | 0.17 | 0.17 |
| %22:6 n-3 DHA | 56.88 | 56.99 | 58.07 | 54.04 | 56.38 | 57.76 | 54.09 | 58.21 | 55.91 | 57.56 |
| %24:0 | 0.00 | 0.00 | 0.00 | 0.00 | 0.00 | 0.00 | 0.00 | 0.00 | 0.00 | 0.00 |
| %24:1 | 0.00 | 0.09 | 0.09 | 0.07 | 0.10 | 0.09 | 0.11 | 0.10 | 0.07 | 0.08 |
| % Fat | 46.83 | 45.83 | 39.59 | 48.81 | 41.92 | 43.97 | 33.96 | 36.97 | 50.40 | 36.21 |
| % Unknown | 0.85 | 1.28 | 1.19 | 1.19 | 1.29 | 1.35 | 0.77 | 1.24 | 1.48 | 1.17 |

TABLE 21

Mutants of Thraustochytrid Strain ATCC Accession No. PTA-9695

| Fatty Acids | control ATCC PTA-9695 | Mutant 66 | Mutant 67 | Mutant 68 ATCC PTA-9696 | Mutant 69 | Mutant 70 ATCC PTA-9697 | Mutant 71 | Mutant 72 ATCC PTA-9698 | Mutant 73 | Mutant 74 |
|---|---|---|---|---|---|---|---|---|---|---|
| %08:0 | 0.00 | 0.00 | 0.00 | 0.00 | 0.00 | 0.00 | 0.00 | 0.00 | 0.00 | 0.00 |
| %09:0 | 0.00 | 0.00 | 0.00 | 0.00 | 0.00 | 0.00 | 0.00 | 0.00 | 0.00 | 0.00 |
| %10:0 | 0.00 | 0.00 | 0.00 | 0.00 | 0.00 | 0.00 | 0.00 | 0.00 | 0.00 | 0.00 |
| %11:0 | 0.00 | 0.00 | 0.00 | 0.00 | 0.00 | 0.00 | 0.00 | 0.00 | 0.00 | 0.00 |
| %11:1 | 0.00 | 0.00 | 0.00 | 0.00 | 0.00 | 0.00 | 0.00 | 0.00 | 0.00 | 0.00 |
| %12:0 | 0.15 | 0.00 | 0.00 | 0.00 | 0.00 | 0.00 | 0.00 | 0.13 | 0.00 | 0.00 |
| %12:1 | 0.00 | 0.00 | 0.00 | 0.00 | 0.00 | 0.00 | 0.00 | 0.00 | 0.00 | 0.00 |
| %13:0 | 0.00 | 0.00 | 0.00 | 0.00 | 0.00 | 0.00 | 0.00 | 0.00 | 0.00 | 0.00 |
| %13:1 | 0.00 | 0.00 | 0.00 | 0.00 | 0.00 | 0.00 | 0.22 | 0.00 | 0.00 | 0.00 |
| %14:0 | 2.42 | 2.29 | 2.07 | 2.09 | 2.11 | 2.21 | 2.27 | 2.29 | 1.97 | 2.05 |
| %14:1 | 0.00 | 0.00 | 0.00 | 0.00 | 0.00 | 0.00 | 0.19 | 0.00 | 0.00 | 0.00 |
| %15:1 | 0.55 | 0.47 | 0.48 | 0.47 | 0.47 | 0.44 | 0.46 | 0.40 | 0.50 | 0.47 |
| %16:0 | 39.19 | 31.02 | 26.20 | 25.84 | 27.79 | 28.14 | 28.89 | 33.49 | 24.50 | 23.95 |
| %16:1 | 0.43 | 0.19 | 0.00 | 0.00 | 0.00 | 0.19 | 0.21 | 0.00 | 0.00 | 0.00 |
| %16:2 | 0.00 | 0.00 | 0.00 | 0.00 | 0.00 | 0.00 | 0.00 | 0.00 | 0.00 | 0.00 |
| %16:3 | 0.00 | 0.00 | 0.00 | 0.00 | 0.00 | 0.00 | 0.00 | 0.00 | 0.00 | 0.00 |
| %17:0 | 0.16 | 0.00 | 0.00 | 0.00 | 0.00 | 0.00 | 0.00 | 0.13 | 0.00 | 0.00 |
| %18:0 | 1.67 | 1.68 | 1.22 | 1.22 | 1.44 | 1.49 | 1.51 | 2.24 | 1.11 | 1.02 |
| %18:1 n-9 | 0.00 | 0.00 | 0.00 | 0.00 | 0.00 | 0.00 | 0.00 | 0.00 | 0.00 | 0.00 |
| %18:1 n-7 | 0.00 | 0.00 | 0.00 | 0.00 | 0.00 | 0.00 | 0.00 | 0.00 | 0.00 | 0.00 |
| %18:2 | 0.00 | 0.00 | 0.00 | 0.00 | 0.00 | 0.00 | 0.00 | 0.00 | 0.00 | 0.00 |
| %18:3 n-6 | 0.00 | 0.00 | 0.00 | 0.00 | 0.00 | 0.00 | 0.00 | 0.00 | 0.00 | 0.00 |
| %18:3 n-3 | 0.00 | 0.18 | 0.20 | 0.21 | 0.19 | 0.17 | 0.22 | 0.16 | 0.22 | 0.22 |
| %18:4 n-3 | 0.00 | 0.00 | 0.00 | 0.00 | 0.00 | 0.00 | 0.00 | 0.00 | 0.00 | 0.00 |
| %20:0 | 0.49 | 0.41 | 0.32 | 0.31 | 0.35 | 0.37 | 0.44 | 0.52 | 0.29 | 0.27 |
| %20:1 n-9 | 0.00 | 0.00 | 0.00 | 0.00 | 0.00 | 0.00 | 0.00 | 0.00 | 0.00 | 0.00 |
| %20:2 | 0.00 | 0.00 | 0.00 | 0.00 | 0.00 | 0.00 | 0.00 | 0.00 | 0.00 | 0.00 |
| %20:3 n-9 | 0.00 | 0.00 | 0.00 | 0.00 | 0.00 | 0.00 | 0.00 | 0.00 | 0.00 | 0.00 |
| %20:3 n-6 | 0.00 | 0.00 | 0.00 | 0.00 | 0.15 | 0.00 | 0.00 | 0.00 | 0.00 | 0.00 |
| %20:3 n-3 | 0.00 | 0.00 | 0.00 | 0.00 | 0.00 | 0.00 | 0.00 | 0.00 | 0.00 | 0.00 |
| %20:4 ARA | 0.18 | 0.16 | 0.33 | 0.27 | 0.24 | 0.37 | 0.30 | 0.27 | 0.38 | 0.39 |
| %20:5 n-3 EPA | 1.76 | 2.30 | 3.86 | 3.97 | 3.32 | 4.12 | 3.09 | 2.74 | 4.43 | 4.53 |
| %22:0 | 0.33 | 0.46 | 0.35 | 0.44 | 0.48 | 0.38 | 0.43 | 0.12 | 0.35 | 0.34 |

TABLE 21-continued

Mutants of Thraustochytrid Strain ATCC Accession No. PTA-9695

| Fatty Acids | control ATCC PTA-9695 | Mutant 66 | Mutant 67 | Mutant 68 ATCC PTA-9696 | Mutant 69 | Mutant 70 ATCC PTA-9697 | Mutant 71 | Mutant 72 ATCC PTA-9698 | Mutant 73 | Mutant 74 |
|---|---|---|---|---|---|---|---|---|---|---|
| %22:1 | 0.00 | 0.00 | 0.00 | 0.00 | 0.00 | 0.00 | 0.00 | 0.00 | 0.00 | 0.00 |
| %22:2 | 0.00 | 0.00 | 0.00 | 0.00 | 0.00 | 0.00 | 0.00 | 0.00 | 0.00 | 0.00 |
| %22:3 | 0.00 | 0.00 | 0.00 | 0.00 | 0.00 | 0.00 | 0.00 | 0.00 | 0.00 | 0.00 |
| %22:4 n-6 | 0.00 | 0.00 | 0.00 | 0.00 | 0.00 | 0.00 | 0.00 | 0.00 | 0.00 | 0.00 |
| %22:5 n-6 | 2.62 | 2.83 | 3.17 | 2.66 | 2.72 | 2.95 | 3.46 | 2.79 | 3.17 | 3.19 |
| %22:5 n-3 | 0.18 | 0.18 | 0.46 | 0.42 | 0.34 | 0.61 | 0.25 | 0.27 | 0.48 | 0.57 |
| %22:6 n-3 DHA | 49.52 | 57.01 | 60.60 | 61.42 | 59.74 | 58.03 | 55.62 | 53.06 | 61.83 | 62.23 |
| %24:0 | 0.00 | 0.00 | 0.00 | 0.00 | 0.00 | 0.00 | 0.00 | 0.00 | 0.00 | 0.00 |
| %24:1 | 0.00 | 0.00 | 0.00 | 0.00 | 0.00 | 0.00 | 0.00 | 0.00 | 0.00 | 0.00 |
| % Fat | 52.70 | 49.32 | 48.51 | 49.49 | 48.80 | 53.65 | 40.38 | 63.40 | 48.27 | 46.63 |
| % Unknown | 0.35 | 0.82 | 0.73 | 0.66 | 0.67 | 0.73 | 2.46 | 1.18 | 0.78 | 0.76 |

Example 8

Four thraustochytrid samples were obtained from the American Tissue and Culture Collection (ATCC) and each sample was analyzed for the fatty acid profile of the biomass, the fatty acid profile of the extracted crude oil, the triacylglyceride (TAG) fraction of the crude oil, and the polar lipid (PL) fraction of the crude oil. The samples analyzed were ATCC 34304, 20890, 20889, and 20892. The strains were inoculated into 250 ml shake flask containing 50 mls of the following medium: 1 g peptone, 1 g yeast extract, 5 g glucose in 1 liter of artificial seawater. Cultures were incubated at 20° C. with shaking at 200 rpm on an orbital shaker. After 7 days the cultures was harvested by centrifugation (5087×g), washed with a mixture of water:isopropanol (1:1), and centrifuged again. The resulting pellet was freeze dried. The crude oil was extracted from the dried biomass using the method of Bligh and Dyer (*Can. J. of Biol. And Phys.* 37: 911-917 (1959)). TAGs and PLs were isolated from the crude oil using a variation of the solid phase extracted (SPE) method developed by Kaluzny et al. (*J. Lipid Res.* 26: 135-140 (1959)). The crude oil and isolated fractions were analyzed for DHA and EPA content as well as the total fatty acid content (as fatty acid methyl esters).

Lipid Extraction—

Crude oil was extracted from the freeze dried biomass by weighing 100 to 200 mg into a 1.5×10 cm screw top test tube, adding 8 mL of a monophasic system consisting of 1:2:0.8 chloroform:methanol:water ($CHCl_3$:MeOH:$H_2O$), and homogenizing with a POLYTRON® PT 3100 dispersing unit equipped with a PT-DA 3012/2 aggregate. The sample was homogenized for 2 minutes at 10000 rpm while immersed in an ice bath. A biphasic system was produced by adding 2.1 mL of $CHCl_3$, vortexing for 1 minute, adding 1.7 mL of $H_2O$, and vortexing again for an additional 1 minute. The bottom (organic) layer was removed using a Pasteur pipet and placed into a collection flask. The MeOH—$H_2O$ layer left in the test tube was re-extracted two more times with 2.1 mL portions of $CHCl_3$. The organic layers were combined and dried under a stream of nitrogen.

Solid Phase Extraction—

The TAG and PL fractions were separated from the crude lipid by SPE using 500 mg aminopropyl cartridges (Burdick & Jackson) placed in a Vac Elut apparatus. The cartridge was condition with 5 mL of hexane, and 10 to 20 mg of each sample was dissolved in 400 µL $CHCl_3$ and applied to the cartridge. The column was washed with 4 mL of 2:1 $CHCl_3$:isopropyl alcohol (IPA) to elute all the neutral lipids, which were collected and dried under nitrogen. The fatty acids were then eluted with 5 mL of 2% acetic acid (HOAc) in ether, which was discarded. The PL portion was eluted with 5 mL of McOH, which was collected and dried under nitrogen. The neutral lipid fraction was re-dissolved in 400 µL of hexane and applied to a second aminopropyl column (previously conditioned with 5 mL of hexane). Sterol esters were eluted with 5 mL of 1% ethyl acetate (EtOAc) in hexane and discarded. Finally, TAGs were eluted with 5 mL of 3% EtOAc in hexane, which was collected and dried under nitrogen.

TLC Analysis—

Thin layer chromatography was conducted on silica gel plates. The plates were eluted using a solvent system consisting of petroleum ether:ethyl ether:acetic acid (80:20:1) and were visualized using iodine vapor.

Fatty Acid Analysis—

Samples of biomass, crude oil, isolated TAG, and PL fractions were analyzed for fatty acid composition as FAMEs. Samples were weighed directly into screw cap test tubes, and 1 mL of C19:0 internal standard in toluene and 2 mL of 1.5 N HCl in methanol was added to each tube. The tubes were vortexed briefly and placed in a heating block for 2 hours at 100° C. The tubes were removed from the heating block, allowed to cool, and 1 mL of saturated NaCl in water was added. The tubes were vortexed again, centrifuged, and a portion of the top (organic) layer was placed in a GC vial and analyzed by GC-FID. FAME's were quantified using a 3-point internal standard calibration curve generated using Nu-Chek-Prep GLC reference standard and tentatively identified based on retention time. Fatty acids present were expressed as mg/g and % of total FAME.

ATCC 34304—

The lipid content of the ATCC 34304 biomass was estimated to be 9.1% as the sum of FAME, and the amount of crude oil obtained after solvent extraction was 9.2% by weight, giving a 101% recovery of fat present in the biomass. The EPA and DHA content of the biomass was determined to be 4.8 mg/g and 38.7 mg/g, respectively. The extracted crude oil contained 25.9 mg/g EPA and 238.7 mg/g DHA. The isolated TAG contained 13.9 mg/g EPA and 303.9 mg/g DHA, while the isolated PL contained 38.7 mg/g EPA and 237.980 mg/g DHA. The total fatty acid profiles of the biomass, extracted crude oil, TAG fraction, and PL fraction are shown below in Table 22 and Table 23 calculated as mg/g and % FAME, respectively.

TABLE 22

Fatty Acid Profile of ATCC 34304 Calculated as Milligrams per Gram

| Fatty Acid | Biomass FAME (mg/g) | Crude Oil FAME (mg/g) | TAG FAME (mg/g) | PL FAME (mg/g) |
|---|---|---|---|---|
| C12:0* | 0.0 | 0.0 | 0.0 | 0.0 |
| C14:0* | 1.5 | 8.5 | 13.7 | 1.5 |
| C14:1* | 0.0 | 0.2 | 0.0 | 0.0 |
| C15:0 | 0.0 | 0.0 | 0.0 | 0.0 |
| C16:0* | 20.8 | 138.9 | 250.8 | 73.9 |
| C16:1* | 0.2 | 2.9 | 6.9 | 0.3 |
| C18:0* | 2.1 | 17.8 | 45.6 | 0.8 |
| C18:1 N9* | 3.8 | 29.8 | 74.2 | 4.2 |
| C18:1 N7 | 0.0 | 0.0 | 0.0 | 0.0 |
| C18:2 N6* | 1.5 | 12.0 | 31.0 | 2.5 |
| C20:0* | 0.1 | 0.7 | 1.7 | 0.1 |
| C18:3 N3* | 0.0 | 0.0 | 0.0 | 0.0 |
| C20:1 N9* | 0.0 | 0.1 | 0.3 | 0.0 |
| C18:4 N3 | 0.0 | 8.5 | 0.3 | 0.0 |
| C20:2 N6* | 0.1 | 0.8 | 2.2 | 0.0 |
| C20:3 N6 | 0.0 | 2.5 | 6.3 | 0.5 |
| C22:0* | 0.3 | 5.2 | 0.3 | 0.0 |
| C20:4 N7 | 0.4 | 2.7 | 0.0 | 0.0 |
| C20:3 N3 | 0.0 | 0.0 | 0.6 | 0.0 |
| C20:4N6* | 3.4 | 20.8 | 20.9 | 27.5 |
| C22:1 N9* | 0.0 | 0.0 | 0.0 | 0.0 |
| C20:4 N5 | 0.0 | 0.0 | 0.0 | 0.0 |
| C20:4 N3 | 0.1 | 0.6 | 1.3 | 0.3 |
| C20:5 N3* | 4.8 | 25.9 | 13.9 | 38.7 |
| C24:0* | 0.4 | 0.2 | 0.3 | 0.0 |
| C22:4 N9 | 0.0 | 1.2 | 0.7 | 0.4 |
| C24:1 N9* | 0.9 | 6.9 | 18.2 | 0.8 |
| C22:5 N6* | 11.0 | 60.8 | 51.9 | 45.9 |
| C22:5 N3* | 0.4 | 3.1 | 6.8 | 1.0 |
| C22:6 N3* | 38.7 | 238.7 | 303.9 | 237.9 |
| Sum of all FAME | 91.2 | 590.9 | 855.7 | 437.3 |

TABLE 23

Fatty Acid Profiles of ATCC 34304 Calculated as a Percent of Total FAME

| Fatty Acid | Biomass % FAME | Crude Oil % FAME | TAG % FAME | PL % FAME |
|---|---|---|---|---|
| C12:0* | 0.0 | 0.0 | 0.0 | 0.0 |
| C14:0* | 1.7 | 1.5 | 1.6 | 0.4 |
| C14:1* | 0.0 | 0.0 | 0.0 | 0.0 |
| C15:0 | 0.0 | 0.0 | 0.0 | 0.0 |
| C16:0* | 22.8 | 24.2 | 29.3 | 16.9 |
| C16:1* | 0.2 | 0.5 | 0.8 | 0.1 |
| C18:0* | 2.3 | 3.1 | 5.3 | 0.2 |
| C18:1 N9* | 4.2 | 5.2 | 8.7 | 1.0 |
| C18:1 N7 | 0.0 | 0.0 | 0.0 | 0.0 |
| C18:2 N6* | 1.6 | 2.1 | 3.6 | 0.6 |
| C20:0* | 0.1 | 0.1 | 0.2 | 0.0 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.0 | 0.0 | 0.0 |
| C20:2 N6* | 0.1 | 0.1 | 0.3 | 0.0 |
| C20:3 N6 | 0.0 | 0.4 | 0.7 | 0.1 |
| C22:0* | 0.3 | 0.9 | 0.0 | 0.0 |
| C20:4 N7 | 0.5 | 0.0 | 0.0 | 0.0 |
| C20:3 N3 | 0.0 | 0.0 | 0.1 | 0.0 |
| C20:4N6* | 3.7 | 3.4 | 2.4 | 6.3 |
| C22:1 N9* | 0.0 | 0.0 | 0.0 | 0.0 |
| C20:4 N5 | 0.0 | 0.0 | 0.0 | 0.0 |
| C20:4 N3 | 0.1 | 0.1 | 0.2 | 0.1 |
| C20:5 N3* | 5.3 | 4.5 | 1.6 | 8.8 |
| C24:0* | 0.5 | 0.0 | 0.0 | 0.0 |
| C22:4 N9 | 0.0 | 0.0 | 0.1 | 0.1 |
| C24:1 N9* | 1.0 | 1.2 | 2.1 | 0.2 |
| C22:5 N6* | 12.1 | 10.5 | 6.1 | 10.5 |
| C22:5 N3* | 0.5 | 0.5 | 0.8 | 0.2 |
| C22:6 N3* | 42.5 | 41.5 | 35.5 | 54.4 |
| Sum of FAME % | 100.0 | 100.0 | 100.0 | 100.0 |

ATCC 20890—

The lipid content of the ATCC 20890 biomass was estimated to be 9.2% as the sum of FAME, and the amount of crude oil obtained after solvent extraction was 10.2% by weight, giving a 111% recovery of fat present in the biomass. The EPA and DHA content of the biomass was determined to be 12.2 mg/g and 36.6 mg/g, respectively. The extracted crude oil contained 64.7 mg/g EPA and 194.2 mg/g DHA. The isolated TAG contained 41.9 mg/g EPA and 230.2 mg/g DHA, while the isolated PL contained 54.4 mg/g EPA and 149.5 mg/g DHA. The total fatty acid profiles of the biomass, extracted crude oil, TAG fraction, and PL fraction are shown below in Table 24 and Table 25 calculated as mg/g and % FAME, respectively.

TABLE 24

Fatty Acid Profile of ATCC 20890 Calculated as Milligrams per Gram

| Fatty Acid | Biomass FAME (mg/g) | Crude Oil FAME (mg/g) | TAG FAME (mg/g) | PL FAME (mg/g) |
|---|---|---|---|---|
| C12:0* | 0.0 | 0.0 | 0.0 | 0.0 |
| C14:0* | 0.6 | 5.2 | 22.6 | 3.2 |
| C14:1* | 0.0 | 0.0 | 0.0 | 0.2 |
| C15:0 | 0.0 | 0.0 | 0.0 | 0.0 |
| C16:0* | 25.4 | 161.1 | 206.1 | 142.5 |
| C16:1* | 0.2 | 1.3 | 4.7 | 0.8 |
| C18:0* | 1.8 | 12.1 | 58.9 | 7.1 |
| C18:1 N9* | 1.0 | 9.7 | 37.6 | 2.4 |
| C18:1 N7 | 0.0 | 0.0 | 0.0 | 0.0 |
| C18:2 N6* | 0.8 | 4.8 | 6.9 | 3.9 |
| C20:0* | 0.1 | 0.0 | 0.0 | 0.3 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.0 | 0.0 | 0.0 |
| C20:2 N6* | 1.9 | 11.1 | 14.2 | 13.1 |
| C20:3 N6 | 1.0 | 5.4 | 2.4 | 8.0 |
| C22:0* | 0.0 | 0.0 | 0.0 | 0.0 |
| C20:4 N7 | 0.0 | 0.0 | 0.0 | 0.0 |
| C20:3 N3 | 0.0 | 0.0 | 0.0 | 0.0 |
| C20:4N6* | 5.3 | 33.6 | 35.8 | 35.3 |
| C22:1 N9* | 0.0 | 0.0 | 0.0 | 0.0 |
| C20:4 N5 | 0.2 | 0.0 | 0.0 | 1.1 |
| C20:4 N3 | 0.1 | 2.2 | 0.0 | 3.1 |
| C20:5 N3* | 12.2 | 64.7 | 41.9 | 54.4 |
| C24:0* | 0.3 | 0.0 | 0.0 | 0.2 |
| C22:4 N9 | 0.0 | 0.0 | 0.0 | 0.0 |
| C24:1 N9* | 0.3 | 1.4 | 1.6 | 1.9 |
| C22:5 N6* | 0.5 | 2.4 | 1.4 | 3.0 |
| C22:5 N3* | 3.6 | 19.4 | 23.9 | 19.8 |
| C22:6 N3* | 36.6 | 194.2 | 230.2 | 149.5 |
| Sum of all FAME | 92.3 | 535.1 | 735.0 | 450.9 |

TABLE 25

Fatty Acid Profiles of ATCC 20890 Calculated as a Percent of Total FAME

| Fatty Acid | Biomass % FAME | Crude Oil % FAME | TAG % FAME | PL % FAME |
|---|---|---|---|---|
| C12:0* | 0.0 | 0.0 | 0.0 | 0.0 |
| C14:0* | 0.7 | 1.0 | 3.1 | 0.7 |
| C14:1* | 0.0 | 0.0 | 0.0 | 0.0 |
| C15:0 | 0.0 | 0.0 | 0.0 | 0.0 |
| C16:0* | 27.6 | 30.1 | 28.0 | 31.6 |
| C16:1* | 0.2 | 0.3 | 0.6 | 0.2 |
| C18:0* | 2.0 | 2.3 | 8.0 | 1.6 |
| C18:1 N9* | 1.1 | 1.8 | 5.1 | 0.5 |
| C18:1 N7 | 0.0 | 0.0 | 0.0 | 0.0 |
| C18:2 N6* | 0.9 | 0.9 | 0.9 | 0.9 |
| C20:0* | 0.1 | 0.0 | 0.0 | 0.1 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.0 | 0.0 | 0.0 |
| C20:2 N6* | 2.1 | 2.1 | 1.9 | 2.9 |
| C20:3 N6 | 1.1 | 1.0 | 0.3 | 1.8 |
| C22:0* | 0.0 | 0.0 | 0.0 | 0.0 |
| C20:4 N7 | 0.0 | 0.0 | 0.0 | 0.0 |
| C20:3 N3 | 0.0 | 0.0 | 0.0 | 0.0 |
| C20:4N6* | 5.8 | 6.3 | 4.9 | 7.8 |
| C22:1 N9* | 0.0 | 0.0 | 0.0 | 0.0 |
| C20:4 N5 | 0.2 | 0.0 | 0.0 | 0.3 |
| C20:4 N3 | 0.1 | 0.4 | 0.0 | 0.7 |
| C20:5 N3* | 13.2 | 12.1 | 5.7 | 12.1 |
| C24:0* | 0.3 | 0.0 | 0.0 | 0.0 |
| C22:4 N9 | 0.0 | 0.0 | 0.0 | 0.0 |
| C24:1 N9* | 0.3 | 0.3 | 0.2 | 0.4 |
| C22:5 N6* | 0.6 | 0.4 | 0.2 | 0.7 |
| C22:5 N3* | 3.9 | 3.6 | 3.2 | 4.4 |
| C22:6 N3* | 39.7 | 36.3 | 31.3 | 33.2 |
| Sum of FAME % | 100.00 | 100.0 | 100.0 | 100.0 |

ATCC 20889—

The lipid content of the biomass was estimated to be 3.3% as the sum of FAME, and the amount of crude oil obtained after solvent extraction was 3.4% by weight, giving a 103% recovery of fat present in the biomass. The EPA and DHA content of the biomass was determined to be 2.3 mg/g and 16.5 mg/g, respectively. The extracted crude oil contained 26.8 mg/g EPA and 205.1 mg/g DHA. The isolated TAG contained 7.3 mg/g EPA and 185.9 mg/g DHA, while the isolated PL contained 35.2 mg/g EPA and 218.6 mg/g DHA. The total fatty acid profiles of the biomass, extracted crude oil, TAG fraction, and PL fraction are shown below in Table 26 and Table 27 calculated as mg/g and % FAME, respectively.

TABLE 26

Fatty Acid Profile of ATCC 20889 Calculated as Milligrams per Gram

| Fatty Acid | Biomass FAME (mg/g) | Crude Oil FAME (mg/g) | TAG FAME (mg/g) | PL FAME (mg/g) |
|---|---|---|---|---|
| C12:0* | 0.0 | 0.0 | 0.0 | 0.0 |
| C14:0* | 0.5 | 8.3 | 32.0 | 2.8 |
| C14:1* | 0.0 | 0.0 | 0.0 | 0.0 |
| C15:0 | 0.0 | 0.0 | 0.0 | 0.1 |
| C16:0* | 6.6 | 80.3 | 150.8 | 50.4 |
| C16:1* | 0.1 | 1.7 | 12.3 | 0.0 |
| C18:0* | 0.3 | 4.8 | 9.7 | 1.6 |
| C18:1 N9* | 0.6 | 6.6 | 7.6 | 1.2 |
| C18:1 N7 | 0.0 | 0.0 | 0.0 | 0.0 |
| C18:2 N6* | 0.0 | 0.4 | 1.1 | 0.1 |
| C20:0* | 0.0 | 0.1 | 2.1 | 0.0 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.0 | 0.0 | 0.0 |
| C20:2 N6* | 0.0 | 0.0 | 0.0 | 0.0 |
| C20:3 N6 | 0.0 | 0.1 | 0.7 | 0.1 |
| C22:0* | 0.0 | 0.0 | 0.1 | 0.0 |
| C20:4 N7 | 0.0 | 0.0 | 0.0 | 0.0 |
| C20:3 N3 | 0.0 | 0.0 | 0.0 | 0.0 |
| C20:4N6* | 0.4 | 1.4 | 1.1 | 7.2 |
| C22:1 N9* | 0.0 | 0.0 | 0.0 | 0.0 |
| C20:4 N5 | 0.0 | 0.0 | 0.0 | 0.0 |
| C20:4 N3 | 0.0 | 0.5 | 0.9 | 0.5 |
| C20:5 N3* | 2.3 | 26.8 | 7.3 | 35.2 |
| C24:0* | 0.1 | 0.4 | 1.8 | 0.0 |
| C22:4 N9 | 0.0 | 3.4 | 0.2 | 2.8 |
| C24:1 N9* | 0.0 | 0.0 | 0.8 | 0.3 |
| C22:5 N6* | 5.0 | 63.6 | 76.2 | 45.9 |
| C22:5 N3* | 0.2 | 1.8 | 2.2 | 2.0 |
| C22:6 N3* | 16.5 | 205.1 | 185.9 | 218.6 |
| Sum of all FAME | 32.8 | 405.2 | 493.0 | 368.7 |

TABLE 27

Fatty Acid Profiles of ATCC 20889 Calculated as a Percent of Total FAME

| Fatty Acid | Biomass % FAME | Crude Oil % FAME | TAG % FAME | PL % FAME |
|---|---|---|---|---|
| C12:0* | 0.0 | 0.0 | 0.0 | 0.0 |
| C14:0* | 1.4 | 2.0 | 6.5 | 0.8 |
| C14:1* | 0.0 | 0.0 | 0.0 | 0.0 |
| C15:0 | 0.0 | 0.0 | 0.0 | 0.0 |
| C16:0* | 20.3 | 19.8 | 30.6 | 13.7 |
| C16:1* | 0.4 | 0.4 | 2.5 | 0.0 |
| C18:0* | 0.8 | 1.2 | 2.0 | 0.4 |
| C18:1 N9* | 1.8 | 1.6 | 1.5 | 0.3 |
| C18:1 N7 | 0.0 | 0.0 | 0.0 | 0.0 |
| C18:2 N6* | 0.1 | 0.1 | 0.2 | 0.0 |
| C20:0* | 0.0 | 0.0 | 0.4 | 0.0 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.0 | 0.0 | 0.0 |
| C20:2 N6* | 0.0 | 0.0 | 0.0 | 0.0 |
| C20:3 N6 | 0.0 | 0.0 | 0.1 | 0.0 |
| C22:0* | 0.0 | 0.0 | 0.0 | 0.0 |
| C20:4 N7 | 0.0 | 0.0 | 0.0 | 0.0 |
| C20:3 N3 | 0.0 | 0.0 | 0.0 | 0.0 |
| C20:4N6* | 1.3 | 0.4 | 0.2 | 2.0 |
| C22:1 N9* | 0.0 | 0.0 | 0.0 | 0.0 |
| C20:4 N5 | 0.0 | 0.0 | 0.0 | 0.0 |
| C20:4 N3 | 0.1 | 0.1 | 0.2 | 0.1 |
| C20:5 N3* | 7.0 | 6.6 | 1.5 | 9.5 |
| C24:0* | 0.3 | 0.1 | 0.4 | 0.0 |
| C22:4 N9 | 0.0 | 0.8 | 0.0 | 0.8 |
| C24:1 N9* | 0.0 | 0.0 | 0.2 | 0.1 |
| C22:5 N6* | 15.3 | 15.7 | 15.5 | 12.5 |
| C22:5 N3* | 0.5 | 0.5 | 0.5 | 0.5 |
| C22:6 N3* | 50.2 | 50.6 | 37.7 | 59.3 |
| Sum of FAME % | 100.0 | 100.0 | 100.0 | 100.0 |

ATCC 20892—

The lipid content of the biomass was estimated to be 8.8% as the sum of FAME, and the amount of crude oil obtained after solvent extraction was 12.1% by weight, giving a 138% recovery of fat present in the biomass. The EPA and DHA content of the biomass was determined to be 8.3 mg/g and 43.3 mg/g, respectively. The extracted crude oil contained 50.5 mg/g EPA and 260.1 mg/g DHA. The isolated TAG contained 98.7 mg/g EPA and 407.7 mg/g DHA, while the isolated PL contained 50.4 mg/g EPA and 243.12 mg/g DHA. The total fatty acid profiles of the biomass, extracted crude oil, TAG fraction, and PL fraction are shown below in Table 28 and Table 29 calculated as mg/g and % FAME, respectively.

TABLE 28

Fatty Acid Profile of ATCC 20892 Calculated as Milligrams per Gram

| Fatty Acid | Biomass FAME (mg/g) | Crude Oil FAME (mg/g) | TAG FAME (mg/g) | PL FAME (mg/g) |
|---|---|---|---|---|
| C12:0* | 0.0 | 0.0 | 0.0 | 0.0 |
| C14:0* | 7.3 | 42.2 | 29.7 | 54.7 |
| C14:1* | 0.0 | 0.0 | 0.0 | 0.2 |
| C15:0 | 0.0 | 0.0 | 0.0 | 0.0 |
| C16:0* | 18.9 | 109.0 | 133.5 | 116.7 |
| C16:1* | 0.0 | 0.8 | 3.5 | 0.2 |
| C18:0* | 0.0 | 2.6 | 9.1 | 0.7 |
| C18:1 N9* | 0.6 | 7.3 | 22.0 | 1.3 |
| C18:1 N7 | 0.0 | 0.0 | 0.0 | 0.0 |
| C18:2 N6* | 0.0 | 1.4 | 9.7 | 0.4 |
| C20:0* | 0.0 | 0.0 | 0.0 | 0.0 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.6 | 0.0 | 0.1 |
| C20:2 N6* | 0.0 | 0.0 | 0.0 | 0.0 |
| C20:3 N6 | 0.3 | 1.1 | 6.3 | 0.6 |
| C22:0* | 0.0 | 0.0 | 0.0 | 0.0 |
| C20:4 N7 | 0.0 | 0.0 | 0.0 | 0.0 |
| C20:3 N3 | 0.0 | 0.0 | 0.0 | 0.0 |
| C20:4N6* | 1.3 | 7.6 | 15.8 | 7.8 |
| C22:1 N9* | 0.0 | 0.0 | 0.0 | 0.0 |
| C20:4 N5 | 0.0 | 0.0 | 0.0 | 0.0 |
| C20:4 N3 | 0.3 | 1.5 | 4.7 | 1.4 |
| C20:5 N3* | 8.3 | 49.6 | 97.0 | 49.8 |
| C24:0* | 0.0 | 0.0 | 0.0 | 0.0 |
| C22:4 N9 | 0.2 | 0.0 | 0.0 | 0.1 |
| C24:1 N9* | 0.0 | 1.1 | 4.9 | 1.0 |
| C22:5 N6* | 2.8 | 16.1 | 25.3 | 15.8 |
| C22:5 N3* | 1.1 | 6.6 | 23.9 | 6.0 |
| C22:6 N3* | 43.4 | 254.3 | 398.3 | 239.5 |
| Sum of all FAME | 87.5 | 508.0 | 800.7 | 498.2 |

TABLE 29

Fatty Acid Profiles of ATCC 20892 Calculated as a Percent of Total FAME

| Fatty Acid | Biomass % FAME | Crude Oil % FAME | TAG % FAME | PL % FAME |
|---|---|---|---|---|
| C12:0* | 0.0 | 0.0 | 0.0 | 0.0 |
| C14:0* | 8.3 | 8.3 | 3.6 | 11.0 |
| C14:1* | 0.0 | 0.0 | 0.0 | 0.0 |
| C15:0 | 0.0 | 0.0 | 0.0 | 0.0 |
| C16:0* | 21.6 | 21.4 | 16.4 | 23.4 |
| C16:1* | 0.0 | 0.2 | 0.5 | 0.0 |
| C18:0* | 0.0 | 0.5 | 1.1 | 0.1 |
| C18:1 N9* | 0.7 | 1.4 | 2.6 | 0.2 |
| C18:1 N7 | 0.0 | 0.0 | 0.0 | 0.0 |
| C18:2 N6* | 0.0 | 0.2 | 1.1 | 0.1 |
| C20:0* | 0.0 | 0.1 | 0.6 | 0.0 |
| C18:3 N3* | 0.0 | 0.0 | 0.0 | 0.0 |
| C20:1 N9* | 0.0 | 0.0 | 0.0 | 0.0 |
| C18:4 N3 | 0.0 | 0.1 | 0.0 | 0.0 |
| C20:2 N6* | 0.0 | 0.0 | 0.0 | 0.0 |
| C20:3 N6 | 0.3 | 0.2 | 0.7 | 0.1 |
| C22:0* | 0.0 | 0.0 | 0.0 | 0.0 |
| C20:4 N7 | 1.9 | 0.8 | 1.6 | 0.2 |
| C20:3 N3 | 0.0 | 0.0 | 0.0 | 0.0 |
| C20:4N6* | 1.4 | 1.5 | 1.9 | 1.6 |
| C22:1 N9* | 0.0 | 0.0 | 0.0 | 0.0 |
| C20:4 N5 | 0.0 | 0.0 | 0.0 | 0.0 |
| C20:4 N3 | 0.3 | 0.3 | 0.5 | 0.3 |
| C20:5 N3* | 9.5 | 9.7 | 11.9 | 10.0 |
| C24:0* | 0.0 | 0.0 | 0.0 | 0.0 |
| C22:4 N9 | 0.2 | 0.0 | 0.0 | 0.0 |
| C24:1 N9* | 0.0 | 0.2 | 0.5 | 0.2 |
| C22:5 N6* | 3.2 | 3.1 | 3.0 | 3.2 |
| C22:5 N3* | 1.3 | 1.2 | 2.8 | 1.2 |
| C22:6 N3* | 49.6 | 49.8 | 49.0 | 48.0 |
| Sum of FAME % | 100.0 | 100.0 | 100.0 | 100.0 |

All publications, patents, and patent applications mentioned in this specification are herein incorporated by reference to the same extent as if each individual publication, patent, or patent application was specifically and individually indicated to be incorporated by reference.

What is claimed:

1. An isolated thraustochytrid biomass, wherein at least 50% by weight of the dry cell weight of the biomass are fatty acids, and wherein at least 50% by weight of the fatty acids are omega-3 fatty acids.

2. The isolated thraustochytrid biomass of claim 1, wherein at least 50% by weight of the fatty acids is docosahexaenoic acid.

3. An isolated thraustochytrid biomass, wherein at least 25% by weight of the dry cell weight of the biomass is docosahexaenoic acid.

4. The isolated thraustochytrid biomass of claim 1 or claim 3, wherein 10% or less by weight of the fatty acids is eicosapentaenoic acid, and wherein the weight ratio of docosahexaenoic acid to eicosapentaenoic acid is at least 5:1.

5. The isolated thraustochytrid biomass of claim 4, wherein 1.5% or less by weight of the fatty acids is arachidonic acid, and wherein the weight ratio of docosahexaenoic acid to arachidonic acid is at least 20:1.

6. The isolated thraustochytrid biomass of claim 5, further comprising docosahexaenoic acid and docosapentaenoic acid n-6 in a weight ratio of at least 10:1.

7. A food product, cosmetic, or pharmaceutical composition for animals or humans, comprising the thraustochytrid biomass of claim 2 or claim 4.

8. The food product of claim 7, wherein the food product is an additive for animal or human food.

9. The food product of claim 7, wherein the food product is a nutritional supplement.

10. The food product of claim 7, wherein the food product is an animal feed.

11. The animal feed of claim 10, wherein the animal feed is an aquaculture feed.

12. The animal feed of claim 10, wherein the animal feed is a domestic animal feed, a zoological animal feed, a work animal feed, a livestock feed, or a combination thereof.

13. The isolated thraustochytrid biomass of claim 2 or claim 4, wherein said biomass further comprising at least one antioxidant.

14. The food product of claim 7, wherein said food product further comprising at least one antioxidant.

15. The animal feed of claim 11, wherein said animal feed further comprising at least one antioxidant.

16. The isolated thraustochytrid biomass of claim 13, wherein said at least one antioxidant is in an amount that is sufficient to inhibit the oxidation of the biomass.

17. The isolated thraustochytrid biomass of claim 1, wherein at least 60% by weight of the fatty acids are omega-3 fatty acids.

18. The isolated thraustochytrid biomass of claim 1, wherein at least 55% by weight of the fatty acids is docosahexaenoic acid.

19. The isolated thraustochytrid biomass of claim 1, wherein at least 30% by weight of the dry cell weight of the biomass is docosahexaenoic acid.

20. A feed product for animals, comprising the thraustochytrid biomass of claim 17, wherein said animal feed further comprises at least one antioxidant, wherein said at least one antioxidant is in an amount that is sufficient to inhibit the oxidation of the biomass.

21. A teed product for animals, comprising the thraustochytrid biomass of claim 18, wherein said animal feed further comprises at least one antioxidant, wherein said at least one antioxidant is in an amount that is sufficient to inhibit the oxidation of the biomass.

22. A feed product for animals, comprising the thraustochytrid biomass of claim 19, wherein said animal feed further comprises at least one antioxidant, wherein said at least one antioxidant is in an amount that is sufficient to inhibit the oxidation of the biomass.

* * * * *

SEQUENCE LISTING

<160> NUMBER OF SEQ ID NOS: 5

<210> SEQ ID NO 1
<211> LENGTH: 1713
<212> TYPE: DNA
<213> ORGANISM: Schizochytrium sp.

<400> SEQUENCE: 1

```
acctggttga tcctgccagc tgtcatttgc tcgtctaaaa gattaagcca tgcatgtcta      60
agtataaaca aattatacgg tgaaactgcg aacggctcat tatatcagtt atagtttctt     120
tgatagtgta tttctatatc tatttggata actgtggcaa ttctagagct aacacatgct     180
ttcgagtggg acttttggt accactgcat ttattagatt ttgaagccaa cgtaaaattg      240
gtgattcatg ataactttgc gaatcgcagt agcgtcttgt acgcggcgat gaatcattca     300
agtttctgcc ccatcagctg tcgatggtac ggtattggcc taccatggct ttcacgggtg     360
```

| | | |
|---|---|---|
| acggagaatt agggtttgat tccggagagg acgcttgaga gacggcgacc acatccaagg | 420 |
| aaggcagcag gcgcgtaaat tacccaatgag ggactccccg aggtagtgac aagaaataaa | 480 |
| aatgaggagc gctttgcgtt tttcaatttg aatgagagaa tcgtacaatc ctcatcgagg | 540 |
| atcaattgga gggcaagtct ggtgccagca gccgcggtaa ctccagctcc aatagcaaat | 600 |
| attagagttg ttgcagttaa aaagctcgta gttgaatttc cgatagtctt tggccgtgtc | 660 |
| cttggtctcg tatcatgggt ttattgtgcc aagatgatcg tcctctatgg ttagtgatag | 720 |
| tcatagtcgt ttactgtaaa aaaactggag tgtttaaagc atttctttgg gaaaggtaca | 780 |
| tattagtata ggataattag ataggacctg tgattcttat ttggttggtt tgtgagtcat | 840 |
| ggtaatgatt aatagggaca atcgggggta ttcgaattta attgtcagag gtgaaattct | 900 |
| tggatttaag aaagtcgaac tactgcgaag gcatttacca aggatgtttt cattaataaa | 960 |
| gaacgaaagt taggggatcg aagatgatta gataccatcg tagtcttaac tgtaaactat | 1020 |
| gccgacttgc gattgtccgt cgttgttttt tcaaaaaaga gacctgggca gcagcacatg | 1080 |
| agaaatcaaa gttttgggt tccgggggga gtatggtcgc aaggctgaaa cttaaaggaa | 1140 |
| ttgacggaag gcaccacca ggagtggagc ctgcggctta attcgactca acacgggaaa | 1200 |
| acttaccagg tccagacata gtaaggattg acagattgag agctctttct tgattctatg | 1260 |
| ggtggtggtg catggccgtt cttagttggt ggagtgattt gtctggttaa ttccgttaac | 1320 |
| gaacgagacc tcagcctact aaatagtggt gcatattgtg agatatgtga caaaaatcgc | 1380 |
| ttcttagagg gacatttcgg gtttaccgga aggaagtttg aggcaataac aggtctgtga | 1440 |
| tgccccctaga tgttctgggc cgcacgcgcg ctacaatgac agattcaaca agtccggtag | 1500 |
| tggagctttt gcttctctat tattactttt ccgagaggaa tggttaatct tctaaatgtc | 1560 |
| tgtcgtgatg gggctagatt tttgcaatta ttaatctcca acgaggaatt cctagtaaac | 1620 |
| gcaagtcatc agcttgcatt gattacgtcc ctgccctttg tacacaccgc ccgtcgcacc | 1680 |
| taccgattga acggtcctat gaaatcttcg gat | 1713 |

<210> SEQ ID NO 2
<211> LENGTH: 924
<212> TYPE: DNA
<213> ORGANISM: Schizochytrium sp.

<400> SEQUENCE: 2

| | | |
|---|---|---|
| atcgaccaga aggatgccta cgtaggggac gaggcgcaga gcaagcgtgg tgtgctgacg | 60 |
| ctcaagtacc cgatcgagca cggcatcgtg accaactggg acgacatgga gaagatctgg | 120 |
| catcacacct tctacaacga gctgcgcgtg gcgcccgagg agcacccgt gctgctcacc | 180 |
| gaggcccccc tcaaccccaa ggcgaaccgc gagcgcatga cccagatcat gttcgagacc | 240 |
| ttcaacgtgc cggccatgta cgtcaacatc caggccgtgc tgtccctgta cgcttcgggc | 300 |
| cgcaccaccg cgccgtgct cgattcggga gatggcgtca cgcacaccgt gcccatctac | 360 |
| gagggctacg cgctcccgca cgcggtgctg cgcatcgacc tggctggccg cgacctgacc | 420 |
| gactacatga tgaagatcct gacggagcgc gggtactcgt tcacgacgac cgccgagcgc | 480 |
| gaaatcgtgc gcgacatcaa ggagaagctg tgctacgtgg cgctcgactt cgaccaggag | 540 |
| atgaagacgg ccgccgagtc gtcgtcgctg agaagagct acgagctgcc ggacggcaac | 600 |
| gtgatcacga tcgcaacga gcgcttccgc tgccccgagg tgctcttcca gccgtcgttc | 660 |
| atcggcaagg aggccgccgg cgtgcacgag accatgttcc agacgatcat gaagtgcgac | 720 |

```
gtcgatatcc gcaaggacct gtacgccaac atcgtcatgt ccggtggctc caccatgtac    780
gagggcatcg ccgcgcgcct ggagaaggag atggtgtcac tggcgccctc caccatgaag    840
atcaaggtgg tcgcgccccc cgagcgcaag tactcggtgt ggatcggcgg ctccatcctg    900
gcctcgctct ccaccttcca gcaa                                           924
```

```
<210> SEQ ID NO 3
<211> LENGTH: 291
<212> TYPE: PRT
<213> ORGANISM: Schizochytrium sp.

<400> SEQUENCE: 3

Val Leu Thr Leu Lys Tyr Pro Ile Glu His Gly Ile Val Thr Asn Trp
1               5                   10                  15

Asp Asp Met Glu Lys Ile Trp His His Thr Phe Tyr Asn Glu Leu Arg
            20                  25                  30

Val Ala Pro Glu Glu His Pro Val Leu Thr Glu Ala Pro Leu Asn
        35                  40                  45

Pro Lys Ala Asn Arg Glu Arg Met Thr Gln Ile Met Phe Glu Thr Phe
    50                  55                  60

Asn Val Pro Ala Met Tyr Val Asn Ile Gln Ala Val Leu Ser Leu Tyr
65                  70                  75                  80

Ala Ser Gly Arg Thr Thr Gly Ala Val Leu Asp Ser Gly Asp Gly Val
                85                  90                  95

Thr His Thr Val Pro Ile Tyr Glu Gly Tyr Ala Leu Pro His Ala Val
            100                 105                 110

Leu Arg Ile Asp Leu Ala Gly Arg Asp Leu Thr Asp Tyr Met Met Lys
        115                 120                 125

Ile Leu Thr Glu Arg Gly Tyr Ser Phe Thr Thr Ala Glu Arg Glu
    130                 135                 140

Ile Val Arg Asp Ile Lys Glu Lys Leu Cys Tyr Val Ala Leu Asp Phe
145                 150                 155                 160

Asp Gln Glu Met Lys Thr Ala Ala Glu Ser Ser Ser Leu Glu Lys Ser
                165                 170                 175

Tyr Glu Leu Pro Asp Gly Asn Val Ile Thr Ile Gly Asn Glu Arg Phe
            180                 185                 190

Arg Cys Pro Glu Val Leu Phe Gln Pro Ser Phe Ile Gly Lys Glu Ala
        195                 200                 205

Ala Gly Val His Glu Thr Met Phe Gln Thr Ile Met Lys Cys Asp Val
    210                 215                 220

Asp Ile Arg Lys Asp Leu Tyr Ala Asn Ile Val Met Ser Gly Gly Ser
225                 230                 235                 240

Thr Met Tyr Glu Gly Ile Ala Ala Arg Leu Glu Lys Glu Met Val Ser
                245                 250                 255

Leu Ala Pro Ser Thr Met Lys Ile Lys Val Val Ala Pro Pro Glu Arg
            260                 265                 270

Lys Tyr Ser Val Trp Ile Gly Gly Ser Ile Leu Ala Ser Leu Ser Thr
        275                 280                 285

Phe Gln Gln
    290

<210> SEQ ID NO 4
<211> LENGTH: 918
<212> TYPE: DNA
<213> ORGANISM: Schizochytrium sp.
```

-continued

```
<400> SEQUENCE: 4
gatctgcagc tggagcgcat caacgtgtac ttcaacgagg ccacgggcgg ccgctacgtg      60
ccgcgcgcca tcctcatgga cctggagccc ggtacgatgg actctgtccg cgccggcccc     120
tttggccagc tcttccgccc agacaacttc gtcttcgggc agacgggcgc cggtaacaac     180
tgggccaagg gccactacac tgagggcgcg gagcttatcg actcggtgct cgacgtggtg     240
cgcaaggagg cagagtcgtg cgactgcctg cagggcttcc agatcaccca ctcgctcggc     300
ggcggcacgg gctccggtat gggcacgctt ctcatcagca agatccgcga ggagtacccc     360
gaccgcatca tgctgacctt ctccatcgtg ccctcgccca aggtgtcgga caccgtcgtg     420
gagccctaca acgcgacgct ctcggtgcac cagctcgtgg agaacgccga cgaggtcatg     480
gtcctcgaca cgaggcgct gtacgacatc tgcttccgca ccttgaagct caccacgccc     540
acctacggcg acctcaacca cctcgtgtgc gccgccatga gcgggtgcac gtgctgcctg     600
cgcttcccgg gccagctcaa tcggacctg cgcaagctgg ccgtcaacct ggtgcccttt     660
ccgcgcctcc acttcttcat gatcggcttc tcgcccctca cctcgcgtgg ctcgcagcag     720
taccgcgccc tgaccgttcc ggagctcacg cagcaggcgt tgacgctaa gaacatgatg     780
tgcgccgcca cccgcgcca cggccgctac ctgacgcgca cgacgctctt ccgcgggcgc     840
atgtcgacca aggaggtgga cgagcagatg ctcaacatcc agaacaagaa ctcgtcgtac     900
tttgtcgagt ggatcccc                                                   918

<210> SEQ ID NO 5
<211> LENGTH: 307
<212> TYPE: PRT
<213> ORGANISM: Schizochytrium sp.

<400> SEQUENCE: 5

Asp Asp Leu Gln Leu Glu Arg Ile Asn Val Tyr Phe Asn Glu Ala Thr
1               5                   10                  15

Gly Gly Arg Tyr Val Pro Arg Ala Ile Leu Met Asp Leu Glu Pro Gly
            20                  25                  30

Thr Met Asp Ser Val Arg Ala Gly Pro Phe Gly Gln Leu Phe Arg Pro
        35                  40                  45

Asp Asn Phe Val Phe Gly Gln Thr Gly Ala Gly Asn Asn Trp Ala Lys
    50                  55                  60

Gly His Tyr Thr Glu Gly Ala Glu Leu Ile Asp Ser Val Leu Asp Val
65                  70                  75                  80

Val Arg Lys Glu Ala Glu Ser Cys Asp Cys Leu Gln Gly Phe Gln Ile
                85                  90                  95

Thr His Ser Leu Gly Gly Gly Thr Gly Ser Gly Met Gly Thr Leu Leu
            100                 105                 110

Ile Ser Lys Ile Arg Glu Glu Tyr Pro Asp Arg Ile Met Leu Thr Phe
        115                 120                 125

Ser Ile Val Pro Ser Pro Lys Val Ser Asp Thr Val Val Glu Pro Tyr
    130                 135                 140

Asn Ala Thr Leu Ser Val His Gln Leu Val Glu Asn Ala Asp Glu Val
145                 150                 155                 160

Met Val Leu Asp Asn Glu Ala Leu Tyr Asp Ile Cys Phe Arg Thr Leu
                165                 170                 175

Lys Leu Thr Thr Pro Thr Tyr Gly Asp Leu Asn His Leu Val Cys Ala
            180                 185                 190

Ala Met Ser Gly Cys Thr Cys Cys Leu Arg Phe Pro Gly Gln Leu Asn
```

-continued

```
                195                 200                 205
Ser Asp Leu Arg Lys Leu Ala Val Asn Leu Val Pro Phe Pro Arg Leu
    210                 215                 220

His Phe Phe Met Ile Gly Phe Ser Pro Leu Thr Ser Arg Gly Ser Gln
225                 230                 235                 240

Gln Tyr Arg Ala Leu Thr Val Pro Glu Leu Thr Gln Gln Ala Phe Asp
                245                 250                 255

Ala Lys Asn Met Met Cys Ala Ala Asp Pro Arg His Gly Arg Tyr Leu
                260                 265                 270

Thr Ala Thr Thr Leu Phe Arg Gly Arg Met Ser Thr Lys Glu Val Asp
        275                 280                 285

Glu Gln Met Leu Asn Ile Gln Asn Lys Asn Ser Ser Tyr Phe Val Glu
    290                 295                 300

Trp Ile Pro
305
```